(12) United States Patent
Aburatani et al.

(10) Patent No.: US 8,273,859 B2
(45) Date of Patent: Sep. 25, 2012

(54) DIAGNOSTIC AGENT AND THERAPEUTIC AGENT FOR PANCREATIC CANCER

(75) Inventors: Hiroyuki Aburatani, Musashino (JP); Hiroko Iwanari, Shimotuke (JP); Isao Kohno, Narita (JP)

(73) Assignees: Perseus Proteomics Inc., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/182,492

(22) Filed: Jul. 14, 2011

(65) Prior Publication Data

US 2011/0288278 A1 Nov. 24, 2011

Related U.S. Application Data

(62) Division of application No. 12/297,759, filed as application No. PCT/JP2007/000423 on Apr. 18, 2007.

(30) Foreign Application Priority Data

| Apr. 18, 2006 | (JP) | 2006-114134 |
| Oct. 26, 2006 | (JP) | 2006-291091 |
| Dec. 25, 2006 | (JP) | 2006-347544 |

(51) Int. Cl.
*C07K 16/00* (2006.01)
*A61K 39/395* (2006.01)

(52) U.S. Cl. ............... 530/388.1; 530/391.1; 530/391.3; 530/388.8; 530/388.85; 530/391.7; 424/141.1; 424/155.1; 424/156.1

(58) Field of Classification Search .............. 424/1.49, 424/9.4, 141.1; 530/388.1, 391.1, 391.3
See application file for complete search history.

(56) References Cited

U.S. PATENT DOCUMENTS

2011/0097261 A1* 4/2011 Janatpour ............... 424/1.49

FOREIGN PATENT DOCUMENTS

| WO | WO 2004/003165 A2 | 1/2004 |
| WO | WO 2004/003165 A3 | 1/2004 |
| WO | WO 2004/055055 A1 | 7/2004 |

OTHER PUBLICATIONS

Steplewski et al. (Proc. Natl. Acad. Sci. USA, 1988, 85: 4852-4856).*
Dillman et al.( Annals of Internal Medicine 1989, 111:592-603).*
Rabenau, K. et al., "DEGA/AMIGO-2, A Leucine-Rich Repeat Family Member, Differentially Expressed in Human Gastric Adenocarcinoma: Effects on Ploidy, Chromosomal Stability, Cell Adhesion/Migration and Tumorigenicity", Oncogene, vol. 23, No. 29, pp. 5056-5067 (2004).
Sunamura, M., "Bunshi Seibutsugakuteki Shuho Ni Yoru Suigan Akuseido Shindan to Bunshi Hyoteki Chiryo No Kalhatsu", Journal of Japan Surgical Society, vol. 106, p. 261 (2005) SF5308-3 (with partial English translation).
Imai, Y., "Proteome Kaiseki No Shuho O Mochiita Suigan Shinki Shuyo Marker No Tansaku" Annual Meeting of the Japan Cancer Association Kiji, vol. 64th, pp. 487 (2005) PA3-1182 (with partial English translation).
Okura, H., "Suigan Shuyo Marker No Combination Assay No Yuyosei", Sogo Rinsho, vol. 39, No. 12, pp. 2781-2786 (1990) (with partial English translation).
Maekawa, M., "Suigan No Soki Eno Approach Suigan No Shuyo Marker", The Journal of Japan Pancreas Society, vol. 19, No. 6, pp. 579-583 (2004) (with partial English translation).
Soyama, N., "Monoclonal Kotal O Mochiita Suigan Soki Shindan to Chiryo Seiseki Kojo No Tameno Rinshoteki Jikkenteki Kenkyu", Medicina Philosophica, vol. 10, No. 2, pp. 73-75 (1991) (with partial English translation).
Juha Kuja-Panula, et al., "AMIGO, a Transmembrane Protein Implicated in Axon Tract Development, Defines a Novel Protein Family with Leucine-Rich Repeats", The Journal of Cell Biology, vol. 160, No. 6, Mar. 17, 2003, pp. 963-973.

\* cited by examiner

*Primary Examiner* — Peter J Reddig
*Assistant Examiner* — Yan Xiao
(74) *Attorney, Agent, or Firm* — Oblon, Spivak, McClelland, Maier & Neustadt, L.L.P.

(57) ABSTRACT

The present invention provides a novel diagnostic or therapeutic method for pancreatic cancer employing a blood marker. The present invention provides a diagnostic or therapeutic drug for pancreatic cancer containing an anti-AMIGO2 antibody.

29 Claims, 13 Drawing Sheets

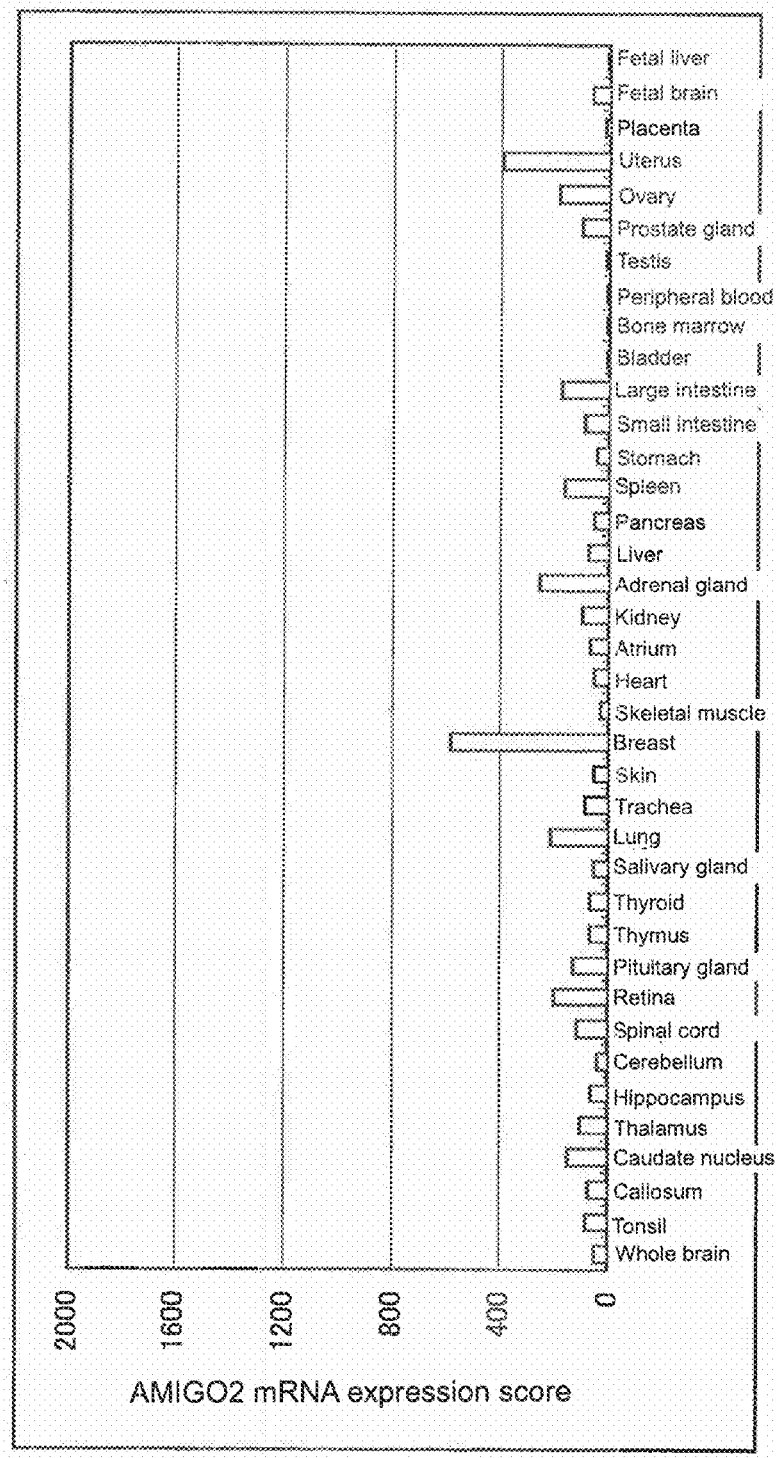
Fig. 1-a

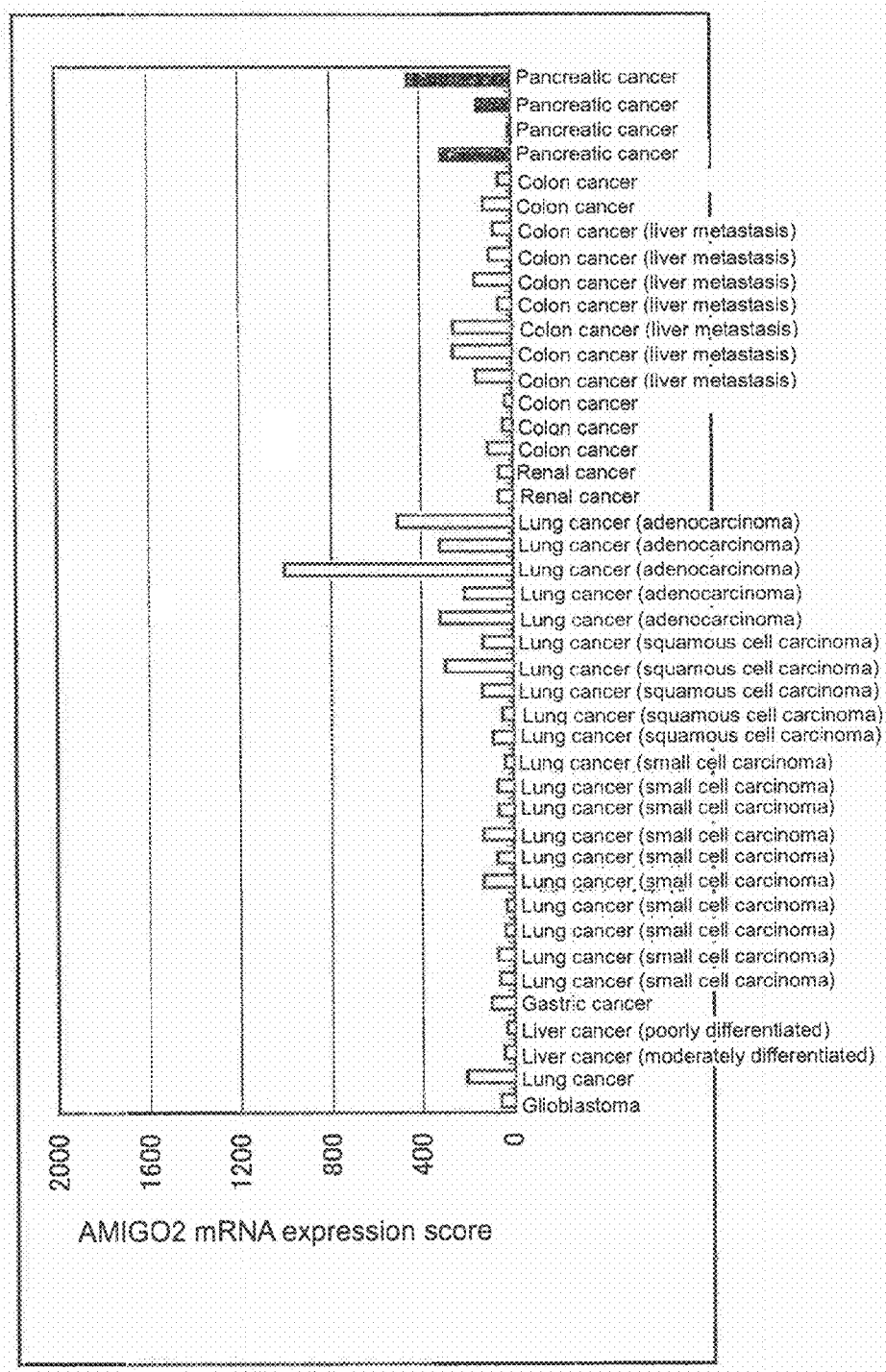
Fig. 1-b

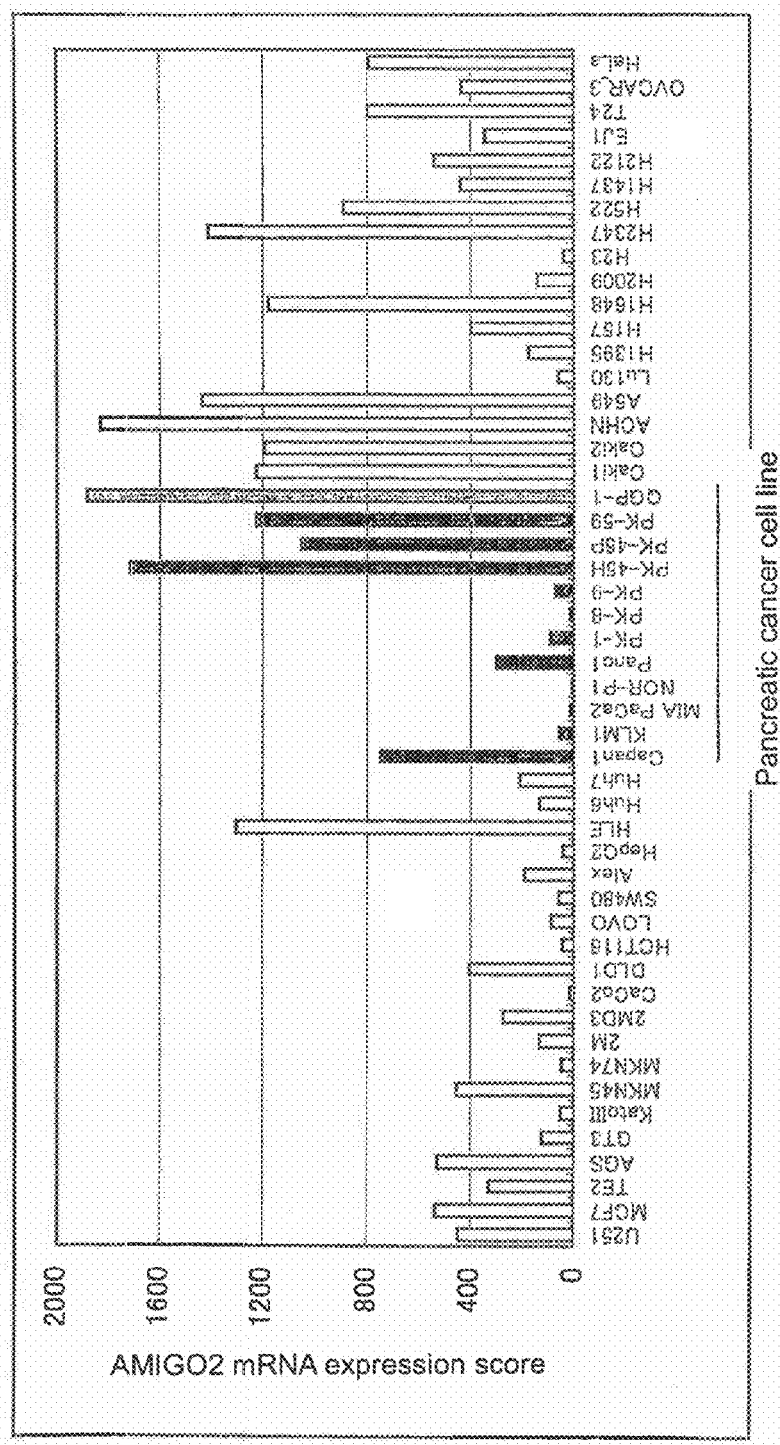
Fig. 1-c

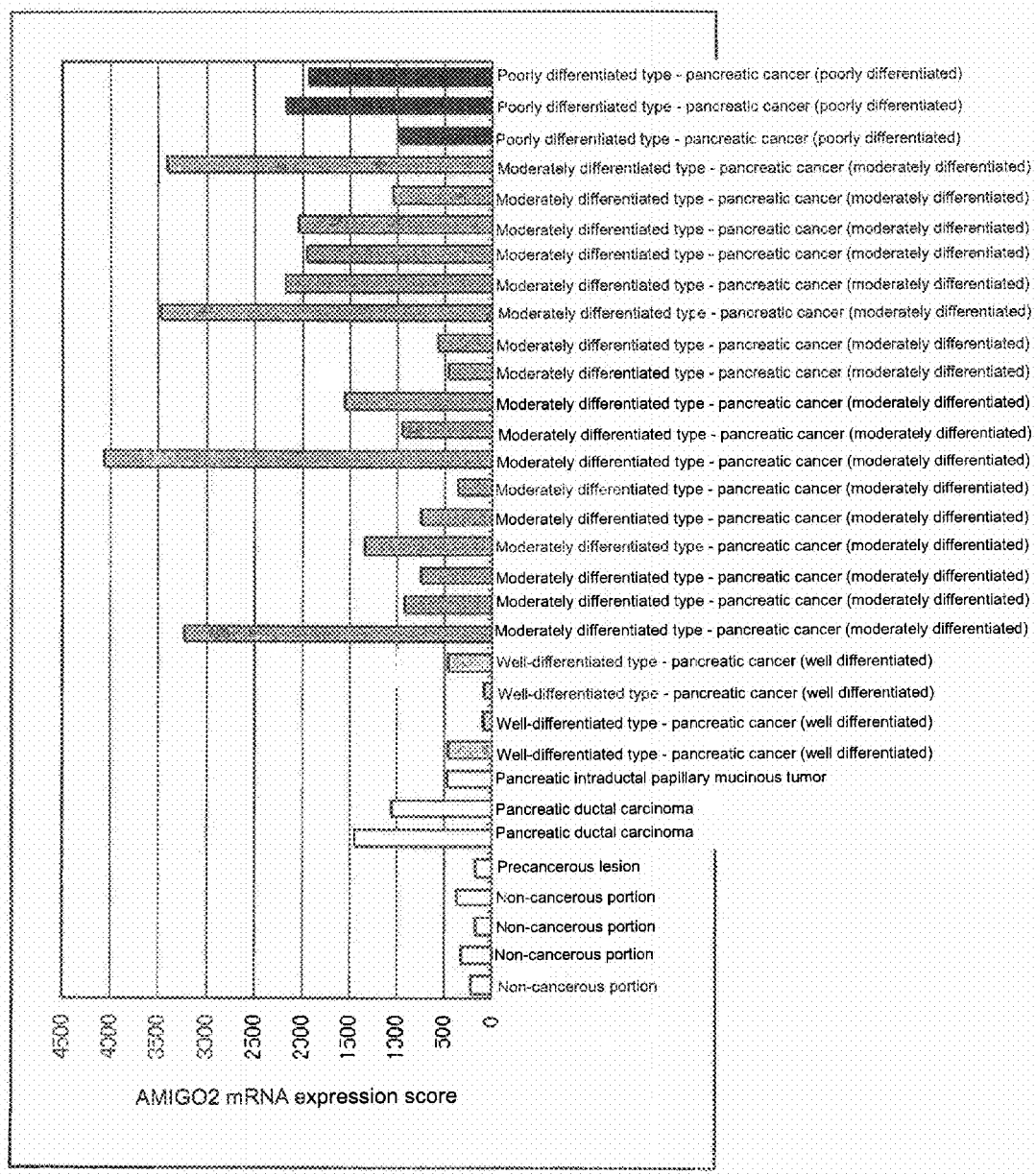

Fig. 16
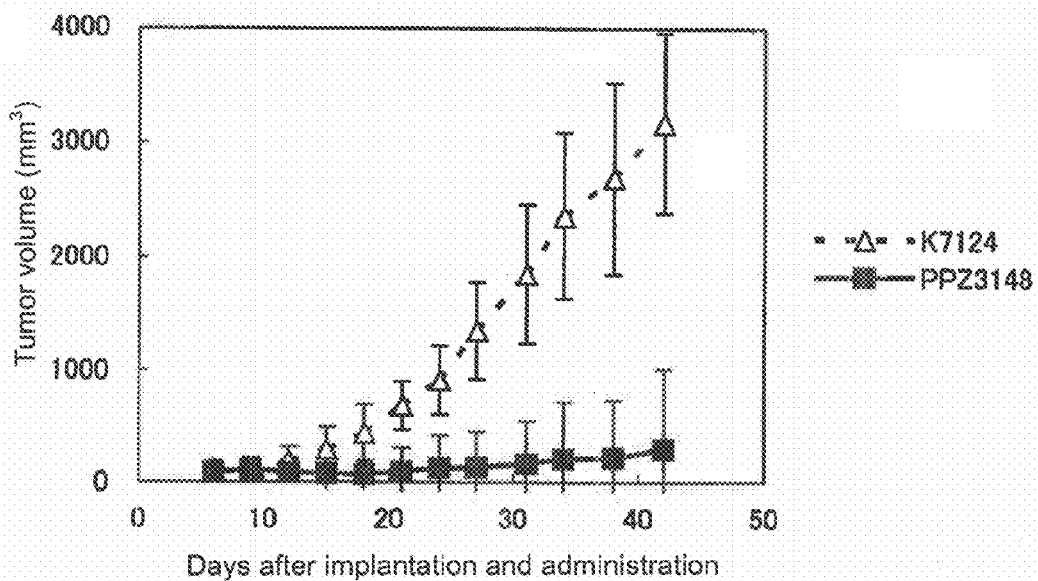
Fig. 17
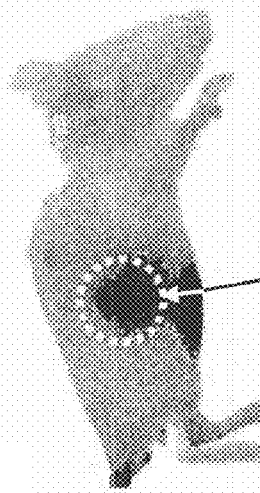
PPZ3124
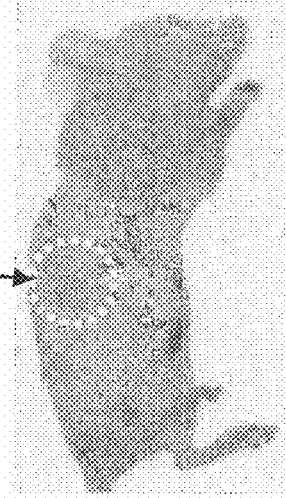
K7124
Site where tumor is present

DIAGNOSTIC AGENT AND THERAPEUTIC AGENT FOR PANCREATIC CANCER

CROSS-REFERENCE TO RELATED APPLICATIONS

The present application is a divisional of U.S. patent application Ser. No. 12/297,759, filed on Oct. 20, 2008, which is a 35 U.S.C. §371 National Stage patent application of International patent application PCT/JP2007/00423, filed on Apr. 18, 2007, which claims priority to Japanese patent applications JP 2006-347544, filed on Dec. 25, 2006, JP 2006-291091, filed on Oct. 26, 2006, and JP 2006-114134, filed on Apr. 18, 2006.

TECHNICAL FIELD

The present invention relates to a diagnostic or therapeutic drug for pancreatic cancer, the drug containing an anti-AMIGO2 antibody.

BACKGROUND ART

In Japan, the number of patients with pancreatic cancer has tended to increase year by year, and the number of deaths from pancreatic cancer was about 20,000 in 2001. Pancreatic cancer is ranked fifth among cancer deaths in men, and sixth among cancer deaths in women. Pancreatic cancer has poor prognosis, and the five-year survival rate of resected cases is 5 to 20%. Poor prognosis of pancreatic cancer is due to the fact that, in many cases, even a small cancer lesion (about 2 cm) invades organs outside of the pancreas, and metastasizes to the liver. Therefore, early diagnosis is very important for pancreatic cancer. However, there has not yet been provided a method for diagnosing pancreatic cancer before invasion thereof into organs surrounding the pancreas.

According to a nation-wide survey in Japan, the greatest number of pancreatic cancer cases is first detected through CT (44%), followed by ultrasonography (41%). Therefore, these two examination techniques are currently important for the diagnosis of pancreatic cancer. However, in the case of CT, which presently widely employed, cancer tissue and noncancerous tissue are difficult to differentiate from each other, and diagnosis requires skilled experts. Examples of tumor markers for pancreatic cancer include CA19-9, DUPAN-2, Span-1, and CEA. Any of these markers shows positive in advanced cancer, but is not useful for early diagnosis of cancer, due to its low probability for diagnosis of early cancer. Furthermore, it has been known that CA19-9 is not suitable for use in diagnosis of pancreatic cancer, since blood CA19-9 level increases in the case of nonmalignancies (e.g., hepatitis, cirrhosis, or pancreatitis).

FDG-PET is also used for diagnosis of pancreatic cancer, but poses problems in terms of, for example, high examination cost and poor image resolution. Therefore, in view of the cost-effectiveness and performance of PET examination, demand has arisen for development of a probe which specifically recognizes pancreatic cancer tissue, as well as a method for diagnosing pancreatic cancer with high accuracy.

Pancreatic cancer is treated through surgery, chemotherapy, or radiotherapy. Among all pancreatic cancer cases, resectable cases account for 40% or less. In addition, the postoperative five-year survival rate is very low (5 to 20%). In the case of pancreatic cancer, surgery often causes problematic complications. Most pancreatic cancer cases detected through local progress or distant metastasis are not treated with surgery, but are treated with chemotherapy or radiotherapy. In recent years, pancreatic cancer cases have been increasingly treated with radiotherapy, since radiotherapy imposes less burden on the gastrointestinal tract and can also be applied to outpatients.

In view of the foregoing, demand has arisen for a new marker for diagnosis of pancreatic cancer, which realizes convenient and accurate examination for pancreatic cancer. In addition, demand has arisen for development of non-invasive and effective therapeutic means for pancreatic cancer; i.e., a therapeutic drug which causes damage specifically to pancreatic cancer cells.

In recent years, there have been actively developed methods for diagnosing or treating cancer by targeting a protein which is expressed specifically in cancer cells; i.e., methods for diagnosing or treating cancer, which employ a sample such as blood or tissue, and which target a cell surface protein that is highly expressed in cancer cells but is less expressed or not expressed in normal tissue. Diagnostic or therapeutic drugs (e.g., Herceptin) have already been provided in the clinical setting, and have contributed to treatment of many cancer patients. Furthermore, demand has arisen for the development of a cancer-specific therapeutic drug in a broad range of cancers.

AMIGO2 is very similar to AMIGO1 and AMIGO3 (which belong to the same family as AMIGO2) in terms of number of amino acids, domain, and gene sequence homology. All of these AMIGO proteins are single-transmembrane proteins, and have a signal peptide. This suggests that AMIGO2 protein is a membrane protein and is possibly secreted into blood. AMIGO family proteins have a similar structure; specifically, each of the proteins has six extracellular leucine-rich repeats (LRRs) and has an LRR amino-terminal domain and an LRR carboxyl-terminal domain such that the six LRR domains are provided therebetween. Each AMIGO family protein also has an immunoglobulin domain in the vicinity of an extracellular transmembrane domain. As has been suggested, AMIGO family proteins are expressed in nerve tissue and function as cell adhesion molecules (Non-Patent Document 1).

Patent Documents 1 and 2 describe that the AMIGO2 gene is highly expressed in gastric cancer, thyroid cancer, breast cancer, uterine cancer, renal cancer, lung cancer, colon cancer, or brain tumor, and that there is no difference in expression level of the AMIGO2 gene between pancreatic cancer and normal tissue. These documents describe that, in Examples in which antibodies are used, AMIGO protein expression associated with differentiation and progress in the rat fetal brain is confirmed through immunostaining, immunoprecipitation, or western blotting, but do not specifically describe that an anti-AMIGO2 antibody can be used for diagnosis or treatment of cancer.

Non-Patent Document 1: J. Cell Biol. 2003 Mar. 17; 160 (69): 963-73
Patent Document 1: WO 2004/003165 pamphlet
Patent Document 2: WO 2004/055055 pamphlet

DISCLOSURE OF THE INVENTION

Problems to be Solved by the Invention

Similar to the cases of cancers other than pancreatic cancer, prognosis of pancreatic cancer depends on the early treatment thereof, and thus pancreatic cancer must be diagnosed at an early stage. However, there has not yet been provided a technique for early diagnosis of pancreatic cancer. Surgical treatment of pancreatic cancer encounters difficulty in treating metastatic focus and often involves both invasion and complications. Radiotherapy of pancreatic cancer causes a problem in terms of radiation exposure to healthy tissue.

The present invention provides a method for diagnosing early pancreatic cancer with high accuracy. The present invention also provides a method for effective treatment of early pancreatic cancer.

Means for Solving the Problems

Studies conducted in the past have reported that expression of the AMIGO2 gene is not detected in pancreatic cancer tissue. However, unexpectedly, the present inventors have found, through gene expression analysis employing DNA microarray, that the expression level of the AMIGO2 gene in pancreatic cancer tissue is higher than that in normal pancreatic tissue. Furthermore, the present inventors have prepared antibodies against AMIGO2 protein and have selected antibodies which meet the below-described uses.

1) AMIGO2 protein released in an extract or culture liquid of pancreatic cancer cells was successfully detected by use of anti-AMIGO2 monoclonal antibodies (antibodies derived from PPZ3122 and PPZ3133) selected for an ELISA system.

2) By use of anti-AMIGO2 monoclonal antibodies (antibodies derived from PPZ2913, PPZ2952, and PPZ3130) selected for immunostaining, AMIGO2 protein was found to be positive in about 83% of pancreatic cancer tissues collected from pancreatic cancer patients.

3) Anti-AMIGO2 monoclonal antibodies (antibodies derived from PPZ2919, PPZ2952, PPZ3122, PPZ3124, PPZ3135, and PPZ3148) were selected as antibodies which favorably affect cell growth.

4) When these anti-AMIGO2 monoclonal antibodies were administered to a full-length-AMIGO2-expressing CHO clone or pancreatic cancer cells PK-45P in an in vitro test, the antibodies exhibited CDC activity and/or ADCC activity, which are indexes of cytotoxic activity.

5) In an in vivo test employing scid mice, an anti-AMIGO2 antibody inhibited engraftment or growth in mice of the pancreatic cancer cells PK-45P or an AMIGO2-forcedly-expressing pancreatic cancer cell line MIA PaCa2.

6) An anti-AMIGO2 antibody labeled with a fluorescent substance was administered to scid mice bearing the pancreatic cancer cells PK-45P, and the anti-AMIGO2 antibody was found to be accumulated in tumor mass through in vivo fluorescence imaging.

7) A cytotoxic substance was found to exhibit a cell growth inhibitory effect by being incorporated into cells through endocytosis via an anti-AMIGO2 antibody bound to AMIGO2 present on the cell surfaces.

The present invention has been accomplished on the basis of the aforementioned findings 1) to 7).

That is, the present invention provides a diagnostic or therapeutic drug for pancreatic cancer containing an anti-AMIGO2 antibody.

The present invention also provides use of an anti-AMIGO2 antibody for producing a diagnostic drug for pancreatic cancer.

The present invention also provides use of an anti-AMIGO2 antibody for producing a therapeutic drug for pancreatic cancer.

The present invention also provides a method for diagnosing pancreatic cancer, characterized by comprising reacting an anti-AMIGO2 antibody with a sample collected from a subject, or administering the anti-AMIGO2 antibody to the subject; and detecting possible AMIGO2 protein.

The present invention also provides a method for treatment of pancreatic cancer, characterized by comprising administering an anti-AMIGO2 antibody to a subject in need thereof.

Effects of the Invention

Positron emission tomography employing, as a probe, a glucose analogue labeled with a positron-emitting radionuclide (FDG-PET), which is a conventionally used typical diagnostic imaging technique for cancer, often produces false-positive or false-negative results in early diagnosis of pancreatic cancer.

The present invention realizes diagnosis (biopsy) of pancreatic cancer employing molecular imaging (PET) for specifically detecting AMIGO2 protein; or diagnosis of pancreatic cancer employing blood or tissue collected by biopsy. Therefore, according to the present invention, a new therapeutic regimen can be established promptly. In addition, the present invention realizes non-invasive pancreatic cancer treatment which requires no surgery and imposes less burden on patients.

BRIEF DESCRIPTION OF THE DRAWINGS

FIG. 1-*a* shows the results of AMIGO2 gene expression analysis by means of GeneChip U133: AMIGO2 gene expression analysis in normal tissue (non-cancerous portions).

FIG. 1-*b* shows the results of AMIGO2 gene expression analysis by means of GeneChip U133: AMIGO2 gene expression analysis in clinical samples.

FIG. 1-*c* shows the results of AMIGO2 gene expression analysis by means of GeneChip U133: AMIGO2 gene expression analysis in cancer cell lines.

FIG. 2 shows the results of AMIGO2 gene expression analysis in clinical pancreatic cancer samples by means of GeneChip U133 plus 2.

FIG. 16 shows the results of evaluation of the tumor growth inhibitory effect of an anti-AMIGO2 monoclonal antibody (PPZ3148-derived antibody) in scid mice implanted with the AMIGO2-forcedly-expressing pancreatic cancer cell lines.

FIG. 17 shows the results of determination, through in vivo fluorescence imaging, of accumulation of an anti-AMIGO2 monoclonal antibody in tumor formed by implantation of pancreatic cancer cell lines in a scid mouse.

BEST MODES FOR CARRYING OUT THE INVENTION

Figure 3:
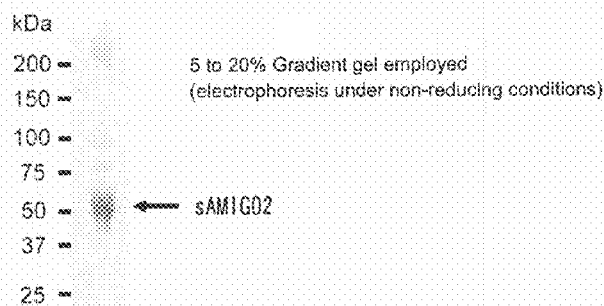
FIG. 3 shows the results of non-reducing SDS-PAGE analysis of purified sAMIGO2.

The disease diagnosed or treated by the method of the present invention is pancreatic cancer. The animal intended to be diagnosed or treated is preferably human, but may be a mammal such as dog, cat, rabbit, mouse, rat, or guinea pig.

In the case where pancreatic cancer is diagnosed by the method of the present invention, when AMIGO2 protein is detected in blood or organ tissue from a subject, the subject is determined to have a high likelihood of developing pancreatic cancer. When the level of AMIGO2 protein in blood or tissue from a patient who has been diagnosed to have pancreatic cancer is measured, it can be determined whether or not the patient is to be treated (selection of a patient to be treated). In the case where the AMIGO2 protein level of a patient is measured after the treatment of pancreatic cancer, when the AMIGO2 protein level is lower than that measured before surgery, therapeutic prognosis is determined to be good, whereas when the AMIGO2 protein level is not lower (or is higher) than that measured before surgery, recurrence or metastasis is determined to occur. Diagnosis of pancreatic cancer may be carried out through diagnostic imaging, biopsy, or hemodiagnosis.

Diagnostic imaging may be carried out by administering a labeled anti-AMIGO2 antibody to a subject, followed by detection of AMIGO2 protein through imaging. More specifically, a probe prepared by labeling an anti-AMIGO2 antibody with a radioisotope as a labeling substance is administered to a subject, and cancer tissue may be detected through PET or SPECT. The radioisotope employed may be any radioisotope known to those skilled in the art, but is preferably a positron-emitting radioisotope, more preferably $^{11}$C, $^{13}$N, $^{18}$F, $^{15}$O, $^{94m}$Tc, or $^{124}$I. Labeling of an anti-AMIGO2 antibody with a radioisotope may be carried out through a method known to those skilled in the art.

In a mode of diagnosis of pancreatic cancer by biopsy, an immunological assay may be carried out by using, as a sample, organ tissue obtained from a subject. Examples of the immunological assay include radioimmunoassay, enzyme immunoassay, fluoroimmunoassay, luminescence immunoassay, immunoprecipitation, immunonephelometry, western blotting, immunostaining, and immunodiffusion. Preferably, immunostaining is employed. The aforementioned immunological methods (e.g., immunostaining) may be carried out through techniques known to those skilled in the art.

In another mode of diagnosis of pancreatic cancer by biopsy, immunohistological staining may be carried out by use of an anti-AMIGO2 antibody as a primary antibody. Specifically, a sample obtained from a subject is fixed through a known technique (e.g., paraffin embedding or freezing), to thereby prepare sections. Subsequently, each section is treated with an anti-AMIGO2 antibody (i.e., a primary antibody) and with a biotin-labeled antibody which recognizes IgG (i.e., a secondary antibody). The secondary antibody may be a known antibody which recognizes IgG; for example, rabbit anti-IgG antibody. A labeling substance is bound to the secondary antibody, and the presence or absence of AMIGO2 protein in the section is detected through a known method suitable for the labeling substance. Alternatively, immunohistological staining may be carried out by binding a labeling substance to the anti-AMIGO2 antibody without use of the secondary antibody. The labeling substance may be any substance known to those skilled in the art; for example, peroxidase or FITC. Binding between the antibody and the labeling substance may be carried out through a method known to those skilled in the art; specifically, a binding method employing streptavidin and biotin.

In another mode of diagnosis of pancreatic cancer, an immunological assay may be carried out by using, as a sample, blood, serum, or plasma obtained from a subject. Examples of the immunological assay include radioimmunoassay, enzyme immunoassay, fluoroimmunoassay, luminescence immunoassay, immunoprecipitation, immunonephelometry, western blotting, and immunodiffusion. Enzyme immunoassay is preferred, with enzyme-linked immunosorbent assay (ELISA) (e.g., sandwich ELISA) being particularly preferred. The aforementioned immunological methods (e.g., ELISA) may be carried out through techniques known to those skilled in the art.

Diagnosis of pancreatic cancer by using, as a test sample, blood, serum, or plasma may be carried out through, for example, the following procedure: an anti-AMIGO2 antibody is immobilized on a support, and the test sample is added thereto; the anti-AMIGO2 antibody is caused to be bound to AMIGO2 protein through incubation, followed by washing; and the AMIGO2 protein which has been bound to the support via the anti-AMIGO2 antibody is detected.

Examples of the support which may be employed for immobilization of an anti-AMIGO2 antibody in the present invention include insoluble polysaccharides such as agarose and cellulose; synthetic resins such as silicone resin, polystyrene resin, polyacrylamide resin, nylon resin, and polycarbonate resin; and insoluble supports such as glass and ferrite. Such a support may be employed in the form of, for example, beads or plate. In the case where the support is in the form of beads, for example, a column charged with support beads may be employed. In the case where the support is in the form of plate, for example, a multiwell plate (e.g., a 96-well plate) or a biosensor chip may be employed. Binding between an anti-AMIGO2 antibody and a support may be carried out through a generally employed technique such as chemical binding or physical adsorption. The aforementioned supports may be commercially available ones.

Binding between an anti-AMIGO2 antibody and AMIGO2 protein contained in a sample is generally carried out in a buffer. Examples of the buffer employed include phosphate buffer, Tris buffer, citrate buffer, borate buffer, and carbonate buffer. No particular limitation is imposed on the pH, so long as it falls within a generally used range. Incubation is carried out under generally used conditions (e.g., 4° C. to 37° C., 1 hour to 24 hours). No particular limitation is imposed on the substance employed for washing after incubation, so long as it does not impede binding between the anti-AMIGO2 antibody and AMIGO2 protein. For example, a buffer containing a surfactant (e.g., Tween-20) is employed.

In the method for detecting AMIGO2 protein of the present invention, a control sample may be provided in addition to a test sample employed for detection of AMIGO2 protein. The control sample may be, for example, a negative control sample containing no AMIGO2 protein, or a positive control sample containing AMIGO2 protein. In such a case, AMIGO2 protein contained in the test sample may be detected through comparison with the results obtained from a negative control sample containing no AMIGO2 protein, or the results obtained from a positive control sample containing AMIGO2 protein. Alternatively, the amount of AMIGO2 protein contained in the test sample may be quantitatively determined through the following procedure: preparing a series of control samples in which AMIGO2 concentrations are varied stepwise, preparing a standard curve by obtaining the detection result of each control sample as numeric value, and quantitatively determining the amount of AMIGO2 protein contained in the test sample, based on the standard curve from a measurement of the test sample.

A preferred mode of the method for detecting AMIGO2 protein bound to a support via an anti-AMIGO2 antibody is a method employing an anti-AMIGO2 antibody labeled with a labeling substance. For example, a test sample is exposed to an anti-AMIGO2 antibody immobilized on a support, followed by washing, and subsequently AMIGO2 protein is detected by use of a labeled antibody which specifically recognizes the AMIGO2 protein.

Labeling of an anti-AMIGO2 antibody may be carried out through a generally known method. Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}P$, $^{14}C$, $^{125}I$, $^{3}H$, and $^{131}I$), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Binding between a labeling substance and an anti-AMIGO2 antibody may be carried out through a known method such as the glutaraldehyde method, the maleimide method, the pyridyl disulfide method, or the periodate method.

Specifically, a solution containing an anti-AMIGO2 antibody is added to a support (e.g., a plate or beads), to thereby immobilize the anti-AMIGO2 antibody on the support. After washing of the plate or beads, the antibody is blocked with, for example, BSA, gelatin, or albumin, in order to prevent non-specific protein binding. The plate or beads are washed again, and a test sample is added to the plate or beads, followed by incubation. Subsequently, the plate or beads are washed, and a labeled anti-AMIGO2 antibody is added, followed by appropriate incubation. Thereafter, the plate or beads are washed, and the labeled anti-AMIGO2 antibody remaining on the support is detected. This detection may be carried out through a method known to those skilled in the art.

For example, in the case where the anti-AMIGO2 antibody is labeled with a radioactive substance, detection is performed through the liquid scintillation or RIA method. In the case where the anti-AMIGO2 antibody is labeled with an enzyme, a substrate is added, and enzymatic change of the substrate (e.g., coloring) is detected by means of an absorbance meter. Specific examples of the substrate which may be employed include 2,2-azinobis(3-ethylbenzothiazoline-6-sulfonic acid)diammonium salt (ABTS), 1,2-phenylenediamine(o-phenylenediamine), and 3,3',5,5'-tetramethylbenzidine (TMB). In the case where the anti-AMIGO2 antibody is labeled with a fluorescent substance or a chemiluminescent substance, detection is performed by means of a luminometer.

A particularly preferred mode of the method for detecting AMIGO2 protein of the present invention is a method employing a biotin-labeled anti-AMIGO2 antibody and streptavidin.

Specifically, a solution containing an anti-AMIGO2 antibody is added to a support (e.g., a plate), to thereby immobilize the anti-AMIGO2 antibody on the support. After washing of the plate, the antibody is blocked with, for example, BSA, in order to prevent non-specific protein binding. The plate is washed again, and a test sample is added to the plate, followed by incubation. Thereafter, the plate is washed, and a biotin-labeled anti-AMIGO2 antibody is added, followed by appropriate incubation. Thereafter, the plate is washed, and avidin bound to an enzyme (e.g., alkaline phosphatase or peroxidase) is added, followed by incubation. Thereafter, the plate is washed, and a substrate corresponding to the enzyme bound to avidin is added, followed by detection of AMIGO2 protein on the basis of, for example, enzymatic change of the substrate.

Another mode of the method for detecting AMIGO2 protein of the present invention is a method employing one or more primary antibodies which specifically recognize AMIGO2 protein, and one or more secondary antibodies which specifically recognize the primary antibodies.

For example, a test sample is exposed to one or more anti-AMIGO2 antibodies immobilized on a support, followed by incubation. Subsequently, the support is washed, and then AMIGO2 protein bound to the antibodies is detected by use of one or more primary anti-AMIGO2 antibodies and one or more secondary antibodies which specifically recognize the primary antibodies. In this case, preferably, the secondary antibodies are labeled with a labeling substance.

Another mode of the method for detecting AMIGO2 protein of the present invention is a detection method employing aggregation reaction. In this method, AMIGO2 protein can be detected by use of a carrier sensitized with an anti-AMIGO2 antibody. No particular limitation is imposed on the carrier which is sensitized with the antibody, so long as the carrier is insoluble, does not cause non-specific reaction, and is stable. For example, latex particles, bentonite, collodion, kaolin, or immobilized sheep erythrocyte may be employed. However, preferably, latex particles are employed. Examples of the latex particles which may be employed include polystyrene latex particles, styrene-butadiene copolymer latex particles, and polyvinyl toluene latex particles. Preferably, polystyrene latex particles are employed. The thus-sensitized particles are mixed with a sample, and the resultant mixture is stirred for a predetermined period of time. The higher the level of AMIGO2 protein contained in the sample, the greater the degree of aggregation of the particles. Therefore, AMIGO2 protein can be detected through visual observation of the particle aggregation. Alternatively, AMIGO2 protein may be detected by measuring the degree of turbidity corresponding to the particle aggregation by means of, for example, a spectrophotometer.

Another mode of the method for detecting AMIGO2 protein of the present invention is a method employing, for example, a biosensor utilizing surface plasmon resonance phenomenon. A biosensor utilizing surface plasmon resonance phenomenon realizes real-time observation of protein-protein interaction in the form of surface plasmon resonance signal by use of a very small amount of protein without labeling. For example, binding between an anti-AMIGO2 antibody and AMIGO2 protein may be detected by means of a biosensor such as BIAcore (product of Biacore International AB). Specifically, a test sample is exposed to a sensor chip on which an anti-AMIGO2 antibody has been immobilized, and AMIGO2 protein which is bound to the anti-AMIGO2 antibody may be detected on the basis of change in surface plasmon resonance signal.

The detection method of the present invention may be automated by means of a variety of automatic test systems, whereby a large number of samples can be tested in a single operation.

The diagnostic drug for pancreatic cancer of the present invention may be in the form of a kit. The diagnostic drug for pancreatic cancer of the present invention contains at least an anti-AMIGO2 antibody. When the diagnostic drug is employed in EIA (e.g., ELISA), the drug may contain a carrier for immobilizing the antibody, or the antibody may be bound to the carrier in advance. When the diagnostic drug is employed in the aggregation method employing a carrier such as latex, the drug may contain a carrier onto which the antibody has been adsorbed. The diagnostic drug may appropriately contain, for example, a blocking solution, a reaction solution, a reaction-terminating liquid, or a reagent for treating a sample.

No particular limitation is imposed on the origin, type (monoclonal or polyclonal), and form of an anti-AMIGO2 antibody employed in the present invention for diagnosing pancreatic cancer by detecting AMIGO2 protein in a sample (e.g., biopsy tissue or blood), so long as the antibody binds specifically to AMIGO2 protein. Specifically, the anti-AMIGO2 antibody may be a known antibody such as mouse antibody, rat antibody, avian antibody, human antibody, chimeric antibody, and humanized antibody. The anti-AMIGO2 antibody may be a monoclonal antibody, but is preferably a polyclonal antibody. The anti-AMIGO2 antibody may be a commercially available antibody, so long as it exhibits high sensitivity and realizes specific assay.

An anti-AMIGO2 antibody immobilized on a support and an anti-AMIGO2 antibody labeled with a labeling substance may recognize the same epitope of AMIGO2 protein. However, preferably, these antibodies recognize different epitopes of AMIGO2 protein. No particular limitation is imposed on the site of such an epitope.

When pancreatic cancer is treated through the method of the present invention, an anti-AMIGO2 antibody is bound specifically to AMIGO2 protein expressed in pancreatic cancer cells, to thereby cause damage to pancreatic cancer cells. Damage to pancreatic cancer cells may be caused by the cytotoxic activity of the anti-AMIGO2 antibody (e.g., ADCC activity or CDC activity).

No particular limitation is imposed on the antibody employed in the present invention for the treatment or diagnostic imaging of pancreatic cancer, so long as it binds specifically to AMIGO2 protein. The antibody may be a chimeric antibody, a humanized (CDR-grafted) antibody, or a human antibody, so long as it is a monoclonal antibody. The antibody may be a commercially available antibody, so long as it has a therapeutic effect on pancreatic cancer. The antibody is preferably an antibody exhibiting cytotoxic activity. The antibody employed in the present invention may be a sugar-chain-modified antibody. The cytotoxic activity of the antibody can be enhanced through modification of the sugar chain thereof. No particular limitation is imposed on the antibody employed for the treatment of pancreatic cancer, so long as it has an anticancer effect. Thus, the antibody may be an antibody to which a substance having an antitumor effect has been bound. Pancreatic cancer can be treated by use of a monoclonal antibody to which a drug having an antitumor effect or a radioisotope has been bound.

As used herein, "cytotoxic activity" refers to, for example, antibody-dependent cell-mediated cytotoxicity (ADCC) activity, or complement-dependent cytotoxicity (CDC) activity. As used herein, "CDC activity" refers to an cytotoxic activity mediated by a complement system; and "ADCC activity" refers to an activity to cause damage to a target cell when a specific antibody binds to a surface antigen of the target cell, and an Fcγ-receptor-containing cell (e.g., immunocyte) binds to the Fc portion of the antibody via the Fcγ receptor.

Whether or not an anti-AMIGO2 antibody has ADCC activity or CDC activity may be determined through a known method. Examples of hitherto reported methods include a method employing, as an index, release of $^{51}Cr$ (i.e., a radioactive substance) which has been incorporated into a target cell in advance [e.g., Martin R., et al. (1990) Fine specificity and HLA restriction of myelin basic protein-specific cytotoxic T cell lines from multiple sclerosis patients and healthy individuals. J. Immunol. 145, 540]; a method employing, as an index, release of calcein (i.e., a fluorescent substance) which has been incorporated into a target cell in advance [e.g., Lichtenfels R., et al. (1994) CARE-LASS (calcein-release-assay), an improved fluorescence-based test system to measure cytotoxic T lymphocyte activity. J. Immunol. Methods 172, 227]; and a method employing, as an index, release of lactate dehydrogenase (LDH) contained in a target cell [e.g., Korzeniewski C. and Callewaert DM. (1983) An enzyme-release assay for natural cytotoxicity. J. Immunol. Methods 64, 313].

Specifically, firstly, an effector cell, a complement solution, and a target cell are prepared.

(1) Preparation of an Effector Cell

The spleen is removed from, for example, each BALB/c mouse, and spleen cells are isolated in an RPMI 1640 medium (product of Invitrogen). Spleen cells are washed with an RPMI 1640 medium containing 5 to 10% fetal bovine serum (FBS), and the cell concentration is regulated to $5\times10^6$/mL, whereby effector cells are prepared.

(2) Preparation of a Complement Solution

Baby Rabbit Complement (product of CEDARLANE) is appropriately diluted with an RPMI 1640 medium (product of Invitrogen) containing 5 to 10% FBS, to thereby prepare a complement solution.

(3) Preparation of a Target Cell

AMIGO2-expressing cells (i.e., cells transformed with the AMIGO2-encoding gene, or pancreatic cancer cells) are provided. In the case where cytotoxic activity is determined through a method employing, as an index, release of $^{51}Cr$ (i.e., a radioactive substance) which has been incorporated into a target cell in advance, the target cell is prepared through the following procedure: cells of an AMIGO2-expressing cell line are cultured with 0.2 mCi $^{51}Cr$-sodium chromate (product of GE Healthcare Bioscience) in a 10% FBS-containing DMEM medium at 37° C. for one hour, to thereby label the cells with the radioactive substance; and the thus-labeled cells are washed three times with a 10% FBS-containing DMEM medium, followed by regulation of the cell concentration to $2\times10^5$/mL.

In the case where cytotoxic activity is determined through a method employing, as an index, release of a fluorescent substance which has been incorporated into a target cell in advance, the target cell is prepared through the following procedure: AMIGO2-expressing cells are cultured with 25 µM calcein-AM [3',6'-di(0-acetyl)-4',5'-bis[N,N-bis(carboxymethyl)aminomethyl]fluorescein tetraacetoxymethyl ester] in PBS (phosphate-buffered saline) at 37° C. for 30 minutes, to thereby label the cells with the fluorescent substance; and the thus-labeled cells are washed twice with a 5% FBS-containing DMEM medium (containing no Phenol Red), followed by regulation of the cell concentration to $2\times10^5$/mL. In the case where cytotoxic activity is determined through a method employing, as an index, release of lactate dehydrogenase (LDH) contained in target cells, an AMIGO2-expressing cell is employed, as is, as the target cell after regulation of the cell concentration to $2\times10^5$/mL.

Subsequently, ADCC activity or CDC activity is determined. When ADCC activity is determined, a target cell (50 µL) and an anti-AMIGO2 antibody (50 µL) are added to a 96-well U-bottomed plate (product of Becton Dickinson), and the mixture is caused to be reacted on ice for 15 minutes. Thereafter, an effector cell (100 µL) is added to the plate, followed by culturing in a carbon dioxide gas incubator for four hours. After completion of culturing, a supernatant (100 is recovered. When release of $^{51}$Cr is employed as an index, radioactivity is determined by means of a gamma counter (Cobra II Auto-Gamma, Model D5005, product of Packard Instrument Company). Cytotoxic activity (%) can be obtained by the following formula: $(A-C)/(B-C)\times100$ (wherein A represents the radioactivity (cpm) of the above-prepared sample; B represents the radioactivity (cpm) of a sample in which cells are completely lysed through addition of a surfactant (e.g., 1% Triton-X100); and C represents the radioactivity (cpm) of a sample containing only a target cell). When release of calcein (i.e., a fluorescent substance) is employed as an index, fluorescence intensity is determined by means of a fluorescence plate reader (excitation wavelength: 485 nm/fluorescence wavelength: 520 nm). When release of LDH contained in a target cell is employed as an index, red formazan produced from a tetrazolium salt through conjugation coupled reaction between LDH and diaphorase is determined by means of a microplate reader (wavelength: 490 nm).

When CDC activity is determined, a target cell (50 µL) and an anti-AMIGO2 antibody (20 µL) are added to a 96-well U-bottomed plate (product of Becton Dickinson), followed by reaction on ice for 30 minutes. Thereafter, a complement solution (10 µL) is added to the plate, followed by culturing in a carbon dioxide gas incubator for four hours. After completion of culturing, a supernatant (50 µL) is recovered, followed by determination of, for example, radioactivity. Cytotoxic activity can be determined in a manner similar to that in the case of determination of ADCC activity.

An anti-AMIGO2 antibody may also be employed as a therapeutic drug for pancreatic cancer in a missile therapy specifically targeting cancer tissue; specifically, a therapy intended to enhance a therapeutic effect and to reduce side effects, in which an anti-AMIGO2 antibody bound to a drug which causes damage to cancer cells is administered to a subject in need thereof so that the antibody is delivered to cancerous sites in a site-specific manner.

Binding between such a drug and an anti-AMIGO2 antibody may be carried out through a method known to those skilled in the art (Clin. Cancer Res. 2004 Jul. 1; 10 (13): 4538-49). The drug which is bound to the antibody may be any known substance which causes damage to cancer cells. However, the drug is preferably an anticancer agent or a toxin, more preferably calicheamicin, DM1, DM4, ricin, or *Pseudomonas* exotoxin A.

The antibody employed for the treatment of pancreatic cancer may be an antibody which binds specifically to AMIGO2 protein, and which is bound to a radioisotope which causes damage to cancer cells so that the antibody is provided with cytotoxic activity, or the cytotoxic activity of the antibody is enhanced. Binding between such an antibody and such a radioisotope may be carried out through a method known to those skilled in the art (Bioconjug. Chem. 1994 March-April; 5 (2): 101-4). The radioisotope employed may be any radioisotope known to those skilled in the art, but is preferably a nuclide which emits β-ray or α-ray, more preferably $^{132}$I, $^{99m}$Tc, $^{111}$In, or $^{90}$Y.

Pancreatic cancer treatment employing an antibody bound to a radioisotope-containing compound may be carried out through a method known to those skilled in the art (Bioconjug. Chem. 1998 November-December; 9 (6): 773-82). Specifically, firstly, a small amount of an antibody bound to a radioisotope-containing compound is administered to a patient, followed by whole-body scintigraphy. After determination that the degree of binding between the antibody and normal tissue cells is low but the degree of binding between the antibody and cancer cells is high, a large amount of the antibody bound to the radioisotope-containing compound is administered to the patient.

The anti-AMIGO2 antibody employed in the present invention may be obtained as a polyclonal or monoclonal antibody through any known means. The anti-AMIGO2 antibody employed in the present invention is preferably a mammal-derived or avian-derived monoclonal antibody, particularly preferably a mammal-derived monoclonal antibody. The mammal-derived monoclonal antibody includes a monoclonal antibody produced by a hybridoma, and a monoclonal antibody produced in a host transformed with an expression vector containing a gene for the antibody through a genetic engineering technique.

Basically, a hybridoma which produces the monoclonal antibody may be prepared through a known technique as described below. Specifically, the hybridoma may be prepared through the following procedure: a mammal is immunized with AMIGO2 protein serving as a sensitizing antigen through a customary immunization method; the resultant immunocyte is fused with a known parental cell through a customary cell fusion method; and a cell for producing the monoclonal antibody is selected through a customary screening method.

Specifically, the monoclonal antibody can be prepared as follows.

Firstly, AMIGO2 protein, which is employed as a sensitizing antigen for preparing the monoclonal antibody, is obtained through expression of the gene/amino acid sequence disclosed in GenBank number NM 181847 (SEQ ID NO: 1 or 2). Specifically, an appropriate host cell is transformed with a known expression vector system containing the gene sequence encoding AMIGO2 protein, and then human AMIGO2 protein of interest is purified from the resultant host cell or a culture supernatant of the cell through a known method. Alternatively, natural AMIGO2 protein may be employed after being purified.

Subsequently, the thus-purified AMIGO2 protein is employed as a sensitizing antigen. Alternatively, a partial peptide of the AMIGO2 protein may be employed as a sensitizing antigen. Such a partial peptide may be obtained through chemical synthesis on the basis of the amino acid sequence of human AMIGO2 protein, through integration of a portion of the human AMIGO2 gene into an expression vector, or through degradation of natural human AMIGO2 protein by use of protease. No particular limitation is imposed on the site or size of a human AMIGO2 protein portion employed as a partial peptide.

No particular limitation is imposed on the mammal which is immunized with the sensitizing antigen, but preferably, the mammal is selected in consideration of compatibility of the resultant immunocyte with a parental cell employed for cell fusion. In general, a rodent (e.g., mouse, rat, or hamster), avian, rabbit, monkey, or the like is employed.

Immunization of an animal with the sensitizing antigen is carried out through a known method. For example, in a generally employed immunization method, the sensitizing antigen is intraperitoneally or subcutaneously injected in a mammal. Specifically, the sensitizing antigen is diluted and suspended in an appropriate amount of PBS (phosphate-buffered saline), saline, or the like, and, if desired, the resultant suspension is mixed with an appropriate amount of a common adjuvant (e.g., Freund's complete adjuvant). After emulsification of the resultant mixture, the emulsion is administered to a mammal several times every 4 to 21 days. Upon immunization with the sensitizing antigen, an appropriate carrier may be employed. Particularly when a partial peptide having low molecular weight is employed as the sensitizing antigen, preferably, the partial peptide employed for immunization is bound to a carrier protein such as albumin or keyhole limpet hemocyanin.

After immunization of a mammal as described above, and confirmation of an increase in serum level of an antibody of interest, immunocytes are collected from the mammal, and then subjected to cell fusion. The type of immunocytes is particularly preferably splenocyte.

A mammalian myeloma cell is employed as the parental cell which is fused with the aforementioned immunocyte. The myeloma cell employed is preferably a known cell line; for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H., et al., Cell (1976) 8, 405-415), SP2/0 (Shulman, M., at al., Nature (1978) 276, 269-270), FO (de St. Groth, S. F., et al., J. Immunol. Methods (1980) 35, 1-21), S194 (Trowbridge, I. S. J. Exp. Med. (1978) 148, 313-323), or R210 (Galfre, G., et al., Nature (1979) 277, 131-133).

Cell fusion between the aforementioned immunocyte and myeloma cell may be basically carried out through a known method, such as the method of Kohler, Milstein, et al. (Kohler. G. and Milstein, C., Methods Enzymol. (1981) 73, 3-46).

More specifically, the aforementioned cell fusion is carried out in a common nutrient culture medium in the presence of, for example, a cell fusion promoter. Examples of the cell fusion promoter employed include polyethylene glycol (PEG) and Sendai virus (HVJ). If desired, an auxiliary agent (e.g., dimethyl sulfoxide) may be further added in order to enhance cell fusion efficiency.

The amounts of the immunocyte and myeloma cell employed may be determined as desired. For example, the amount of the immunocyte is preferably 1 to 10 times higher than that of the myeloma cell. Examples of the culture medium which may be employed for the aforementioned cell fusion include RPMI 1640 medium and MEM medium, which are suitable for growth of the aforementioned myeloma cell line; and culture media which are generally employed for such a cell culture. Such a culture medium may be employed in combination with a serum supplement such as fetal calf serum (FCS).

In the cell fusion, predetermined amounts of the aforementioned immunocyte and myeloma cell are well-mixed in any of the aforementioned culture media, and a solution of PEG (e.g., PEG having an average molecular weight of about 1,000 to about 6,000) which has been heated in advance to about 37° C. is added to the resultant mixture in a predetermined amount (generally 30 to 600 (w/v)), followed by mixing, to thereby yield a target hybridoma. Subsequently, a procedure (including sequential addition of an appropriate culture medium, and removal of a supernatant obtained through centrifugation) is repeated, to thereby remove substances (e.g., cell fusion promoter) which are not suitable for growth of the hybridoma.

Separation of the thus-yielded hybridoma is carried out through culturing in a common selective culture medium such as HAT medium (medium containing hypoxanthine, aminopterin, and thymidine). The culturing in the aforementioned HAT medium is continued for a sufficient period of time (generally several days to several weeks) for apoptosis of cells (i.e., non-fused cells) other than the target hybridoma. Subsequently, a customary limiting dilution technique is performed for screening and monocloning of the hybridoma which produces a target antibody.

Screening and monocloning of a target antibody may be carried out through a known screening method on the basis of antigen-antibody reaction. For example, an antigen is bound to a carrier (e.g., beads made of polystyrene and the like, or a commercially available 96-well microtiter plate, and the like) and then reacted with a culture supernatant of the hybridoma, and subsequently the carrier is washed, followed by reaction with, for example, an enzyme-labeled secondary antibody, to thereby determine whether or not the culture supernatant contains a target antibody which reacts with a sensitizing antigen. Cloning of the hybridoma which produces a target antibody may be performed through, for example, a limiting dilution technique. In this case, the antigen employed may be an antigen employed in immunization.

In addition to preparation of the aforementioned hybridoma through immunization of an animal (other than human) with an antigen, a human antibody of interest having binding activity to AMIGO2 protein can be prepared by sensitizing human lymphocyte with AMIGO2 protein in vitro, and fusing the thus-sensitized lymphocyte with a human-derived myeloma cell having permanent division capacity (see JP-B-01-059878). Alternatively, AMIGO2 protein serving as an antigen may be administered to a transgenic animal having all the human antibody gene repertories, to thereby yield a cell which produces an anti-AMIGO2 antibody, and a human antibody against AMIGO2 protein may be obtained from the cell after it has been immortalized (see WO 94/25585 pamphlet, WO 93/12227 pamphlet, WO 92/03918 pamphlet, and WO 94/02602 pamphlet).

The thus-prepared monoclonal-antibody-producing hybridoma can be subcultured in a common culture medium, and can be stored in liquid nitrogen for a long period of time.

A monoclonal antibody is produced from the hybridoma through, for example, a method in which the hybridoma is cultured by a customary technique, and the monoclonal antibody is obtained from the resultant culture supernatant; or a method in which the hybridoma is administered to a mammal exhibiting compatibility with the hybridoma to thereby proliferate the hybridoma, and the monoclonal antibody is obtained from ascitic fluid of the mammal. The former method is suitable for obtaining a monoclonal antibody of high purity, whereas the latter method is suitable for mass production of a monoclonal antibody.

The monoclonal antibody employed in the present invention may be a recombinant antibody. Such a recombinant antibody is produced through the following procedure: the antibody gene is cloned from the hybridoma; the gene is integrated into an appropriate vector; and the vector is introduced into a host, followed by production of the recombinant antibody through a genetic recombination technique (see, for example, Vandamme, A. M., et al., Eur. J. Biochem. (1990) 192, 767-775, 1990).

Specifically, mRNA encoding a variable (V) region of an anti-AMIGO2 antibody is isolated from the hybridoma which produces the anti-AMIGO2 antibody. Isolation of mRNA is carried out through a known method such as the guanidine ultracentrifugation method (Chirgwin, J. M., et al., Biochemistry (1979) 18, 5294-5299) or the APGC method (Chomczynski, P., et al., Anal. Biochem. (1987) 162, 156-159) to thereby prepare total RNA, and target mRNA is prepared by means of, for example, mRNA Purification Kit (product of Pharmacia). Alternatively, mRNA may be directly prepared by means of QuickPrep mRNA Purification Kit (product of Pharmacia).

The thus-obtained mRNA is employed for synthesis of cDNA of the antibody V region by use of reverse transcriptase. Synthesis of cDNA is carried out by means of, for example, AMV Reverse Transcriptase First-strand cDNA Synthesis Kit (product of Seikagaku Corporation). Alternatively, synthesis and amplification of cDNA may be carried out by means of, for example, 5'-Ampli FINDER RACE Kit (product of Clontech) or the 5'-RACE method using PCR (Frohman, M. A., et al., Proc. Natl. Acad. Sci. USA (1988) 85, 8998-9002, Belyaysky, A., et al., Nucleic Acids Res. (1989) 17, 2919-2932).

A target DNA fragment is purified from the resultant PCR product and ligated to vector DNA. Subsequently, a recombinant vector is prepared from the vector DNA, and then introduced into *Escherichia coli* or the like, followed by colony selection, to thereby prepare a recombinant vector of interest. The nucleotide sequence of the target DNA fragment is determined through a known method such as the dideoxynucleotide chain termination method.

DNA encoding the V regions of a target anti-AMIGO2 antibody is obtained, and then the DNA is integrated into an expression vector containing DNA encoding the constant regions (C regions) of the target antibody.

In order to produce the anti-AMIGO2 antibody employed in the present invention, the gene for the antibody is integrated into an expression vector so that the gene can be expressed under control of an expression regulatory region (e.g., an enhancer or a promoter). Subsequently, a host cell is transformed with this expression vector for expression of the antibody.

The gene for the antibody may be expressed by transforming a host cell with both an expression vector containing the DNA encoding the heavy chain (H chain) of the antibody and an expression vector containing the DNA encoding the light chain (L chain) of the antibody, or by transforming a host cell with a single expression vector containing the DNA encoding the heavy and light chains of the antibody (see WO 94/11523).

In addition to the aforementioned host cell, a transgenic animal may be employed for production of a recombinant antibody. For example, an antibody gene is inserted into a gene encoding a protein produced specifically in milk (such as goat β-casein) to prepare a fusion gene. A DNA fragment including the fusion gene having the inserted antibody gene is injected into an embryo of a goat, and this embryo is implanted into a female goat. A target antibody is obtained from milk produced by transgenic goats born from the goat impregnated with the embryo or progeny thereof. In order to increase the amount of the antibody-containing milk produced by the transgenic goats, hormones may be administered to the transgenic goats as appropriate (Ebert, K. M. et al., Bio/Technology (1994) 12, 699-702).

The antibody employed in the present invention is not limited to the whole antibody molecule. So long as the antibody binds to AMIGO2 protein, the antibody may be an antibody fragment, a modified antibody fragment, a divalent antibody, or a monovalent antibody. Examples of the antibody fragment include Fab, F(ab')$_2$, Fv, Fab/c having one Fab and complete Fc, and single-chain Fv (scFv) in which Fv fragments of the H or L chain are linked together with an appropriate linker. Specifically, an antibody is treated with an enzyme (e.g., papain or pepsin) to produce an antibody fragment. Alternatively, a gene encoding the antibody fragment is constructed, and introduced into an expression vector, followed by expression in an appropriate host cell (see, for example, Co, M. S., et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J., et al., Methods in Enzymology (1989) 121, 663-669, and Bird, R. E., et al., TIBTECH (1991) 9, 132-137).

The fragment scFv is obtained by linking the H chain V region and L chain V region of an antibody. In the scFv fragment, the H chain V region and the L chain V region are linked by a linker (preferably, a peptide linker) (Huston, J. S., et al., Proc. Natl. Acad. Sci. U.S.A. (1988) 85, 5879-5883). The H chain V region and the L chain V region in the scFv fragment may be derived from any of the antibodies described herein. The peptide linker employed for linking the V regions is, for example, any single-stranded peptide including 12 to 19 amino acid residues.

DNA encoding the scFv fragment is obtained through PCR amplification employing, as a template, the entire sequence of the DNA encoding the H chain or H chain V region of the aforementioned antibody or the DNA encoding the L chain or L chain V region of the antibody, or a portion of the DNA sequence encoding an amino acid sequence of interest, in combination with a primer pair defining both ends of the DNA sequence, followed by amplification employing the DNA encoding a peptide linker region in combination with a primer pair which defines both ends of the DNA so that the respective ends are linked to the H and L chains.

Once the DNA encoding the scFv fragment is prepared, an expression vector containing the DNA and a host transformed with the expression vector can be obtained through a customary method, and the scFv fragment can be obtained through a customary method by use of the host.

Such an antibody fragment may be produced by a host after the gene for the fragment has been obtained and expressed in a manner similar to that described above. As used herein, the term "antibody" also encompasses such an antibody fragment.

As a modified anti-AMIGO2 antibody, an anti-AMIGO2 antibody bound to a molecule (e.g., a labeling substance) may be employed. As used herein, the term "antibody" also encompasses such a modified antibody. Such a modified antibody may be prepared through chemical modification of the above-obtained antibody. Methods for modifying antibodies have already been established in the art.

Also, the antibody employed in the present invention may be a bispecific antibody. The bispecific antibody may have antigen-binding sites recognizing different epitopes of AMIGO2 molecule, or may have an antigen-binding site recognizing AMIGO2 protein and an antigen-binding site recognizing a labeling substance or the like. A bispecific antibody may be prepared by binding HL pairs of two antibodies, or may be obtained from a bispecific-antibody-producing fused cell prepared through fusion of hybridomas producing different monoclonal antibodies. Alternatively, a bispecific antibody may be prepared through a genetic engineering technique.

The above-constructed gene for the antibody may be expressed through a known method, to thereby yield the antibody. In the case where a mammalian cell is employed, the antibody gene may be expressed by functionally binding a common useful promoter, the gene which is expressed, and a polyA signal downstream of the 3' end thereof. Examples of the promoter/enhancer which may be employed include human cytomegalovirus immediate early promoter/enhancer.

Other promoters/enhancers which may be employed for antibody expression in the present invention include viral promoters/enhancers such as retrovirus, polyomavirus, adenovirus, and simian virus 40 (SV40); and promoters/enhancers derived from mammalian cells, such as human elongation factor 1α (HEF1α).

When SV40 promoter/enhancer is employed, gene expression can be readily carried out through the method of Mulligan, et al. (Nature (1979) 277, 108), whereas when HEF1α promoter/enhancer is employed, gene expression can be readily carried out through the method of Mizushima, et al. (Nucleic Acids Res. (1990) 18, 5322).

In the case where *Escherichia coli* is employed, the gene for the antibody can be expressed by functionally binding a common useful promoter, a signal sequence for secreting the antibody, and the antibody gene which is expressed. Examples of the promoter which may be employed include lacZ promoter and araB promoter. When lacZ promoter is employed, the gene can be expressed through the method of Ward, et al. (Nature (1098) 341, 544-546; FASEBJ. (1992) 6, 2422-2427), whereas when araB promoter is employed, the gene can be expressed through the method of Better, et al. (Science (1988) 240, 1041-1043).

When the antibody is produced in the periplasm of *Escherichia coli*, the pelB signal sequence (Lei, S. P., et al., J. Bacteriol. (1987) 169, 4379) may be employed as a signal sequence for secreting the antibody. The antibody produced in the periplasm is isolated, and then employed by appropriately refolding the structure of the antibody.

Replication origins which may be employed include those derived from SV40, polyomavirus, adenovirus, bovine papilloma virus (BPV), and the like. In order to increase gene copy number in a host cell system, the expression vector employed may contain a selective marker such as aminoglycoside transferase (APH) gene, thymidine kinase (TK) gene, *Escherichia coli* xanthine-guanine phosphoribosyl transferase (Ecogpt) gene, or dihydrofolate reductase (dhfr) gene.

Any expression system such as a eukaryotic or prokaryotic system may be used for production of the antibody employed in the present invention. Examples of the eukaryotic cell include animal cells of, for example, established mammalian cell line, cells of insect cell line, filamentous fungal cells, and yeast cells; and examples of the prokaryotic cell include cells of a bacterium such as *Escherichia coli*.

Preferably, the antibody employed in the present invention is expressed in a mammalian cell such as CHO, COS, myeloma, BHK, Vero, or HeLa cell.

Subsequently, the above-transformed host cell is cultured in vitro or in vivo to produce a target antibody. Culturing of the host cell is carried out through a known method. For example, DMEM, MEM, RPMI 1640, or IMDM may be employed as a culture medium, and a serum supplement such as fetal calf serum (FCS) may be employed in combination.

The above-expressed or produced antibody can be isolated from cells or a host animal and purified to homogeneity. Isolation and purification of the antibody employed in the present invention may be carried out by means of an affinity column. Examples of columns employing protein A column include Hyper D, POROS, and Sepharose FF (product of Pharmacia). No particular limitation is imposed on the method for isolation/purification of the antibody, and the antibody may be isolated or purified through any method which is generally employed for isolation/separation of proteins. For example, the antibody may be isolated/purified by appropriately selecting or combining chromatography columns other than the aforementioned affinity columns, filters, ultrafiltration, salting out, dialysis, etc. (Antibodies: A Laboratory Manual. Ed Harlow, David Lane, Cold Spring Harbor Laboratory, 1988).

The therapeutic drug for pancreatic cancer of the present invention may be prepared into a drug product by subjecting both an anti-AMIGO2 antibody and a pharmaceutically acceptable carrier well known in the art to a drug preparation process such as mixing, dissolution, granulation, tableting, emulsification, encapsulation, or lyophilization.

For oral administration, an anti-AMIGO2 antibody may be mixed with, for example, a pharmaceutically acceptable solvent, excipient, binder, stabilizer, or dispersant, and the mixture may be prepared into a dosage form such as tablet, pill, sugar-coated agent, soft capsule, hard capsule, solution, suspension, emulsion, gel, syrup, or slurry.

For parenteral administration, an anti-AMIGO2 antibody may be mixed with, for example, a pharmaceutically acceptable solvent, excipient, binder, stabilizer, or dispersant, and the mixture may be prepared into a dosage form such as injection solution, suspension, emulsion, cream, ointment, inhalant, or suppository. For formulation of an injection, an anti-AMIGO2 antibody may be dissolved in an aqueous solution, preferably, a physiologically compatible buffer (e.g., Hanks' solution, Ringer solution, or saline buffer). The composition may be in the form of suspension, solution, or emulsion in an oily or aqueous vehicle. Alternatively, the therapeutic drug may be produced in the form of powder, and, before use, the drug may be prepared into an aqueous solution or suspension with, for example, sterile water. For inhalation administration, an anti-AMIGO2 antibody may be powdered, and may be prepared into a powder mixture together with an appropriate base such as lactose or starch. For production of a suppository, an anti-AMIGO2 antibody may be mixed with a conventional suppository base such as cocoa butter. The therapeutic drug of the present invention may be formulated into a sustained-release drug product by being encapsulated in a polymer matrix, etc.

The dose of the therapeutic drug or the number of doses thereof varies depending on the dosage form or administration route thereof, or the symptom, age, or body weight of a patient in need thereof. The drug can be administered once to several times per day so that the daily dose of an anti-AMIGO2 antibody is generally about 0.001 mg to about 1,000 mg per kg body weight, preferably about 0.01 mg to about 10 mg per kg body weight.

Generally, the therapeutic drug for pancreatic cancer of the present invention is preferably administered through a parenteral route; for example, injection (e.g., subcutaneous injection, intravenous injection, intramuscular injection, or intraperitoneal injection), or transdermal, transmucosal, transnasal, or transpulmonary administration.

EXAMPLES

The present invention will next be described in more detail by way of examples, which should not be construed as limiting the invention thereto.

Example 1

Analysis of AMIGO2 Gene Expression in Cancer Cell Lines by Means of DNA Microarray In order to retrieve genes which are highly expressed in pancreatic cancer, through a customary method employing ISOGEN (product of Nippon Gene Co., Ltd.), total RNA was prepared from each of human tissues and cancer cell lines shown in Table 1; or total RNA was prepared from a sample collected, through laser capture microdissection, from each of tissues removed from 24 pancreatic cancer cases with different differentiation degrees, one precancerous lesion case, two pancreatic ductal carcinoma cases, and one pancreatic intraductal papillary mucinous tumor case, or from each of four normal tissues (non-cancerous portions of removed pancreatic cancer tissue) (i.e., control).

The thus-prepared total RNA (each 10 ng) was applied to GeneChip U-133 (product of Affimetrix), and gene expression was analyzed according to Expression Analysis Technical Manual (product of Affimetrix). Genes highly expressed in cancer cells were searched on the basis of the average (taken as 100) of expression scores of all genes. As a result, AMIGO2 mRNA (probe ID: 222108 at HG-U133A) was found to be highly expressed in three of four pancreatic cancer cases: expression scores were found to be 304.0, 148.7, and 448.9, which are respectively 5.7 times, 2.8 times, and 8.5 times that in the case of normal pancreatic tissue (52.9) (FIGS. 1a and 1b).

Through analysis in pancreatic cancer cell lines, AMIGO2 was found to be highly expressed (i.e., expression score: 100 or more) in Capan1, Panc1, PK-45H, PK-45P, PK-59, and QGP-1 (FIG. 1c).

Total RNA was prepared from each of removed pancreatic cancer tissue samples (four well-differentiated samples, 17 moderately differentiated samples, and three poorly differentiated samples), four normal pancreatic tissue samples, one precancerous lesion sample, two pancreatic ductal carcinoma samples, and one pancreatic intraductal papillary mucinous tumor sample. The thus-prepared total RNA (each 10 ng) was applied to GeneChip U133 Plus 2.0 (product of Affimetrix) for gene expression analysis. The gene expression score in each tissue was determined on the basis of the average (taken as 100) of expression scores of all genes as measured by means of GeneChip U133 Plus 2.0. As a result, AMIGO2 mRNA (probe ID: 222108 at HG-U133 plus 2) was found to be less expressed (low expression score) in normal pancreatic tissue, precancerous lesion, pancreatic intraductal papillary mucinous tumor, and well differentiated pancreatic cancer, but AMIGO2 mRNA was found to be highly expressed in moderately or poorly differentiated pancreatic cancer (FIG. 2).

TABLE 1

Tissues and cell lines employed for AMIGO2 gene expression analysis (1/3)

| Normal tissue | Origin | Lot |
|---|---|---|
| Whole brain | Clontech 64020-1 | 101041 |
| Tonsil | Clontech 6574-1 | 1030830 |
| Callosum | Clontech 6577-1 | 1010486 |
| Caudate nucleus | Clontech 6575-1 | 120289 |
| Thalamus | Clontech 6582-1 | 1070147 |
| Hippocampus | Clontech 6578-1 | 1050638 |
| Cerebellum | Clontech 64035-1 | 1010033 |
| Spinal cord | Clontech 6593-1 | 111062 |
| Retina | Clontech 636579 | 3070321 |
| Pituitary gland | Clontech 6584-1 | 2010981 |
| Thymus | Ambion 7964 | 101P0101A |
| Thyroid | Stratagene 735040 | 510225 |
| Salivary gland | Clontech 64026-1 | 1011322 |
| Lung | Clinical sample | 14887 |
| Trachea | Clontech 64091-1 | 1010201 |
| Skin | Stratagene 735031 | 120484 |
| Breast | Stratagene 735044 | 610327 |
| Skeletal muscle | Ambion 7982 | 091P0101C |
| Heart | Ambion 7966 | 110P43B |
| Atrium | Stratagene 835007 | 130025 |
| Kidney | Ambion 7976 | 071P04B |
| Adrenal gland | Clontech 64096-1 | 2020671 |
| Liver | Clinical sample | N4 |
| Pancreas | Ambion 7954 | 091P0104A |
| Spleen | Ambion 7970 | 061P18A |
| Stomach | Clinical sample | MN15 |
| Small intestine | Ambion 7984 | 091P0201A |
| Large intestine | Ambion 7986 | 071P10B |
| Bladder | Ambion 7990 | 81P0101A |
| Bone marrow | Clontech 64106-1 | 1110932 |
| Peripheral blood | Clinical sample | — |
| Testis | Clontech 64027-1 | 6120257 |
| Prostate gland | Ambion 7988 | 081P0103A |
| Ovary | Ambion 7974 | 051P42A |
| Uterus | Stratagene 735042 | 1100640 |
| Placenta | Ambion 7950 | 061P33B |
| Fetal brain | Clontech 64094-1 | 2020902 |
| Fetal liver | CHEMICON 356 | 21060678 |

Tissues and cell lines employed for AMIGO2 gene expression analysis (2/3)

| Cancer tissue | Origin | Number of samples |
|---|---|---|
| Glioblastoma | Clinical sample | 3 |
| Lung cancer (adenocarcinoma) | Clinical sample | 12 |
| Liver cancer (moderately differentiated) | Clinical sample | 3 |
| Liver cancer (poorly differentiated) | Clinical sample | 3 |
| Gastric cancer | Clinical sample | 31 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (small cell carcinoma) | Clinical sample | 1 |
| Lung cancer (squamous cell carcinoma) | Clinical sample | 1 |
| Lung cancer (squamous cell carcinoma) | Clinical sample | 1 |
| Lung cancer (squamous cell carcinoma) | Clinical sample | 1 |
| Lung cancer (squamous cell carcinoma) | Clinical sample | 1 |
| Lung cancer (squamous cell carcinoma) | Clinical sample | 1 |
| Lung cancer (adenocarcinoma) | Clinical sample | 1 |
| Lung cancer (adenocarcinoma) | Clinical sample | 1 |
| Lung cancer (adenocarcinoma) | Clinical sample | 1 |
| Lung cancer (adenocarcinoma) | Clinical sample | 1 |
| Lung cancer (adenocarcinoma) | Clinical sample | 1 |
| Renal cancer | Clinical sample | 1 |
| Renal cancer | Clinical sample | 1 |
| Colon cancer | Clinical sample | 1 |
| Colon cancer | Clinical sample | 1 |
| Colon cancer | Clinical sample | 1 |
| Colon cancer (liver metastasis) | Clinical sample | 1 |
| Colon cancer (liver metastasis) | Clinical sample | 1 |
| Colon cancer (liver metastasis) | Clinical sample | 1 |
| Colon cancer (liver metastasis) | Clinical sample | 1 |
| Colon cancer (liver metastasis) | Clinical sample | 1 |
| Colon cancer (liver metastasis) | Clinical sample | 1 |
| Colon cancer (liver metastasis) | Clinical sample | 1 |

TABLE 1-continued

| Colon cancer | Clinical sample | 1 |
| Colon cancer | Clinical sample | 1 |
| Pancreatic cancer | Clinical sample | 1 |
| Pancreatic cancer | Clinical sample | 1 |
| Pancreatic cancer | Clinical sample | 1 |
| Pancreatic cancer | Clinical sample | 1 |

Tissues and cell lines employed for
AMIGO2 gene expression analysis (3/3)

| Cancer type | Cell line |
|---|---|
| Brain tumor | U251 |
| Breast cancer | MCF-7 |
| Esophageal cancer | TE2 |
| Gastric cancer | AGS |
|  | GT3 |
|  | KatoIII |
|  | MKN45 |
|  | MKN74 |
|  | 2M |
|  | 2MD3 |
| Colon cancer | CaCo2 |
|  | DLD1 |
|  | HCT116 |
|  | LOVO |
|  | SW480 |
| Liver cancer | Alex |
|  | HepG2 |
|  | HLE |
|  | Huh6 |
|  | Huh7 |
| Pancreatic cancer | Capan1 |
|  | KLM1 |
|  | MIA PaCa2 |
|  | NOR-P1 |
|  | Panc1 |
|  | PK-1 |
|  | PK-8 |
|  | PK-9 |
|  | PK-45H |
|  | PK-45P |
|  | PK-59 |
|  | QGP-1 |
| Renal cancer | Caki1 |
|  | Caki2 |
|  | ACHN |
| Lung cancer | A549 |
|  | Lu130 |
|  | H1395 |
|  | H157 |
|  | H1648 |
|  | H2009 |
|  | H23 |
|  | H2347 |
|  | H522 |
|  | H1437 |
|  | H2122 |
| Bladder cancer | EJ1 |
|  | T24 |
| Ovarian cancer | OVCAR |
| Cervical cancer | HeLa |

Example 2

Cloning of AMIGO2 cDNA

AMIGO2 cDNA was amplified through PCR employing, as a template, cDNA derived from the pancreatic cancer cell line PK-59. This PCR was carried out by use of a primer set of AMIGO2FW (SEQ ID NO: 3) and AMIGO2RV (SEQ ID NO: 4) designed on the basis of sequence data of GenBank number (NM 181847) for amplification of a fragment including an ORF (open reading flame) region. This PCR was carried out by use of KOD-plus (product of Toyobo Co., Ltd.) through 40 cycles, each including the steps of 15 seconds at 94° C., 15 seconds at 60° C., and 120 seconds at 68° C.

Thereafter, the resultant PCR product was subjected to agarose gel electrophoresis, and then a gel fragment containing a band of about 1.6 kbp, which is approximate to a target size, was cut out. This gel fragment was subjected to purification by means of QIAquick gel extraction kit (product of Qiagen), to thereby yield AMIGO2 full-length cDNA of interest (hereinafter may be referred to as "AMIGO2 full cDNA").

Example 3

Preparation of AMIGO2 Antigen (1) Preparation of Vector for Expression of AMIGO2 Full cDNA in Mammalian Cells In order to insert the aforementioned AMIGO2 full cDNA into the mammalian expression vector pEF4/Myc-HisB (product of Invitrogen), the cDNA was treated with two restriction enzymes: KpnI and EcoRV (products of TaKaRa), and the thus-treated cDNA was inserted into KpnI/EcoRV-treated pEF4/Myc-HisB through ligation by means of a rapid DNA ligation kit (product of Roche Diagnostics). Nucleotide sequence analysis was carried out through a customary method, and an expression vector of interest, pEF4/AMIGO2 full, was yielded.

(2) Preparation of Vector for Expression, in Mammalian Cells, of Partial-Length cDNA Corresponding to Extracellular Region of AMIGO2

PCR was carried out by using AMIGO2 full cDNA as a template, and a primer set of AMIGO2FW (SEQ ID NO: 3) and sAMIGO2-Rv-KY (SEQ ID NO: 5) designed on the basis of sequence data of GenBank number (NM 181847) for amplification of a cDNA fragment (sAMIGO2 cDNA) corresponding to an extracellular region of AMIGO2. This PCR was carried out by use of KOD-plus (product of Toyobo Co., Ltd.) through 40 cycles, each including the steps of 15 seconds at 94° C., 15 seconds at 60° C., and 90 seconds at 68° C.

The resultant PCR product was subjected to agarose gel electrophoresis, and then a gel fragment containing a band of about 900 bp, which is approximate to a target size, was cut out. This gel fragment was subjected to purification by means of QIAquick gel extraction kit (product of Qiagen), to thereby yield sAMIGO2 cDNA of interest.

In order to insert this sAMIGO2 cDNA into the mammalian expression vector pEF4/Myc-HisB (product of Invitrogen), the cDNA was treated with two restriction enzymes: KpnI and XbaI (products of TaKaRa), and the thus-treated cDNA was inserted into KpnI/XbaI-treated pEF4/Myc-HisB through ligation by means of a rapid DNA ligation kit (product of Roche Diagnostics). Nucleotide sequence analysis was carried out through a customary method, and an expression vector of interest, pEF4/sAMIGO2, was yielded.

(3) Expression of Full-Length AMIGO2 Protein and sAMIGO2 Protein

According to the protocol of FuGENE6 transfection reagent (product of Roche Diagnostics), on the day before transfection, $8 \times 10^5$ CHO cells were inoculated onto a dish (diameter: 10 cm), followed by culturing overnight. On the following day, the expression vector pEF4/AMIGO2 full or pEF4/sAMIGO2 (8 μg) and the FuGENE6 reagent (16 μL)

were mixed with serum-free Opti-MEM medium (product of Invitrogen) (400 μL), followed by incubation at room temperature for 15 to 45 minutes. Thereafter, the resultant product was added to the cell culture liquid for transfection. On the day following transfection, cloning was initiated through limiting dilution by use of Zeocin (product of Invitrogen) serving as a selection reagent.

Screening of full-length-AMIGO2-expressing CHO cells was carried out through western blotting employing an anti-AMIGO2 monoclonal antibody (product of R & D Systems) and flow cytometry (by means of FACScalibur (product of Becton Dickinson)), to thereby select a well-grown clone exhibiting a strong signal; i.e., a full-length-AMIGO2-expressing CHO clone (EXZ1005). EXZ1005 was employed for screening during preparation of monoclonal antibodies.

Screening of sAMIGO2-expressing CHO cells was carried out through analysis of the concentration of sAMIGO2 secreted into a culture supernatant by western blotting employing an anti-AMIGO2 monoclonal antibody (MAB2080, product of R & D Systems), to thereby select a well-grown clone which is secreted into a large amount in a culture supernatant; i.e., an sAMIGO2-expressing CHO clone (EXZ0902). The thus-selected sAMIGO2-expressing CHO clone (EXZ0902) was cultured for 72 hours in three roller bottles, each having a culture area of 1,500 cm$^2$ and containing serum-free medium CHO-S-SFM-II (product of Invitrogen) (333 mL), followed by recovery of a culture supernatant. The thus-recovered culture supernatant was applied to HisTrap HP column (product of GE Healthcare Bioscience), to thereby purify sAMIGO2 Myc-His tag fusion protein (hereinafter may be referred to as "sAMIGO2 protein"). The fusion protein was found to have a purity of 95% or more through non-reducing SDS-PAGE analysis (FIG. 3). The thus-purified fusion protein was dialyzed against PBS, and employed as a protein for, for example, analysis of an immunogen or identification of an epitope. The sAMIGO2 protein concentration was calculated through the BCA method (by means of a kit produced by PIERCE) employing a calibration curve prepared by use of pure bovine serum albumin having a known concentration.

(4) Preparation of Recombinant Baculovirus Expressing AMIGO2 Immunoglobulin Domain PCR was carried out by using the AMIGO2 full cDNA prepared in Example 2 as a template, and a primer set of BS/AMIGO2/Ig-FW (SEQ ID NO: 6) and BS/AMIGO2/Ig-RV (SEQ ID NO: 7) designed on the basis of sequence data of GenBank number (NM 181847) for amplification of a cDNA fragment (AMIGO2/Ig cDNA) corresponding to an immunoglobulin domain of AMIGO2. This PCR was carried out by use of KOD-plus (product of Toyobo Co., Ltd.) through 40 cycles, each including the steps of 15 seconds at 94° C., 15 seconds at 60° C., and 50 seconds at 68° C. The resultant PCR product was subjected to agarose gel electrophoresis, and then a gel fragment containing a cDNA fragment having a target size was cut out. This gel fragment was applied to QIAquick gel extraction kit (product of Qiagen), to thereby yield AMIGO21 g cDNA of interest. The AMIGO21 g cDNA was treated with the restriction enzyme KpnI (product of TaKaRa) at 37° C. for one hour, and then recovered through extraction with phenol/chloroform, and ethanol precipitation. The thus-prepared AMIGO21 g cDNA was inserted into pBacSurf1 (product of Novagen) cleaved with KpnI (product of TaKaRa), to thereby construct a transfer vector pBS/AMIGO2/Ig. Subsequently, the vector pBS/AMIGO2/Ig (4 μg) was cleaved with the restriction enzyme BpII (product of Fermentas) into a linear form. Thereafter, as directed by Invitrogen, the thus-cleaved vector and Bac-N-Blue DNA were introduced into Sf9 cells, to thereby prepare a recombinant baculovirus expressing an AMIGO2 immunoglobulin domain-gp64 fusion protein.

The thus-prepared recombinant baculovirus was added to Sf9 cells (2×10$^6$ cells/mL), and the cells were infected with the baculovirus so that MOI was 5, followed by culturing at 27° C. for three days. A budding baculovirus (BV) expressing an AMIGO2 immunoglobulin domain-gp64 fusion protein was recovered from a culture supernatant obtained through three-day culturing. Specifically, the culture liquid was subjected to centrifugation at 800×g for 15 minutes, and cells and cell homogenate were removed, followed by recovery of a culture supernatant. The supernatant was subjected to centrifugation at 45,000 g for 30 minutes, and the precipitate was suspended in PBS. The suspension sample was regarded as an AMIGO2-Ig-BV fraction, and employed for identification of an epitope of an anti-AMIGO2 monoclonal antibody as described hereinbelow.

Example 4

Detection of AMIGO2 Through Western Blotting of Pancreatic Cancer Cell Line

By use of a commercially available anti-AMIGO2 monoclonal antibody (MAB2080, product of R & D Systems), AMIGO2 contained in cell lysates of 12 pancreatic cancer cell lines (Capan1, KLM1, MIA PaCa2, NOR-P1, Panc1, PK-1, PK-8, PK-9, PK-45H, PK-45P, PK-59, and QGP-1) and the full-length-AMIGO2-expressing CHO clone (EXZ1005) serving as a positive control was detected through western blotting. Specifically, cells of each cell line were lysed in RIPA buffer (150 mM sodium chloride, 1% Triton X-100, 1% deoxycholic acid, 0.1% SDS, 2 μg/mL aprotinin, 2 μg/mL pepstatin A, 2 μg/mL leupeptin, 0.87 mg/mL PMSF, and 10 mM tris-hydroxyaminomethane hydrochloride (pH 7.4)), to thereby prepare a cell lysate. The cell lysate (10 μL for a pancreatic cancer cell line, or 0.5 μL for the full-length-AMIGO2-expressing CHO clone (EXZ1005) serving as a positive control) was applied to a lane of a non-reducing SDS-PAGE gel.

After completion of electrophoresis, protein was transferred to nitrocellulose membrane (product of GE Healthcare Bioscience). Subsequently, the protein was reacted with the anti-AMIGO2 monoclonal antibody (product of R & D Systems) serving as a primary antibody, and then reacted with a peroxidase-labeled anti-mouse IgG antibody (product of GE Healthcare Bioscience) serving as a secondary antibody, followed by detection of AMIGO2.

Figure 4:
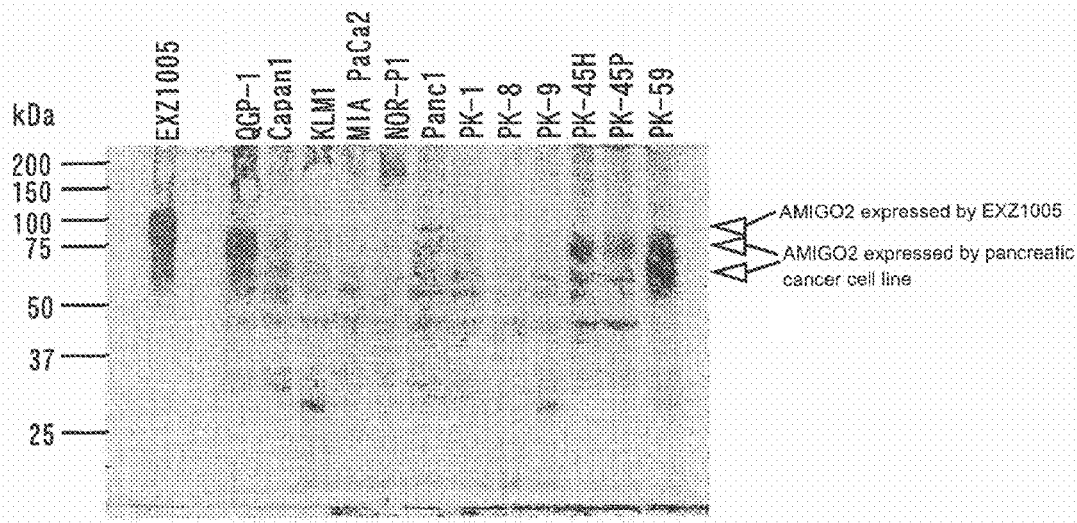
FIG. 4 shows the results of western blot analysis of a full-length-AMIGO2-expressing CHO clone (EXZ1005) lysate and pancreatic cancer cell lysates by use of a commercially available anti-AMIGO2 monoclonal antibody.

As a result, at a position corresponding to a molecular weight of about 75 to about 65 kDa, a strong band was detected in the cell lysate of PK-45H, PK-45P, PK-59, or QGP-1, whereas a weak band was detected in the cell lysate of Capan1, Panc1, or PK-1. Virtually no band was detected in a cell lysate other than the aforementioned cell lysates. These results are correlated with the GeneChip U133 analysis results; i.e., AMIGO2 protein was detected only in a cell line exhibiting high mRNA expression score (FIG. 4). AMIGO2 detected in the lysate of the full-length-AMIGO2-expressing CHO clone (EXZ1005) (i.e., positive control) was found to have a molecular weight of about 85 kDa, which is slightly higher than that of AMIGO2 detected in a pancreatic cancer cell line. Conceivably, this high molecular weight is attributed to the Myc-His tag (molecular weight: about 3 kDa)

added on the C-terminal side of AMIGO2 protein serving as a positive control, as well as to the difference in sugar chain structure.

Example 5

Flow Cytometry of Full-Length-AMIGO2-Expressing CHO Clone (EXZ1005) and Pancreatic Cancer Cell Line by Use of Anti-AMIGO2 Monoclonal Antibody By use of the full-length-AMIGO2-expressing CHO clone (EXZ1005) or the pancreatic cancer cell line PK-45P, in which AMIGO2 was detected through western blotting of the cell lysate as described above, whether or not AMIGO2 is expressed on cell membrane surfaces was analyzed through flow cytometry by means of FACScalibur (product of Becton Dickinson). Specifically, cells of the full-length-AMIGO2-expressing CHO clone (EXZ1005) or the pancreatic cancer cell line PK-45P were removed from a culture plate through treatment with 2 mM EDTA-PBS, and the cells were suspended in FACS solution (PBS containing 1% bovine serum albumin, 0.1 mM EDTA, and 0.1% $NaN_3$) ($1 \times 10^6$ cells/mL). The cell suspension was inoculated into a 96-well plate (product of BD Falcon) (50 µL/well), and a commercially available anti-AMIGO2 monoclonal antibody (product of R & D Systems) was added to the plate (0.6 µg/well), followed by reaction at 4° C. for 60 minutes. Subsequently, the plate was washed twice with FACS solution (200 µL/well), and then an FITC-labeled anti-mouse IgG antibody (product of Jackson) was added to the plate, followed by reaction at 4° C. for 30 minutes.

Subsequently, the plate was washed twice with FACS solution, and then flow cytometry was carried out by means of FACSCalibur (product of Becton Dickinson) according to the instruction thereof. Normal mouse IgG was employed as a negative control of the anti-AMIGO2 monoclonal antibody. The anti-AMIGO2 monoclonal antibody was reacted with sAMIGO2 protein (5.1 µg/well) before being reacted with the cells, to thereby determine whether or not a peak shift through flow cytometry occurs.

Figure 5:
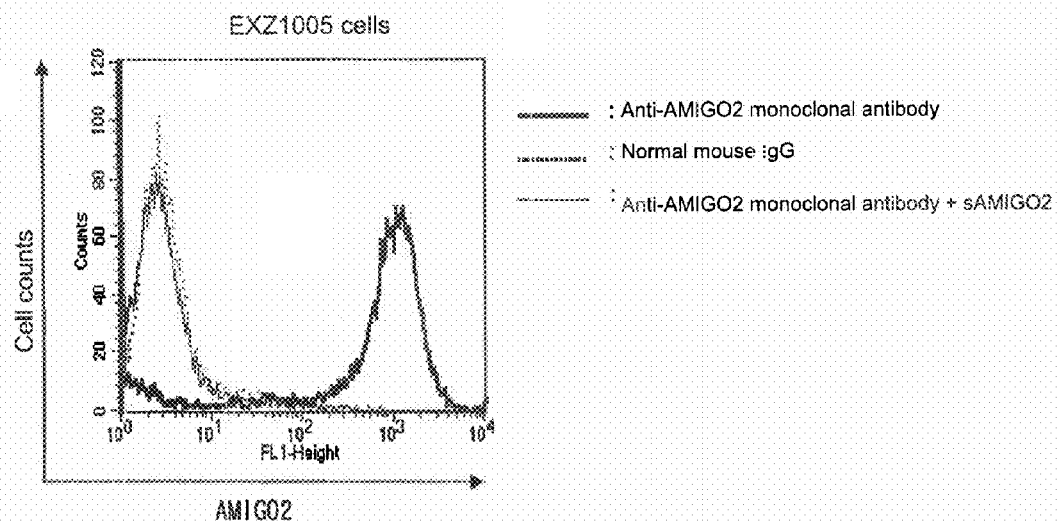
FIG. 5 shows the results of flow cytometry of the full-length-AMIGO2-expressing CHO clone (EXZ1005).
Figure 6:
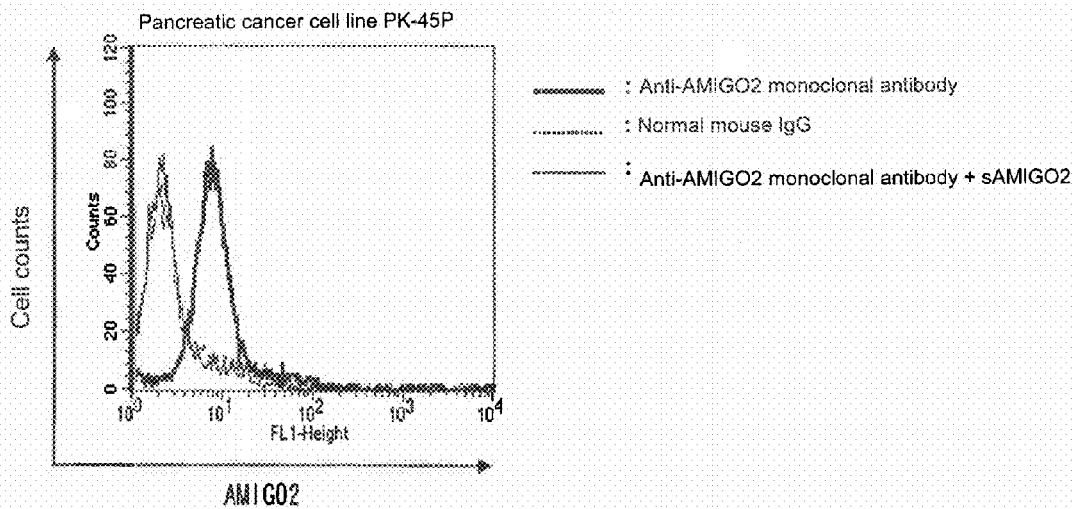
FIG. 6 shows the results of flow cytometry of a pancreatic cancer cell line PK-45P.

FIG. 5 shows the results of flow cytometry of the full-length-AMIGO2-expressing CHO clone (EXZ1005). A peak shift occurred when the anti-AMIGO2 monoclonal antibody was reacted with EXZ1005 cells, but this peak shift did not occur when the anti-AMIGO2 monoclonal antibody was reacted with sAMIGO2 protein before being reacted with the cells. FIG. 6 shows the results of flow cytometry of the pancreatic cancer cell line PK-45P. Similar to the case of the full-length-AMIGO2-expressing CHO clone (EXZ1005), peak shift occurred when the anti-AMIGO2 monoclonal antibody was reacted with PK-45P cells, but virtually no peak shift occurred when the anti-AMIGO2 monoclonal antibody was reacted with sAMIGO2 protein before being reacted with the cells.

These data indicate that AMIGO2 protein is expressed on the surfaces of cell membranes of the full-length-AMIGO2-expressing CHO clone (EXZ1005) or the pancreatic cancer cell line PK-45P. Thus, EXZ1005 or PK-45P was employed for screening during preparation of anti-AMIGO2 antibodies.

Example 6

Preparation of Anti-AMIGO2 Monoclonal Antibody sAMIGO2 protein (50 µg) dissolved in PBS was mixed with an equiamount of Titer-MAX (TiterMax USA, Inc.), and the mixture was intraperitoneally injected into MRL/lpr mice (Sankyo Labo Service Corporation) for the first immunization. In the second or subsequent immunization, sAMIGO2 protein prepared in a manner similar to that described above (protein amount: 25 µg) was mixed with Titer-MAX, and the mixture was intraperitoneally injected. Three days after the final immunization, spleen cells were aseptically prepared from the mice, and were fused with mouse myeloma cells (NS1) through the polyethylene glycol method.

Screening of hybridoma culture supernatants for anti-AMIGO2 antibodies was carried out in a manner similar to that described in Example 5; i.e., through flow cytometry (by means of FACSCalibur (product of Becton Dickinson)) employing the full-length-AMIGO2-expressing CHO clone (EXZ1005). As a result, 28 positive hybridomas were obtained as shown in Table 2. In Table 2, "IMS" (immunized mouse serum) represents antiserum (0.3 µL/well) from mice immunized with sAMIGO2 protein; i.e., a positive control; and "NMS" (non-immunized mouse serum) represents antiserum (0.3 µL/well) from mice before immunization; i.e., a negative control.

TABLE 2

Results of screening of hybridoma culture supernatants by use of full-length-AMIGO2-expressing CHO clone (EXZ1005)

| No. | Clone number | Flow cytometry (Average fluorescence intensity) | |
|---|---|---|---|
| | | EXZ1005 | CHO cells |
| 1 | PPZ2902 | 36.21 | 12.81 |
| 2 | PPZ2904 | 37.60 | 14.70 |
| 3 | PPZ2912 | 47.67 | 17.35 |
| 4 | PPZ2913 | 53.93 | 12.59 |
| 5 | PPZ2919 | 82.60 | 18.94 |
| 6 | PPZ2920 | 437.73 | 18.11 |
| 7 | PPZ2927 | 342.43 | 11.90 |
| 8 | PPZ2936 | 455.40 | 14.25 |
| 9 | PPZ2937 | 227.17 | 19.71 |
| 10 | PPZ2952 | 140.35 | 17.26 |
| 11 | PPZ2953 | 122.67 | 25.78 |
| 12 | PPZ2956 | 614.72 | 17.23 |
| 13 | PPZ2970 | 207.42 | 13.81 |
| 14 | PPZ3003 | 90.50 | 10.56 |
| 15 | PPZ3016 | 38.71 | 6.79 |
| 16 | PPZ3117 | 10.81 | 13.06 |
| 17 | PPZ3122 | 90.15 | 11.07 |
| 18 | PPZ3124 | 247.24 | 10.02 |
| 19 | PPZ3125 | 215.34 | 12.03 |
| 20 | PPZ3126 | 153.77 | 11.89 |
| 21 | PPZ3130 | 20.68 | 12.36 |
| 22 | PPZ3133 | 504.83 | 8.88 |
| 23 | PPZ3134 | 260.39 | 12.41 |
| 24 | PPZ3135 | 637.44 | 14.67 |
| 25 | PPZ3145 | 763.27 | 12.40 |
| 26 | PPZ3148 | 140.80 | 9.75 |
| 27 | PPZ3150 | 103.31 | 12.22 |
| 28 | PPZ3160 | 706.05 | 6.88 |
| — | IMS | 879.68 | 9.64 |
| — | NMS | 17.07 | 7.79 |

Subsequently, in a manner similar to that described in Example 5, the culture supernatants of these 28 positive hybridomas were subjected to flow cytometry employing the pancreatic cancer cell line PK-45P, to thereby evaluate reactivity of PK-45P to an anti-AMIGO2 antibody. In this experiment, in order to determine that an anti-AMIGO2 antibody contained in each of the hybridoma culture supernatants reacts specifically with AMIGO2 expressed on the cell membrane of the pancreatic cancer cell line PK-45P, sAMIGO2 protein (5.1 µg/well) was added to the culture supernatant before the culture supernatant was reacted with PK-45P cells, to thereby examine whether or not the antibody contained in the culture supernatant is neutralized, and peak shift is reduced in flow cytometry. As a result, in the case of the culture supernatants of 27 hybridomas (exclusive of PPZ2927), peak shift was reduced through addition of sAMIGO2 protein; i.e., an antibody contained in each of the 27 hybridoma culture supernatants was found to bind specifically to AMIGO2 expressed on the cell membrane of the pancreatic cancer cell line PK-45P.

TABLE 3

Results of screening of hybridoma culture supernatants by use of pancreatic cancer cell line PK-45P

| No. | Clone number | Flow cytometry (Average fluorescence intensity) | |
|---|---|---|---|
| | | sAMIGO2(−) | sAMIGO2 (+) |
| 1 | PPZ2902 | 3.96 | 3.03 |
| 2 | PPZ2904 | 4.35 | 3.87 |
| 3 | PPZ2912 | 5.12 | 3.94 |
| 4 | PPZ2913 | 6.16 | 3.59 |
| 5 | PPZ2919 | 4.94 | 3.56 |
| 6 | PPZ2920 | 6.73 | 3.78 |
| 7 | PPZ2927 | 7.86 | 8.22 |
| 8 | PPZ2936 | 6.01 | 3.72 |
| 9 | PPZ2937 | 5.39 | 3.85 |
| 10 | PPZ2952 | 6.16 | 3.61 |
| 11 | PPZ2953 | 4.32 | 3.40 |
| 12 | PPZ2956 | 6.64 | 3.40 |
| 13 | PPZ2970 | 7.90 | 3.28 |
| 14 | PPZ3003 | 7.09 | 3.84 |
| 15 | PPZ3016 | 6.27 | 3.37 |
| 16 | PPZ3117 | 5.19 | 3.90 |
| 17 | PPZ3122 | 6.70 | 3.33 |
| 18 | PPZ3124 | 8.28 | 4.97 |
| 19 | PPZ3125 | 7.04 | 3.54 |
| 20 | PPZ3126 | 24.59 | 15.45 |
| 21 | PPZ3130 | 6.83 | 4.46 |
| 22 | PPZ3133 | 8.28 | 3.44 |
| 23 | PPZ3134 | 13.82 | 10.24 |
| 24 | PPZ3135 | 7.13 | 4.08 |
| 25 | PPZ3145 | 8.03 | 3.71 |
| 26 | PPZ3148 | 7.47 | 3.77 |
| 27 | PPZ3150 | 6.51 | 3.87 |
| 28 | PPZ3160 | 9.13 | 4.66 |

Subsequently, among the hybridomas shown in Table 3, 27 hybridomas (exclusive of PPZ2927) were subjected to cloning by limiting dilution, to thereby finally establish 20 clones. Subsequently, each of the thus-cloned hybridomas was implanted into the peritoneal cavity of pristane-treated BALB/c AJcl-nu/nu mice (CLEA Japan, Inc.) ($1 \times 10^7$ cells/mouse), to thereby prepare ascitic fluid.

Example 7

Purification of Anti-AMIGO2 Monoclonal Antibody and Identification of Subclass Thereof An antibody was purified from the ascitic fluid prepared in Example 6 through salting out by use of ammonium sulfate and affinity chromatography by means of HiTrap Protein G column (GE Healthcare Bioscience). The subclass of the thus-purified antibody was identified by means of a mouse monoclonal antibody isotyping kit (GE Healthcare Bioscience) (Table 4).

TABLE 4

Subclass of purified anti-AMIGO2 antibody

| No. | Clone number | Subclass |
|---|---|---|
| 1 | PPZ2904 | IgG2a, κ |
| 2 | PPZ2912 | IgG2a, κ |
| 3 | PPZ2913 | IgG2b, κ |
| 4 | PPZ2919 | IgG2a, κ |
| 5 | PPZ2920 | IgG1, κ |
| 6 | PPZ2936 | IgG1, κ |
| 7 | PPZ2937 | IgG2a, κ |
| 8 | PPZ2952 | IgG1, κ |
| 9 | PPZ2956 | IgG1, κ |
| 10 | PPZ3003 | IgG2a, κ |
| 11 | PPZ3016 | IgG2a, κ |
| 12 | PPZ3122 | IgG2a, κ |
| 13 | PPZ3124 | IgG2a, κ |
| 14 | PPZ3125 | IgG2a, K |
| 15 | PPZ3130 | IgG2a, κ |
| 16 | PPZ3133 | IgG1, κ |
| 17 | PPZ3135 | IgG2a, κ |
| 18 | PPZ3145 | IgG1, κ |
| 19 | PPZ3148 | IgG2a, κ |
| 20 | PPZ3160 | IgG1, κ |

Example 8

Identification of Epitope of Anti-AMIGO2 Monoclonal Antibody Through Western Blotting sAMIGO2 protein or AMIGO2-Ig-BV fraction, serving as an antigen, was treated with a reducing or non-reducing sample buffer, and then applied to SDS-PAGE (150 ng/lane for sAMIGO2 protein, or 590 ng/lane for AMIGO2-Ig-BV fraction). After completion of electrophoresis, the protein contained in the gel was transferred to Hybond-P membrane (GE Healthcare Bioscience) at 38 V for 16 hours. The transfer membrane was blocked by use of 40% Block Ace (Snow Brand Milk Products Co., Ltd.)/TBS (50 mM Tris-HCl (pH 7.5), 150 mM NaCl) at room temperature for one hour. Subsequently, the protein was reacted, at room temperature for one hour, with an anti-AMIGO2 monoclonal antibody which had been diluted with 40% Block Ace (Snow Brand Milk Products Co., Ltd.)/TBS to 3 µg/mL. Thereafter, the membrane was washed with TEST (50 mM Tris-HCl (pH 7.5), 150 mM NaCl, 0.05% Tween 20) (five minutes×3).

Thereafter, the protein was reacted, at room temperature for one hour, with an HRP-labeled anti-mouse IgG antibody (GE Healthcare Bioscience) which had been diluted 5.000-fold with 10% Block Ace (Snow Brand Milk Products Co., Ltd.)/TBS, followed by washing with TEST (five minutes×3). Finally, an ECL detection reagent (GE Healthcare Bioscience) was caused to act on the membrane, and an X-ray film was exposed to chemiluminescent signal for five minutes. Antibody reactivity to each of the antigens was determined on the basis of the color intensity of the corresponding band. The results are summarized in Table 5.

TABLE 5

Reactivity of anti-AMIGO2 monoclonal antibody as determined through western blotting

| No. | Clone number | sAMIGO2 | | AMIGO2-Ig | |
|---|---|---|---|---|---|
| | | Non-reducing | Reducing | Non-reducing | Reducing |
| 1 | PPZ2904 | + | + | + | + |
| 2 | PPZ2912 | + | + | + | + |
| 3 | PPZ2913 | + | + | + | + |
| 4 | PPZ2919 | − | − | − | − |

TABLE 5-continued

Reactivity of anti-AMIGO2 monoclonal antibody as determined through western blotting

| No. | Clone number | sAMIGO2 Non-reducing | sAMIGO2 Reducing | AMIGO2-Ig Non-reducing | AMIGO2-Ig Reducing |
|---|---|---|---|---|---|
| 5 | PPZ2920 | − | − | − | − |
| 6 | PPZ2936 | + | + | + | + |
| 7 | PPZ2937 | − | − | − | − |
| 8 | PPZ2952 | + | + | + | + |
| 9 | PPZ2956 | − | − | − | − |
| 10 | PPZ3003 | − | − | − | − |
| 11 | PPZ3016 | + | + | + | + |
| 12 | PPZ3122 | + | + | + | + |
| 13 | PPZ3124 | − | − | − | − |
| 14 | PPZ3125 | − | − | − | − |
| 15 | PPZ3130 | + | + | − | − |
| 16 | PPZ3133 | − | − | − | − |
| 17 | PPZ3135 | − | − | − | − |
| 18 | PPZ3145 | − | − | − | − |
| 19 | PPZ3148 | − | − | − | − |
| 20 | PPZ3160 | − | − | − | − |

In Table 5, "sAMIGO2" represents purified sAMIGO2 protein; "AMIGO2-Ig" represents AMIGO2-Ig-BV fraction; "+" represents the case where reactivity is present; and "−" represents the case where reactivity is absent.

These data indicate that seven anti-AMIGO2 monoclonal antibodies derived from PPZ2904, PPZ2912, PPZ2913, PPZ2936, PPZ2952, PPZ3016, and PPZ3122 recognize an epitope present in the immunoglobulin domain of AMIGO2. These data also indicate that these seven monoclonal antibodies react with an antigen under reducing conditions; i.e., the monoclonal antibodies recognize an epitope which is not dependent on the conformation of AMIGO2 formed by a disulfide bond.

A PPZ3130-derived antibody reacts with sAMIGO2, but does not react with AMIGO2-Ig. This indicates that the PPZ3130-derived antibody recognizes an epitope present in a region including an LRR amino-terminal domain to an LRR carboxyl-terminal domain. Similar to the aforementioned seven monoclonal antibodies, the PPZ3130-derived antibody reacts with an antigen under reducing conditions. This indicates that the PPZ3130-derived antibody also recognizes an epitope which is not dependent on the conformation of AMIGO2 formed by a disulfide bond.

The other 12 anti-AMIGO2 monoclonal antibodies (i.e., antibodies derived from PPZ2919, PPZ2920, PPZ2937, PPZ2956, PPZ3003, PPZ3124, PPZ3125, PPZ3133, PPZ3135, PPZ3145, PPZ3148, and PPZ3160) did not react with any of the antigens. These 12 monoclonal antibodies strongly reacted with the full-length-AMIGO2-expressing CHO clone (EXZ1005) (see Table 2), but did not exhibit reactivity in western blotting, for the following reason. Conceivably, an epitope recognized by these monoclonal antibodies is formed by the higher-order structure of AMIGO2, and the structure of the epitope is lost through exposure to SDS.

Example 9

Determination of Dissociation Constant of Anti-AMIGO2 Monoclonal Antibody

The dissociation constant of a monoclonal antibody was determined by means of BIAcore 3000 System (BIAcore). Firstly, an anti-mouse IgG antibody (BIAcore) was immobilized on a sensor chip CM5 through amine coupling. Subsequently, an anti-AMIGO2 antibody was diluted with a buffer containing HBS-EP (10 mM HEPES, pH 7.4, 150 mM NaCl, 3 mM EDTA, 0.005% surfactant P20) and 0.16 Tween 20 so that the anti-AMIGO2 antibody was immobilized in an amount of about several hundreds of RU, followed by injection, to thereby immobilize the anti-AMIGO2 antibody on the sensor chip. Subsequently, sAMIGO2 protein was diluted with the aforementioned buffer so as to attain a concentration of 25 nM, 50 nM, 100 nM, or 200 nM, followed by injection, to thereby determine binding and dissociation. Thereafter, the dissociation constant of the anti-AMIGO2 antibody was determined by means of an analysis program (BIA evaluation). The results are shown in Table 6.

TABLE 6

Dissociation constant of anti-AMIGO2 monoclonal antibody

| No. | Clone number | Dissociation constant (M) |
|---|---|---|
| 1 | PPZ2904 | 3.0E−08 |
| 2 | PPZ2912 | 1.6E−08 |
| 3 | PPZ2913 | ND |
| 4 | PPZ2919 | 2.0E−08 |
| 5 | PPZ2920 | 9.8E−09 |
| 6 | PPZ2936 | 2.7E−08 |
| 7 | PPZ2937 | 4.5E−08 |
| 8 | PPZ2952 | ND |
| 9 | PPZ2956 | 9.0E−09 |
| 10 | PPZ3003 | 5.9E−08 |
| 11 | PPZ3016 | 7.9E−09 |
| 12 | PPZ3122 | 3.5E−09 |
| 13 | PPZ3124 | 3.0E−08 |
| 14 | PPZ3125 | 5.1E−08 |
| 15 | PPZ3130 | ND |
| 16 | PPZ3133 | 2.6E−09 |
| 17 | PPZ3135 | 4.7E−08 |
| 18 | PPZ3145 | 6.2E−08 |
| 19 | PPZ3148 | 4.6E−08 |
| 20 | PPZ3160 | 2.1E−08 |

"ND" represents the case where dissociation constant is equal to or lower than the detection limit. In addition, for example, "3.0E−08" corresponds to a dissociation constant of $3.0 \times 10^{-8}$.

As shown in Table 6, five monoclonal antibodies derived from PPZ3133, PPZ3122, PPZ3016, PPZ2956, and PPZ2920, which have a low dissociation constant on the order of $10^{-9}$, have high ability to trap sAMIGO2 protein, and thus can be applied to establishment of a system for measuring the level of AMIGO2 contained in blood or tissue through ELISA.

Example 10

Cytotoxic Activity (CDC Activity) of Anti-AMIGO2 Antibody to Full-Length-AMIGO2-Expressing CHO Clone (EXZ1005) or Pancreatic Cancer Cell Line CDC activity was determined through a method employing, as an index, release of lactate dehydrogenase (LDH) contained in a target cell. Specifically, as described below, CDC activity was determined by means of CytoTox96 Non-Radioactive Cytotoxicity Assay Kit (product of Promega) according to the protocol attached to the kit.

The full-length-AMIGO2-expressing CHO clone (EXZ1005) or the pancreatic cancer cell line PK-45P was employed as a target cell. Cells of EXZ1005 or PK-45P were removed from a plate, and then suspended in a 10% FBS-containing DMEM medium ($2 \times 10^5$ cells/mL). The suspension was dispensed into a 96-well U-bottomed plate (product of Becton Dickinson) (100 μL/well), followed by culturing in a carbon dioxide gas incubator overnight. On the following day, cells deposited on the bottom surface of the plate were washed twice with a 5% FBS-containing DMEM medium (containing no Phenol Red), and then a 5% FBS-containing DMEM medium (containing no Phenol Red) was dispensed into the plate (30 μL/well). Subsequently, each of the 20 purified anti-AMIGO2 monoclonal antibodies shown in Table 4 in Example 7 was dispensed into the plate (30 μL/well) (antibody concentration: 10.7 μg/mL, final antibody concentration after reaction: 4 μg/mL), followed by incubation on ice for 30 minutes.

Subsequently, a complement sample prepared by diluting Baby Rabbit Complement (product of CEDARLANE) with a 5% FBS-containing DMEM medium (containing no Phenol Red) (16-fold dilution in the case where the target cell was the full-length-AMIGO2-expressing CHO clone (EXZ1005), or 8-fold dilution in the case where the target cell was the pancreatic cancer cell line PK-45P) was dispensed into the plate (20 μL/well), followed by culturing in a carbon dioxide gas incubator for four hours. After completion of culturing, a supernatant (50 μL) was recovered, and transferred to a flat-bottomed enzymatic assay plate. A substrate mixture attached to the kit was added to the plate (50 μL/well), followed by incubation in the dark at room temperature for 30 minutes. After completion of incubation, a reaction-terminating liquid was added to the plate (50 μL/well). After termination of reaction, absorbance was measured at a wavelength of 490 nm by means of a microplate reader. Antiserum (100-fold diluted) from mice immunized with sAMIGO2 protein was employed as a positive control (IMS), and antiserum (100-fold diluted) from mice before immunization was employed as a negative control (NMS).

Cytotoxic activity can be determined as follows.

$$\text{Cytotoxic activity}(\%) = (A-B-C)/(D-C) \times 100$$

A: [absorbance corresponding to a sample]−[background absorbance of a culture liquid];

B: [absorbance attributed to LDH derived from a complement]−[background absorbance of the culture liquid];

C: [absorbance attributed to LDH which has been naturally released from a target cell]−[background absorbance of the culture liquid]; and D: [absorbance attributed to LDH which has been 100% released from the target cell through addition of 0.9% Triton-X100]−[background absorbance of the culture liquid].

The results are shown in Table 7. In measurement of CDC activity employing the full-length-AMIGO2-expressing CHO clone (EXZ1005), 13 clones exhibited high CDC activity (700 or higher), and seven clones exhibited low CDC activity (700 or lower). In measurement of CDC activity employing the pancreatic cancer cell line PK-45P, seven clones exhibited high CDC activity (100 or higher), and 13 clones exhibited low CDC activity (lower than 10%).

The CDC activity of a clone as measured by use of the full-length-AMIGO2-expressing CHO clone (EXZ1005) is not necessarily correlated with that of the clone as measured by use of the pancreatic cancer cell line PK-45P. Conceivably, this is attributed to, for example, the difference in amount of AMIGO2 protein expressed on the cell membrane between the full-length-AMIGO2-expressing CHO clone (EXZ1005) and the pancreatic cancer cell line PK-45P. Indeed, as is clear from data shown in FIGS. 5 and 6, there is a difference in expression level of AMIGO2 protein between EXZ1005 and PK-45P.

TABLE 7

CDC activity of anti-AMIGO2 monoclonal antibody

| No. | Clone number | CDC activity (%) EXZ1005 | CDC activity (%) PK-45P |
|---|---|---|---|
| 1 | PPZ2904 | 85.0 | 7.2 |
| 2 | PPZ2912 | 79.7 | 7.0 |
| 3 | PPZ2913 | 85.9 | 4.8 |
| 4 | PPZ2919 | 90.9 | 18.4 |
| 5 | PPZ2920 | 2.2 | 6.3 |
| 6 | PPZ2936 | 4.4 | 6.3 |
| 7 | PPZ2937 | 93.0 | 13.1 |
| 8 | PPZ2952 | 3.6 | 6.3 |
| 9 | PPZ2956 | 4.2 | 7.1 |
| 10 | PPZ3003 | 96.9 | 12.6 |
| 11 | PPZ3016 | 79.4 | 4.9 |
| 12 | PPZ3122 | 78.3 | 7.8 |
| 13 | PPZ3124 | 100.0 | 26.2 |
| 14 | PPZ3125 | 79.9 | 17.1 |
| 15 | PPZ3130 | 73.4 | 5.8 |
| 16 | PPZ3133 | 5.7 | 5.5 |
| 17 | PPZ3135 | 78.8 | 24.8 |
| 18 | PPZ3145 | 5.3 | 6.9 |
| 19 | PPZ3148 | 83.4 | 33.7 |
| 20 | PPZ3160 | 3.6 | 7.2 |
| — | IMS | 73.0 | 86.3 |
| — | NMS | 1.7 | 5.6 |

Among the antibodies shown in Table 7, seven antibodies derived from PPZ2919, PPZ2937, PPZ3003, PPZ3124, PPZ3125, PPZ3135, and PPZ3148—which exhibited high CDC activity in both the cases where the full-length-AMIGO2-expressing CHO clone (EXZ1005) was employed, and where the pancreatic cancer cell line PK-45P was employed—were subjected to quantitative determination of CDC activity. Specifically, a test sample was prepared from each of the seven antibodies so that the antibody concentration during reaction was 200 to 0 ng/mL [in the case where the target cell was the full-length-AMIGO2-expressing CHO clone (EXZ1005)] or 200 to 0 μg/mL [in the case where the target cell was the pancreatic cancer cell line PK-45P], and CDC activity was determined in a manner similar to that described above.

Figure 7:
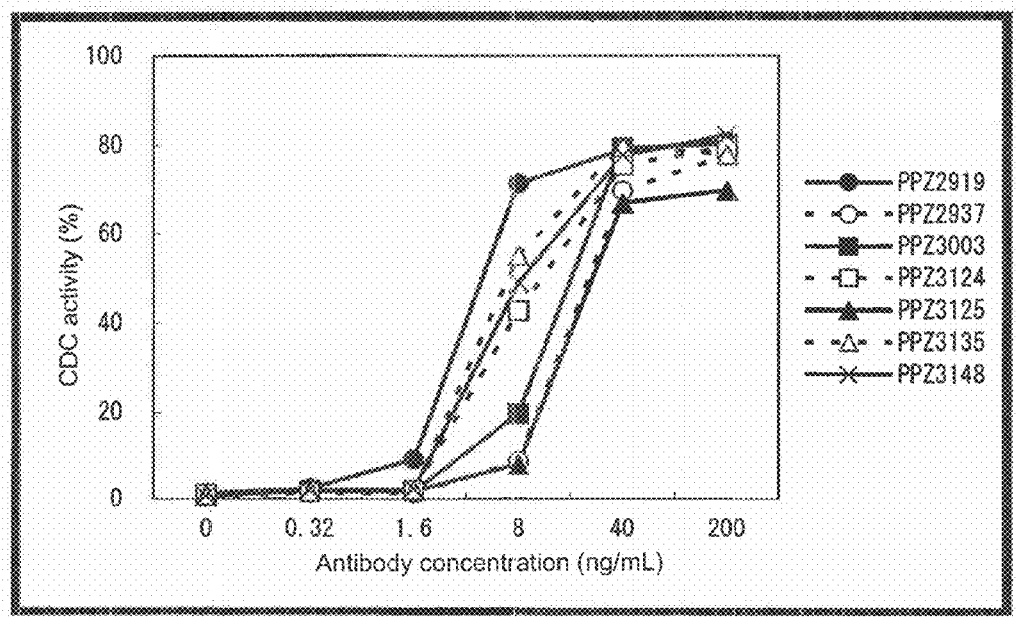
FIG. 7 shows the results of quantitative analysis of CDC activity by use of the full-length-AMIGO2-expressing CHO clone (EXZ1005) as a target cell.
Figure 8:
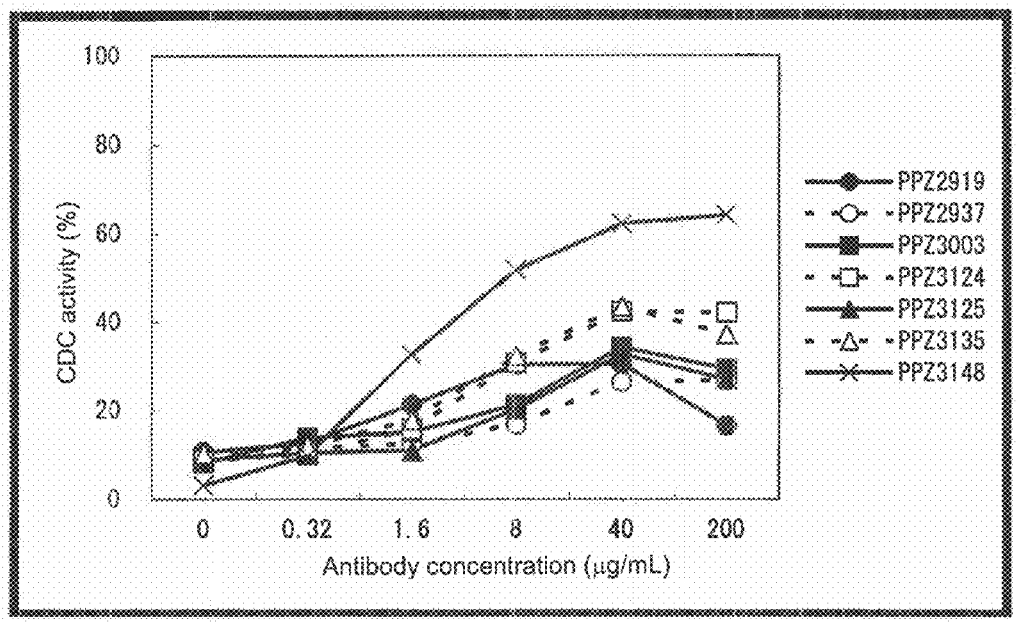
FIG. 8 shows the results of quantitative analysis of CDC activity by use of the pancreatic cancer cell line PK-45P as a target cell.

FIG. 7 shows the results in the case where the target cell was the full-length-AMIGO2-expressing CHO clone (EXZ1005). FIG. 8 shows the results in the case where the target cell was the pancreatic cancer cell line PK-45P. On the basis of data shown in FIGS. 7 and 8, there were determined antibody concentration corresponding to a CDC activity of 50% ($EC_{50}$, in the case where the target cell was the full-length-AMIGO2-expressing CHO clone (EXZ1005)), and antibody concentration corresponding to a CDC activity of 25% ($EC_{25}$, in the case where the target cell was the pancreatic cancer cell line PK-45P). The results are shown in Table 8. As shown in Table 8, four antibodies derived from PPZ2919, PPZ3124, PPZ3135, and PPZ3148 exhibited high CDC activity.

TABLE 8

Results of quantitative analysts of CDC activity in the case where the target cell was the full-length-AMIGO2-expressing CHO clone (EXZ1005) or the pancreatic cancer cell line PK-45P

| No. | Clone number | EC50 (ng/mL)/EXZ1005 | EC25 (μg/mL)/PK-45P |
|---|---|---|---|
| 1 | PPZ2919 | 4.6 | 3.0 |
| 2 | PPZ2937 | 24.0 | 32.0 |
| 3 | PPZ3003 | 18.0 | 21.5 |
| 4 | PPZ3124 | 11.5 | 4.1 |

TABLE 8-continued

Results of quantitative analysts of CDC activity in the case where the target cell was the full-length-AMIGO2-expressing CHO clone (EXZ1005) or the pancreatic cancer cell line PK-45P

| No. | Clone number | EC50 (ng/mL)/EXZ1005 | EC25 (µg/mL)/PK-45P |
|-----|--------------|----------------------|---------------------|
| 5   | PPZ3125      | 25.5                 | 14.5                |
| 6   | PPZ3135      | 6.9                  | 3.5                 |
| 7   | PPZ3148      | 8.6                  | 0.9                 |

An anti-AMIGO2 monoclonal antibody exhibiting such a high CDC activity is considered useful as a drug for the treatment of pancreatic cancer utilizing cytotoxic activity. Applicants submit that the hybridomas producing the aforementioned four monoclonal antibodies were deposited on Sep. 8, 2006 with International Patent Organism Depositary (IPOD), National Institute of Advanced Industrial Science and Technology (AIST), Tsukuba Central 6th, 1-1-1 Higashi, Tsukuba, Ibaraki, Japan; specifically, PPZ2919 (identification number: PPMX0501, accession number: FERM P-21017), PPZ3124 (identification number: PPMX0502, accession number: FERM BP-10809), PPZ3135 (identification number: PPMX0503, accession number: FERM P-21019), and PPZ3148 (identification number: PPMX0504, accession number: FERM BP-10810), as evidenced by the enclosed Certificates of Deposit and corresponding English translations thereof. The hybridoma cell lines identified as PPMX0502 and PPMX0504 were deposited as FERM BP-10809 and FERM BP-10810, respectively, under the terms of the Budapest Treaty. Applicants further submit that all restrictions imposed by the depositor on the availability to the public of the deposited biological material of the hybridoma cell lines identified as PPMX0502 and PPMX0504, and deposited as FERM BP-10809 and FERM BP-10810, respectively, will be irrevocably removed upon the granting of a patent on this application.

When a monoclonal antibody which does not exhibit CDC activity, but which has been found to bind to AMIGO2 expressed on the surfaces of pancreatic cancer cell membranes through flow cytometry is labeled with an isotope or is bound to a compound having cytotoxic activity, the antibody could be useful as a therapeutic drug for pancreatic cancer.

Example 11

Construction of AMIGO2 Detection Reagent Through ELISA

AMIGO2 detection reagents were constructed through ELISA by use of combinations of five anti-AMIGO2 monoclonal antibodies derived from PPZ3133, PPZ3122, PPZ3016, PPZ2956, and PPZ2920, which have a low dissociation constant on the order of $10^{-9}$ as determined in Example 9; i.e., which have high ability to trap AMIGO2.

Each of these five monoclonal antibodies was labeled with peroxidase (POD) by means of Peroxidase Labeling Kit-SH (Dojindo Laboratories) according to a manual (direction for use) attached to the kit.

A purified anti-AMIGO2 monoclonal antibody (5 µg/mL) was dispensed into Maxi sorp 96-well plate (product of Nunc) (100 µL/well), and the plate was allowed to stand at 4° C. overnight for immobilization of the antibody. The wells were washed with PBS containing 0.05% Tween-20 (hereinafter may be referred to as "Tween-PBS"), and 20 mM Tris-HCl, 150 mM NaCl (pH 8.0) containing 40% Block Ace (product of Snow Brand Milk Products Co., Ltd.) (hereinafter may be referred to as "40% BA-TBS") was dispensed into the plate (200 µL/well). Subsequently, the plate was allowed to stand at room temperature for one hour, to thereby block unadsorbed portions on the plate. The wells were washed with Tween-PBS, and then sAMIGO2 protein diluted with 40% BA-TBS to 0.73 ng/mL was dispensed into the plate (100 µL/well), followed by reaction at room temperature for one hour.

The wells were washed with Tween-PBS, and then a peroxidase-labeled anti-AMIGO2 monoclonal antibody diluted with 20 mM Tris-HCl, 150 mM NaCl (pH 8.0) containing 10% Block Ace (product of Snow Brand Milk Products Co., Ltd.) (hereinafter may be referred to as "10% BA-TBS") to 0.1 µg/mL was dispensed into the plate (100 µL/well), followed by reaction at room temperature for one hour. The plate was washed with Tween-PBS, followed by reaction by use of TMB reagent (SCYTEK) in the dark at room temperature for 30 minutes. Thereafter, reaction was terminated by use of STOP solution (SCYTEK), and absorbance was measured at a wavelength of 450 nm by means of a microplate reader. Evaluation was carried out according to the following ratings: A: absorbance of 1.1 or more; B: absorbance of 0.6 or more and less than 1.1; and C: absorbance of less than 0.6 (Table 9).

TABLE 9

Evaluation of combinations of anti-AMIGO2 monoclonal antibodies through ELISA

| Immobilized antibody | Labeled antibody | | | | |
|---|---|---|---|---|---|
| | PPZ2920-POD | PPZ2956-POD | PPZ3016-POD | PPZ3122-POD | PPZ3133-POD |
| PPZ2920 |   | C | A | A | C |
| PPZ2956 | C |   | A | A | C |
| PPZ3016 | B | B |   | C | A |
| PPZ3122 | B | B | C |   | A |
| PPZ3133 | C | C | A | A |   |

Antibody combinations showing "A" in Table 9 were evaluated in terms of reactivity to soluble AMIGO2 contained in a culture supernatant of a pancreatic cancer cell line as described below in Example 12. As a result, a combination of antibodies derived from PPZ3122 and PPZ3133 was found to exhibit the highest reactivity.

Applicants submit that the hybridomas producing the two monoclonal antibodies which had been evaluated as most useful through ELISA were deposited on Sep. 8, 2006 with International Patent Organism Depositary (IPOD), National Institute of Advanced Industrial Science and Technology (AIST), Tsukuba Central 6th, 1-1-1 Higashi, Tsukuba, Ibaraki, Japan, under the terms of the Budapest Treaty; specifically, PPZ3122 (identification number: PPMX0507, accession number: FERM BP-10811) and PPZ3133 (identification number: PPMX0508, accession number: FERM BP-10812), as evidenced by the enclosed Certificates of Deposit and corresponding English translations thereof. Applicants further submit that all restrictions imposed by the depositor on the availability to the public of the deposited biological material of the hybridoma cell lines identified as PPMX0507 and PPMX0508, and deposited as FERM BP-10811 and FERM BP-10812, respectively, will be irrevocably removed upon the granting of a patent on this application.

Example 12

Detection of AMIGO2 in Pancreatic Cancer Cell Lysate or Culture Supernatant Through ELISA On the basis of the results of Example 11, attempts were made to detect AMIGO2 contained in a pancreatic cancer cell lysate or culture supernatant by use of a combination of the PPZ3133-derived antibody (immobilized antibody) and the PPZ3122-derived antibody (peroxidase-labeled antibody).

Cancer cells were grown until nearly confluent, and a cell lysate or a culture supernatant was prepared as described below by use of cells collected on day 4 after confluent cell growth.

A pancreatic cancer cell lysate was prepared by lysing pancreatic cancer cells with an extraction buffer (150 mM sodium chloride, 1% TritonX-100, 2 µg/mL aprotinin, 2 µg/mL pepstatin A, 2 µg/mL leupeptin, 0.87 mg/mL phenylmethanesulfonyl fluoride (PMSF), 10 mM trishydroxyaminomethane hydrochloride (pH 7.4)), and a sample was obtained by 10-fold diluting the cell lysate with 40% BA-TBS. A pancreatic cancer cell culture supernatant was prepared by removing cells through centrifugation (3,000 rpm, 10 minutes), and a sample was obtained by three-fold diluting the supernatant with 40% BA-TBS.

The PPZ3133-derived antibody (5 µg/mL) was dispensed into Maxi sorp 96-well plate (product of Nunc) (100 and the plate was allowed to stand at 4° C. overnight for immobilization of the antibody. The wells were washed with PBS containing 0.05% Tween-20 (hereinafter may be referred to as "Tween-PBS"), and 40% BA-TBS was dispensed into the plate (200 µL/well). Subsequently, the plate was allowed to stand at room temperature for one hour, to thereby block unadsorbed portions on the plate. The wells were washed with Tween-PBS, and then the above-prepared and diluted pancreatic cancer cell lysate or cell culture supernatant was dispensed into the plate (100 µL/well), followed by reaction at room temperature for one hour. The wells were washed with Tween-PBS, and then the peroxidase-labeled PPZ3122-derived antibody diluted with 10% BA-TBS to 0.1 µg/mL was dispensed into the plate (100 µL/well), followed by reaction at room temperature for one hour. The plate was washed with Tween-PBS, followed by reaction by use of TMB reagent in the dark at room temperature for 30 minutes. Thereafter, reaction was terminated by use of STOP solution, and absorbance was measured at a wavelength of 450 nm by means of a microplate reader.

The AMIGO2 concentration of the pancreatic cancer cell lysate or culture supernatant was calculated on the basis of a calibration curve prepared by use of sAMIGO2 protein having a known concentration. The AMIGO2 concentration of the pancreatic cancer cell lysate was calculated as AMIGO2 concentration on the basis of the total protein concentration determined through the Bradford method (using Protein Assay kit (product of Bio-Rad)).

As a result, shown in Table 10, in the case of MIA PaCa2, the AMIGO2 concentration of the cell lysate was equal to or lower than the detection limit, whereas in the case of PK-1, PK-45P, or PK-59, AMIGO2 was detected in the cell lysate at a concentration of 1.9 ng/mg protein, 4.4 ng/mg protein, or 6.7 ng/mg protein, respectively. The concentration data are almost proportional to the expression scores of AMIGO2 mRNA as determined by means of GeneChip U133. In the case of PK-1, PK-45P, or PK-59, AMIGO2 was detected in the cell culture liquid at concentrations of 1.9 ng/mL, 2.9 ng/mL, and 2.4 ng/mL, respectively, however, in the case of MIA PaCa2, the AMIGO2 concentration of the cell culture liquid was equal to or lower than the detection limit. This fact indicates that AMIGO2 expressed on the cell membrane is cleaved by some cause, and is released in the cell culture liquid in the form of soluble AMIGO2. Detection of soluble AMIGO2 in a sample (blood or body fluid) from a subject could be employed for diagnosis of pancreatic cancer.

TABLE 10

AMIGO2 concentration of pancreatic cancer cell lysate or culture supernatant determined through ELISA

| Pancreatic cancer cell line | AMIGO2 concentration of cell lysate (ng/mg protein) | AMIGO2 concentration of culture supernatant (ng/mL) |
|---|---|---|
| MIA PaCa2 | ≦Detection limit | ≦Detection limit |
| PK-1 | 1.9 | 1.9 |
| PK-45P | 4.4 | 2.9 |
| PK-59 | 6.7 | 2.4 |

Example 13

Immunohistological Staining of Pancreatic Cancer

In a preliminary experiment, the pancreatic cancer cell lines PK-45P and Capan-1 were subjected to immunostaining. An anti-AMIGO2 monoclonal antibody which had been found to exhibit reactivity to both or either of the cell lines was employed for immunohistological staining of a clinical sample of pancreatic cancer.

Pancreatic Carcinoma and Normal TMA (both are products of Folio Biosciences, formalin-fixed and paraffin-embedded sample which is mounted as a tissue slice having a thickness of 5 µm) was employed as a sample of pancreatic cancer tissue or normal pancreatic tissue. In details, immunohistological staining was carried out as follows.

A tissue slice was immersed in 100% xylene (five minutes× 3) for deparaffinization, and then immersed in 100% ethanol (one minute×2), 90% ethanol (one minute×1), and 70% ethanol (one minute×1) for hydrophilization. Thereafter, the tissue slice was washed with PBS (20 mM phosphate, 150 mM NaCl, pH 7.0) (five minutes×3), and then immersed in 10 mM citrate buffer (pH 6.0), followed by autoclaving (121° C., 20 minutes) for antigen activation. After antigen activation, the tissue slice was washed with PBS (five minutes×3), followed by reaction in methanol containing 0.3% hydrogen peroxide (room temperature, 15 minutes) for inactivation of peroxidase contained in the tissue slice.

Subsequently, the tissue slice was washed with distilled water (once) and with PBS (five minutes×3), and blocked with TBS (20 mM Tris-HCl, 150 mM NaCl, pH 8.0) containing 40% Block Ace (Snow Brand Milk Products Co., Ltd.) (room temperature, 30 minutes). The tissue slice was washed with PBS (five minutes×3), and then reacted (4° C., overnight) with an anti-AMIGO2 monoclonal antibody which had been diluted with 10% Block Ace-containing TBS to 20 µg/mL. The tissue slice was washed with PBS (five minutes× 3), and then reacted (room temperature, one hour) with peroxidase-labeled anti-mouse IgG (GE Healthcare Bioscience) which had been diluted 200-fold with PBS, the IgG serving as a secondary antibody. The tissue slice was washed with PBS (five minutes×3), followed by color development by use of DAB (3,3'-diaminobenzidine tetrahydrochloride). Hematoxylin was employed for counterstaining of the nucleus.

Figure 9:
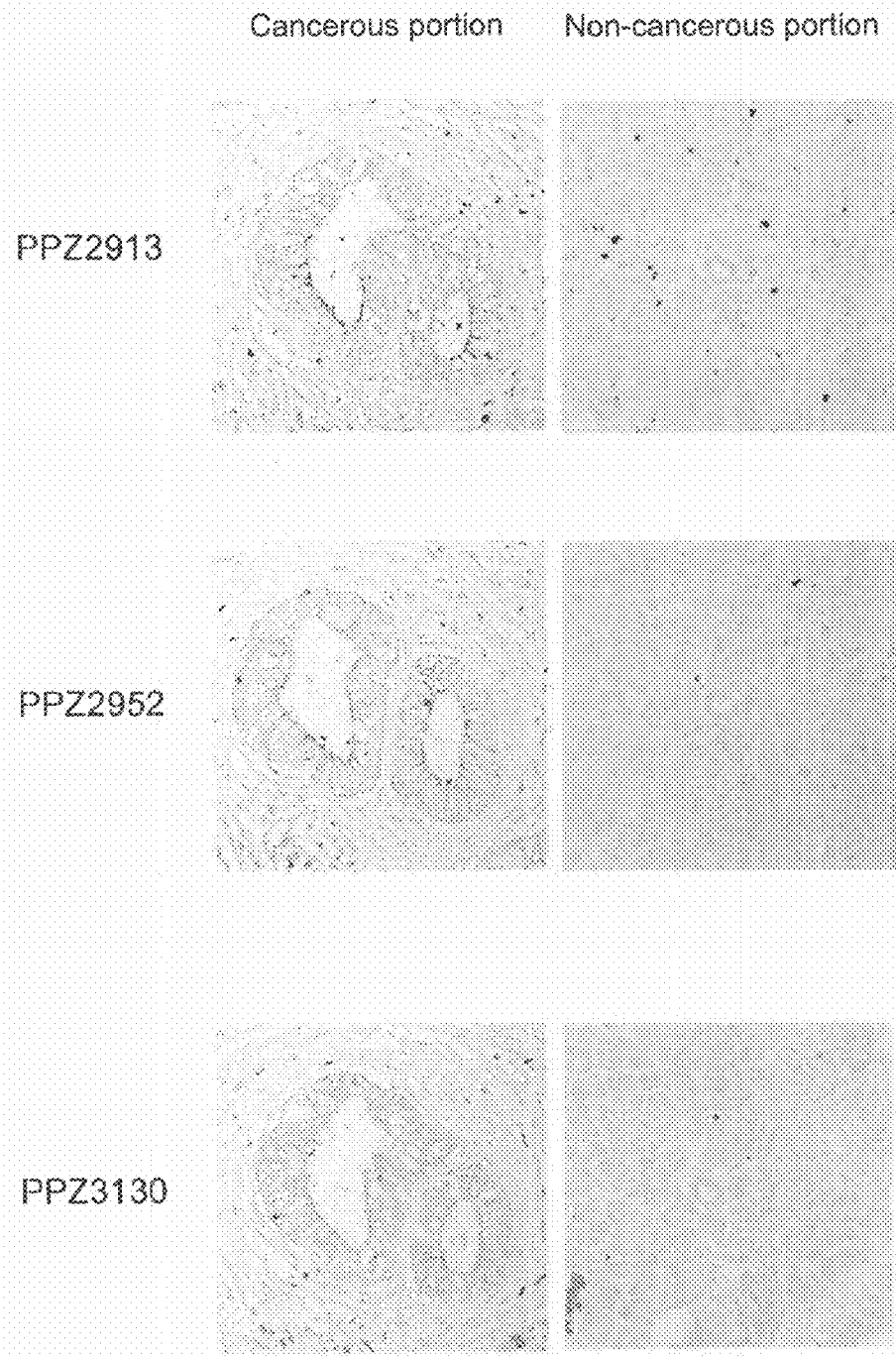
FIG. 9 shows the results of immunohistochemical staining of pancreatic cancer tissue by use of anti-AMIGO2 antibodies.

As is clear from FIG. 9, AMIGO2 highly expressed in pancreatic cancer tissue is specifically immunostained by use of three antibodies derived from PPZ2913, PPZ2952, and PPZ3130. Sixty-six pancreatic cancer tissue samples spotted on a tissue array were evaluated in terms of level of AMIGO2 expression. Evaluation was carried out on the basis of the degree of staining with Histofine HER2 kit according to the following four ratings (scores).

Score 0: No AMIGO2-positive cells are present in tumor cells in a tissue sample, or AMIGO2-positive cells account for less than 10% of the tumor cells. Score 1+: AMIGO2-positive cells account for 10% or more of tumor cells in a tissue sample, and weak staining is localized to a portion of tumor cell membranes. Score 2+: AMIGO2-positive cells account for 10% or more of tumor cells in a tissue sample, and moderate staining is localized to tumor cell membranes. Score 3+: AMIGO2-positive cells account for 10% or more of tumor cells in a tissue sample, and strong staining is localized to tumor cell membranes.

The 66 pancreatic cancer tissue samples were classified according to the aforementioned scores as follows: 24 samples with score 0 (36%); 28 samples with score 1+ (42%); 9 samples with score 2+ (14%); and 5 samples with score 3+ (8%).

When samples with score 1+ or higher are regarded as staining-positive samples, the number of staining-positive samples is 42 (positive rate: 64%). When, more strictly, samples with score 2+ to score 3+ are regarded as AMIGO2-overexpressing samples, the number of AMIGO2-overexpressing samples is 14 (positive rate: 21%).

Applicants submit that PPZ2913, PPZ2952, and PPZ3130 were deposited on Sep. 27, 2006 with International Patent Organism Depositary (IPOD), National Institute of Advanced Industrial Science and Technology (AIST), Tsukuba Central 6th, 1-1-1 Higashi, Tsukuba, Ibaraki, Japan; specifically, PPZ2913 (identification number: PPMX0509, accession number: FERM P-21037), PPZ2952 (identification number: PPMX0510, accession number: FERM P-21038), and PPZ3130 (identification number: PPMX0511, accession number: FERM P-21039), as evidenced by the enclosed Certificates of Deposit and corresponding English translations thereof.

Example 14

Cytotoxic Activity (ADCC Activity) of Anti-AMIGO2 Antibody to Full-Length-AMIGO2-Expressing CHO Clone (EXZ1005)

ADCC activity was determined through a method employing, as an index, release of lactate dehydrogenase (LDH) contained in a target cell. Specifically, as described below, ADCC activity was determined by means of CytoTox96 Non-Radioactive Cytotoxicity Assay Kit (product of Promega) according to a protocol attached to the kit.

Preparation of Effector Cell

A spleen was removed from each male C3H mouse (eight weeks old, Saitama Experimental Animals Supply Co., Ltd.), and spleen cells are isolated in an RPMI 1640 medium containing 10% FBS. Spleen cells were washed with the same medium, and then the cell concentration was regulated to $5 \times 10^6$ cells/mL, followed by culturing for five days in the presence of 500 U/mL human IL-2 (product of PEPROTECHEC) and 10 ng/mL mouse GM-CSF (product of PEPROTECHEC). On the day of determination of ADCC activity, spleen cells were recovered and washed with a DMEM medium containing 5% FBS (containing no Phenol Red), and then the cell concentration was regulated to $1.25 \times 10^7$ cells/mL in the same medium, whereby an effector cell was prepared.

Preparation of Target Cell

A full-length-AMIGO2-expressing CHO clone (EXZ1005) was employed as a target cell. Cells of EXZ1005 were removed from a plate, and then suspended in a 5% FBS-containing DMEM medium (containing no Phenol Red). The suspension was dispensed into a 96-well U-bottomed plate (product of Becton Dickinson) (30 μL/well, $2 \times 10^4$ cells/well).

Determination of ADCC Activity

An antibody solution (concentration: 2.4 μg/mL) was added to the target cell (10 μL/well), followed by incubation for 30 minutes. Subsequently, the effector cell was dispensed into the plate (40 μL/well), followed by culturing in a carbon dioxide gas incubator for four hours. After completion of culturing, a supernatant (50 μL) was recovered, and transferred to a flat-bottomed enzymatic assay plate. A substrate mixture attached to the kit was added to the plate (50 μL/well), followed by incubation under light shielding conditions at room temperature for 30 minutes. After completion of incubation, a reaction-terminating liquid was added to the plate (50 μL/well), and absorbance was measured at a wavelength of 490 nm by means of a microplate reader.

Cytotoxic activity can be determined as follows.

$$\text{Cytotoxic activity}(\%)=(A-B-C)/(D-C)\times 100$$

A: [absorbance corresponding to a sample]−[background absorbance of a culture liquid]

B: [absorbance attributed to LDH derived from the effector cell]−[background absorbance of the culture liquid]

C: [absorbance attributed to LDH which has been naturally released from the target cell]−[background absorbance of the culture liquid]

D: [absorbance attributed to LDH which has been 100% released from the target cell through addition of 0.9% Triton-X100]−[background absorbance of the culture liquid]

The results are shown in Table 11. In Table 11, "Negative control" refers to an antibody which has previously been found to exhibit no reactivity to AMIGO2. In contrast to the negative control antibody, which exhibited an ADCC activity of 3.2%, four antibodies derived from the following hybridomas (PPZ2952, PPZ3122, PPZ3133, and PPZ3145) exhibited a high ADCC activity of 20% or more.

Applicants submit that the hybridomas producing these four antibodies (PPZ2952, PPZ3122, PPZ3133, and PPZ3145) were deposited with International Patent Organism Depositary (IPOD), National Institute of Advanced Industrial Science and Technology (AIST), Tsukuba Central 6th, 1-1-1 Higashi, Tsukuba, Ibaraki, Japan on Sep. 27, 2006 for PPZ2952 and PPZ3145, and on Sep. 8, 2006 for PPZ3122 and PPZ3133; specifically, PPZ2952 (identification number: PPMX0510, accession number: FERM P-21038), PPZ3122 (identification number: PPMX0507, accession number: FERM BP-10811), PPZ3133 (identification number: PPMX0508, accession number: FERM BP-10812), and PPZ3145 (identification number: PPMX0519, accession number: FERM BP 10813), as evidenced by the enclosed Certificates of Deposit and corresponding English translations thereof. The hybridoma cell lines identified as PPMX0507, PPMX0508 and PPMX0519 were deposited as FERM BP-10811, FERM BP-10812 and FERM BP-10813, respectively, under the terms of the Budapest Treaty. Applicants further submit that all restrictions imposed by the depositor on the availability to the public of the deposited biological material of the hybridoma cell lines identified as PPMX0507, PPMX0508 and PPMX0519, and deposited as FERM BP-10811, FERM BP-10812 and FERM BP-10813, respectively, will be irrevocably removed upon the granting of a patent on this application.

TABLE 11

| No. | Clone number | ADCC activity (%) |
|---|---|---|
| 1 | PPZ2904 | 13.1 |
| 2 | PPZ2912 | 13.7 |
| 3 | PPZ2913 | 9.9 |
| 4 | PPZ2919 | 15.4 |
| 5 | PPZ2920 | 18.0 |
| 6 | PPZ2936 | 18.9 |
| 7 | PPZ2937 | 18.0 |
| 8 | PPZ2952 | 27.0 |
| 9 | PPZ2956 | 18.0 |
| 10 | PPZ3003 | 13.3 |
| 11 | PPZ3016 | 17.9 |
| 12 | PPZ3122 | 20.3 |
| 13 | PPZ3124 | 16.7 |
| 14 | PPZ3125 | 15.2 |
| 15 | PPZ3130 | 15.4 |
| 16 | PPZ3133 | 22.8 |
| 17 | PPZ3135 | 14.5 |
| 18 | PPZ3145 | 22.0 |
| 19 | PPZ3148 | 16.6 |
| 20 | PPZ3160 | 17.7 |
| — | Negative control | 3.6 |

Anti-AMIGO2 monoclonal antibodies applicable to various purposes were prepared. In addition to full-length AMIGO2 protein, partial peptides thereof were expressed in mammalian CHO cells and budding baculovirus, and employed as antigens for immunization and screening. As a result, as shown in Table 12, antibodies applicable to various purposes were selected. As is clear from Table 12, difficulty is encountered in selecting an antibody applicable to all the purposes, and selection of an antibody applicable to a purpose requires a screening method corresponding to the purpose.

Example 15

Implantation of Pancreatic Cancer Cell into Scid Mouse and Immunostaining of Formed Tumor Mass Cells of the pancreatic cancer cell line PK-45P were subcutaneously implanted into the right abdomen of female CB17-scid mice (seven weeks old) ($1 \times 10^7$ cells/mouse). Thirty-four days after implantation, tumor mass was removed from each mouse, and then embedded in OTC compound, followed by preparation of frozen sections. Each of the thus-prepared frozen sections was washed with PBS (20 mM phosphate, 150 mM NaCl, pH 7.0) (five minutes×3), and then immersed in 10 mM citrate buffer (pH 6.0), followed by autoclaving (121° C., 20 minutes) for activation of the antigen.

After activation of the antigen, the section was washed with PBS (five minutes×3), followed by reaction in methanol containing 0.3% hydrogen peroxide (room temperature, 15 minutes) for inactivation of peroxidase contained in the section. Subsequently, the section was washed with distilled water (once) and with PBS (five minutes×3), and blocked with TBS (20 mM Tris-HCl, 150 mM NaCl, pH 8.0) containing 40% Block Ace (Snow Brand Milk Products Co., Ltd.) (room temperature, 30 minutes). The section was washed with PBS (five minutes×3), and then reacted (4° C., overnight) with an anti-AMIGO2 monoclonal antibody which had been diluted with 10% Block Ace-containing TBS to 20 μg/mL. The section was washed with PBS (five minutes×3), and then reacted (room temperature, one hour) with peroxidase-labeled anti-mouse IgG (GE Healthcare Bioscience) which had been

TABLE 12

List of anti-AMIGO2 monoclonal antibodies applicable to various purposes

| | | Western blotting | | | | Dissociation constant (unit: M) | Sandwich ELISA | CDC activity (%) | | ADCC activity (%) | Immunostaining | | |
|---|---|---|---|---|---|---|---|---|---|---|---|---|---|
| | | sAMIGO2 | | AMIGO2-Ig | | | | | | | Cultured cell | | Tissue array Human pancreatic cancer tissue |
| Clone number | Subclass | Non-reducing | Reducing | Non-reducing | Reducing | | | EXZ1005 | PK-45P | EXZ1005 | PK-45P | Capan-1 | |
| PPZ2904 | G2a | + | + | + | + | 3.00E−08 | − | 85.0 | 7.2 | 13.1 | ± | − | − |
| PPZ2912 | G2a | + | + | + | + | 1.60E−08 | − | 79.7 | 7.0 | 13.7 | − | − | (NT) |
| PPZ2913 | G2b | + | + | + | + | ND | − | 85.9 | 4.8 | 9.9 | ± | + | + |
| PPZ2919 | G2a | − | − | − | − | 2.00E−08 | − | 90.9 | 18.4 | 15.4 | (NT) | (NT) | (NT) |
| PPZ2920 | G1 | − | − | − | − | 9.80E−09 | + | 2.2 | 6.3 | 18.0 | − | − | (NT) |
| PPZ2936 | G1 | + | + | + | + | 2.70E−08 | − | 4.4 | 6.3 | 18.9 | − | − | (NT) |
| PPZ2937 | G2a | − | − | − | − | 4.50E−08 | − | 93.0 | 13.1 | 18.0 | (NT) | (NT) | (NT) |
| PPZ2952 | G1 | + | + | + | + | ND | − | 3.6 | 6.3 | 27.0 | + | + | + |
| PPZ2956 | G1 | − | − | − | − | 9.00E−09 | + | 4.2 | 7.1 | 18.0 | (NT) | (NT) | (NT) |
| PPZ3003 | G2a | − | − | − | − | 5.90E−08 | − | 96.9 | 12.6 | 13.3 | (NT) | (NT) | (NT) |
| PPZ3016 | G2a | + | + | + | + | 7.90E−09 | + | 79.4 | 4.9 | 17.9 | − | − | (NT) |
| PPZ3122 | G2a | + | + | + | + | 3.50E−09 | ++ | 78.3 | 7.8 | 20.3 | + | ± | − |
| PPZ3124 | G2a | − | − | − | − | 3.00E−08 | − | 100.0 | 26.2 | 16.7 | (NT) | (NT) | (NT) |
| PPZ3125 | G2a | − | − | − | − | 5.10E−08 | − | 79.9 | 17.1 | 15.2 | (NT) | (NT) | (NT) |
| PPZ3130 | G2a | + | + | − | − | ND | − | 73.4 | 5.8 | 15.4 | + | + | + |
| PPZ3133 | G1 | − | − | − | − | 2.60E−09 | ++ | 5.7 | 5.5 | 22.8 | − | − | (NT) |
| PPZ3135 | G2a | − | − | − | − | 4.70E−08 | − | 78.8 | 24.8 | 14.5 | (NT) | (NT) | (NT) |
| PPZ3145 | G1 | − | − | − | − | 6.20E−08 | − | 5.3 | 6.9 | 22.0 | (NT) | (NT) | (NT) |
| PPZ3148 | G2a | − | − | − | − | 4.60E−08 | − | 83.4 | 33.7 | 16.6 | (NT) | (NT) | (NT) |
| PPZ3160 | G1 | − | − | − | − | 2.10E−08 | − | 3.6 | 7.2 | 17.7 | (NT) | (NT) | (NT) |

"ND" represents the case where dissociation constant is equal to or lower than the detection limit.
In addition, for example, "3.0E−08" corresponds to a dissociation constant of $3.0 \times 10^{-8}$.
The symbols "+" and "−" respectively represent the case where reactivity is present and the case where reactivity is absent.

diluted 200-fold with PBS, the IgG serving as a secondary antibody. The section was washed with PBS (five minutes×3), followed by color development by use of DAB (3,3'-diaminobenzidine tetrahydrochloride). Hematoxylin was employed for counterstaining of the nucleus.

Figure 10:
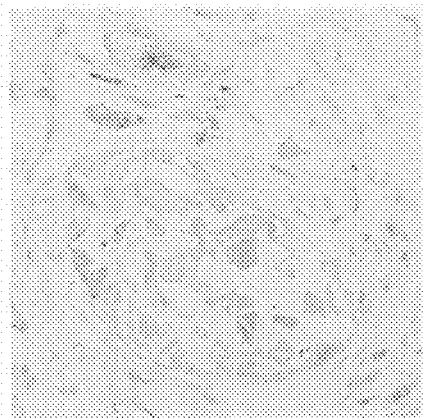
FIG. 10 shows the results of immunostaining of tumor mass formed by implantation of pancreatic cancer cell lines into a scid mouse.

The results are shown in FIG. 10. The pancreatic cancer cell line PK-45P implanted into scid mice was found to maintain expression of AMIGO2 even after subcutaneous tumor formation in mice. The degree of immunostaining was determined to be score 1+ according to the criteria (ratings) described in Example 13.

Example 16

Test of Inhibition of Engraftment or Growth of Pancreatic Cancer Cell Line in Scid Mouse Cells of the pancreatic cancer cell line PK-45P, which, as described in Example 15, had been found to maintain expression of AMIGO2 (score 1+) even after subcutaneous implantation in scid mice, were subcutaneously implanted into the right abdomen of female scid mice (seven weeks old) ($2 \times 10^6$ cells/mouse). An antibody was administered to each mouse via the tail vein at intervals of three days from day 0 (i.e., the day of implantation) to day 15 (total: six administrations). At intervals of two or three days until day 38, engraftment of the pancreatic cancer cell line was confirmed (through palpation), and the volume of tumor mass was measured after engraftment (the major axis length (L) and minor axis length (W) of tumor mass were measured via the skin by means of a vernier caliper, and the tumor volume (V) was calculated by use of the formula: $V=LW^2/2$ (unit: $mm^3$)).

Three anti-AMIGO2 monoclonal antibodies derived from PPZ2952, PPZ3122, and PPZ3148 exhibiting CDC activity and/or ADCC activity were selected as antibodies for administration.

The subclass of the PPZ2952-derived antibody is IgG1, and the subclass of the PPZ3122- or PPZ3148-derived antibody is IgG2a. Therefore, antibodies corresponding to the respective subclasses (i.e., 3423 (subclass: IgG1) and K7124 (subclass: IgG2a)) were also administered as negative control antibodies which do not react with the implanted PK-45P. These antibodies were administered to groups of mice (10 mice for each group), and the dose of each antibody per administration was determined to be 25 mg/kg on the basis of the body weights of the mice.

Figure 11:
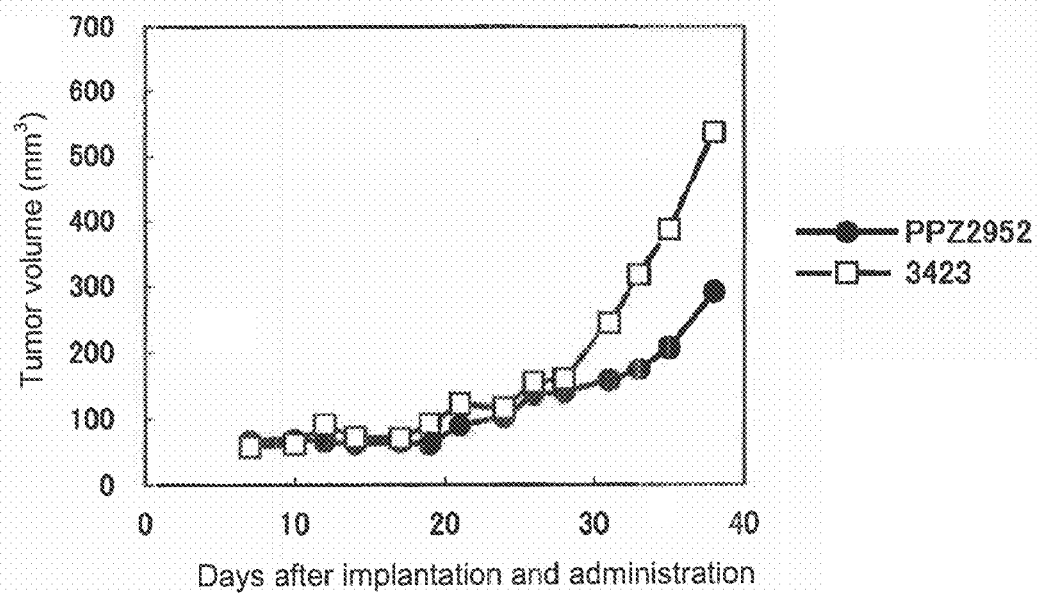
FIG. 11 shows the results of a test of anti-AMIGO2 monoclonal antibodies (subclass: IgG1) for inhibition of tumor engraftment and growth in scid mice implanted with pancreatic cancer cell lines.
Figure 12:
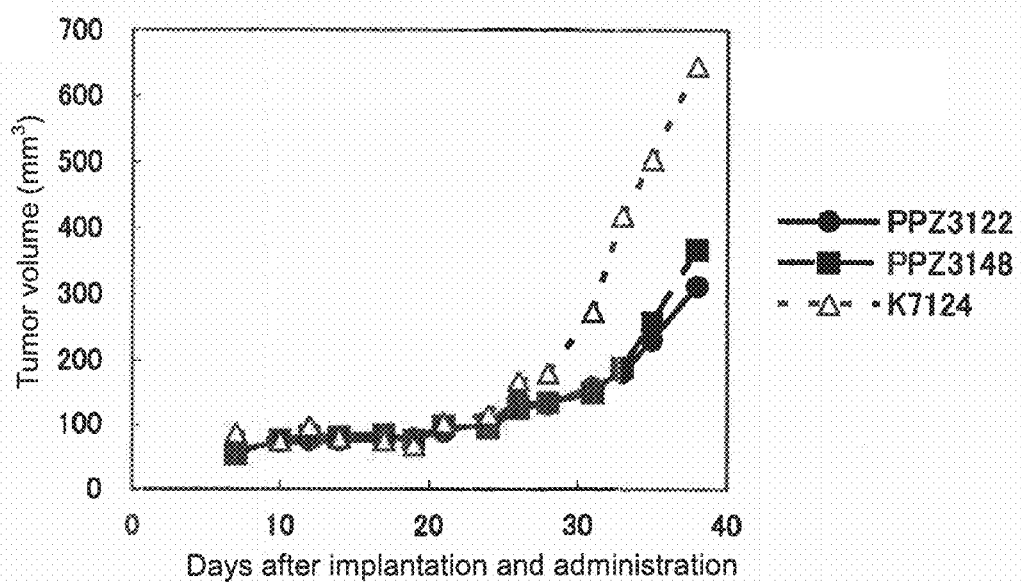
FIG. 12 shows the results of a test of anti-AMIGO2 monoclonal antibodies (subclass: IgG2a) for inhibition of tumor engraftment and growth in scid mice implanted with pancreatic cancer cell lines.

FIG. 11 shows the results of the test employing the antibodies (subclass: IgG1), and FIG. 12 shows the results of the test employing the antibodies (subclass: IgG2a). In each of the test groups, tumor engraftment was confirmed during the period of antibody administration (i.e., day 0 to day 15). However, as shown in data regarding an increase in tumor volume after antibody administration, the antibody derived from PPZ2952, PPZ3122, or PPZ3148 exhibited a better tumor growth inhibitory effect, as compared with the negative control antibody 3423 or K7124. As described in Examples 13 and 15, immunostaining score was 1+ in the case where PK-45P was implanted into scid mice and tumor mass was formed, whereas pancreatic cancer tissue samples (clinical samples) with immunostaining score of 1+ or higher accounted for 64% or more of all the tested samples. These data indicate that the antibody derived from PPZ2952, PPZ3122, or PPZ3148 is envisaged to exhibit a pancreatic cancer therapeutic effect in cancer patients in whom AMIGO2 is highly expressed.

Example 17

Test of Inhibition of Engraftment or Growth, in Scid Mouse, of Pancreatic Cancer Cell Line Forcedly Expressing AMIGO2

(1) Preparation of Pancreatic Cancer Cell Line Forcedly Expressing AMIGO2

According to the protocol of FuGENE HD transfection reagent (product of Roche Diagnostics), the pancreatic cancer cell line MIA PaCa2 was transfected with the full-length AMIGO2 expression vector pEF4/AMIGO2 full prepared in Example 3 (1). Specifically, on the day before transfection, $8 \times 10^5$ MIA PaCa2 cells were inoculated onto a dish (diameter: 35 mm), followed by culturing overnight. On the following day, the expression vector pEF4/AMIGO2 full (3 μg) and the FuGENE HD reagent (6 μL) were mixed with serum-free Opti-MEM medium (product of Invitrogen) (150 μL), followed by incubation at room temperature for 15 to 45 minutes. Thereafter, the resultant product was added to the cell culture liquid for transfection. On the day following transfection, cloning was initiated through limiting dilution by use of Zeocin (product of Invitrogen) serving as a selection reagent.

Figure 13:
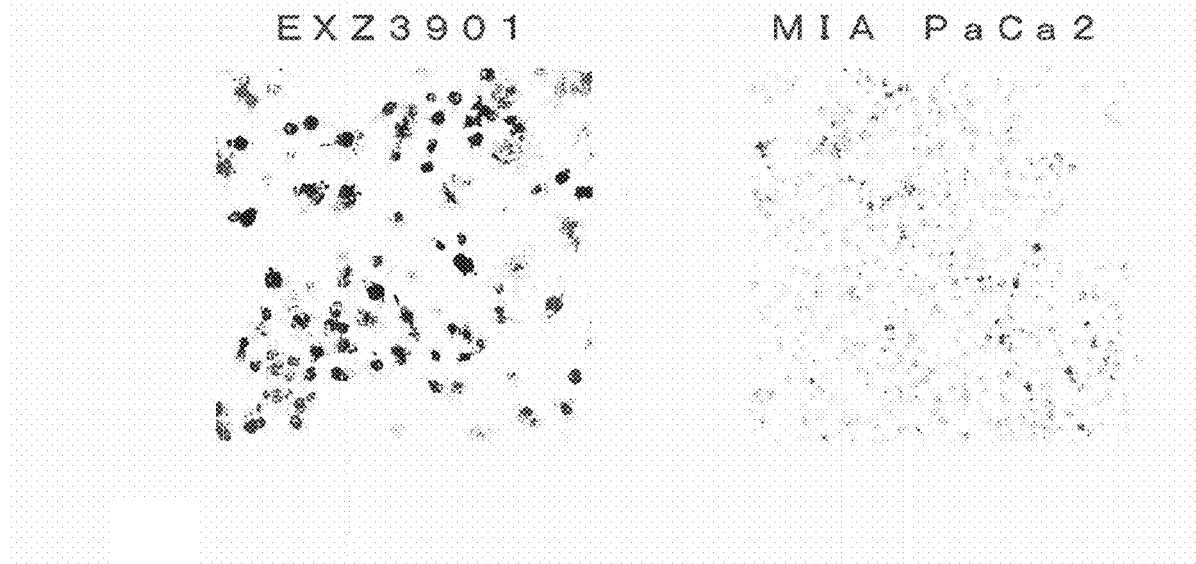
FIG. 13 shows the results of immunostaining of AMIGO2 expressed by AMIGO2-forcedly-expressing pancreatic cancer cell lines MIA PaCa2 or wild-type MIA PaCa2.

Screening of full-length-AMIGO2-expressing MIA PaCa2 cells was carried out through western blotting employing an anti-AMIGO2 monoclonal antibody (product of R & D Systems), flow cytometry (by means of FACScalibur (product of Becton Dickinson)), and immunostaining employing an anti-AMIGO2 antibody, to thereby select a well-grown clone exhibiting a strong signal; i.e., a full-length-AMIGO2-expressing MIA PaCa2 clone (EXZ3901). The expression level of AMIGO2 protein was examined through immunostaining. As shown in FIG. 13, the level of AMIGO2 protein expressed by EXZ3901 was considerably higher than that of AMIGO2 protein expressed by wild-type MIA PaCa2.

(2) Implantation of AMIGO2-Forcedly-Expressing Pancreatic Cancer Cell Line into Scid Mouse Cells of the above-prepared full-length-AMIGO2-expressing MIA PaCa2 clone (EXZ3901) or wild-type MIA PaCa2 cell line were subcutaneously implanted into the right abdomen of female scid mice (seven weeks old) ($1 \times 10^7$ cells/mouse).

(3) Measurement of Tumor Mass Size and Serum AMIGO2 Protein Concentration in Scid Mouse In order to determine tumor mass size and serum AMIGO2 protein concentration in scid mice after implantation of the pancreatic cancer cell line, on day 10, tumor mass was removed from two scid mice implanted with the full-length-AMIGO2-expressing MIA PaCa2 clone (EXZ3901) or wild-type MIA PaCa2 cell line, and serum was collected from the mice. The removed tumor mass was classified according to its size (i.e., major axis length as measured by means of a scale); specifically, "small" (major axis length: less than 3 mm), "middle" (major axis length: 3 mm or more and less than 6 mm), and "large" (major axis length: 6 mm or more). AMIGO2 protein contained in mouse serum was detected through ELISA as described in Example 11. The results are summarized in Table 13. In the individual mice implanted with the full-length-AMIGO2-expressing MIA PaCa2 clone (EXZ3901), AMIGO2 protein was detected in serum at a concentration proportional to tumor size. In contrast, in the individual mice implanted with the wild-type MIA PaCa2 cell line, AMIGO2 protein was not detected at all in serum, although the size of tumor mass was sufficiently large. Conceivably, detection of AMIGO2 protein in serum from EXZ3901-implanted mice is attributed to release of AMIGO2 protein from EXZ3901-induced tumor mass into blood by some cause.

TABLE 13

Removed tumor mass size and serum AMIGO2 concentration in cancer-bearing mice

| Individual mouse number | Implanted cell line | Removed tumor mass size | Serum AMIGO2 concentration in mouse (ng/mL) |
|---|---|---|---|
| 1 | EXZ3901 | Large | 9.0 |
| 2 | EXZ3901 | Middle | 1.8 |
| 3 | Wild-type MIA PaCa2 | Large | 0.0 |
| 4 | Wild-type MIA PaCa2 | Middle | 0.0 |

(4) Test of Inhibition of Engraftment or Growth, in Scid Mouse, of Pancreatic Cancer Cell Line Forcedly Expressing AMIGO2

Cancer-bearing mouse models were prepared in a manner similar to that described above in Example 17 (2). An antibody was administered to each mouse via the tail vein at intervals of three days from day 0 (i.e., the day of implantation) to day 27 (total: 10 administrations). At intervals of three or four days until day 42, engraftment of the pancreatic cancer cell line was confirmed (through palpation), and the volume of tumor mass was measured after engraftment (the major axis length (L) and minor axis length (W) of tumor mass were measured via the skin by means of a vernier caliper, and the tumor volume (V) was calculated by use of the formula: $V=LW^2/2$ (unit: $mm^3$)).

Two anti-AMIGO2 monoclonal antibodies derived from PPZ3124 and PPZ3148 exhibiting CDC activity and/or ADCC activity were selected as antibodies for administration.

The subclass of the PPZ3124- or PPZ3148-derived antibody is IgG2a. Therefore, an antibody corresponding to the subclass (i.e., K7124 (subclass IgG2a)) was also administered as a negative control antibody which does not react with the implanted full-length-AMIGO2-expressing MIA PaCa2 clone (EXZ3901). These antibodies were administered to groups of mice (10 mice for each group), and the dose of each antibody per administration was determined to be 75 mg/kg on the basis of the body weights of the mice.

Figure 14:
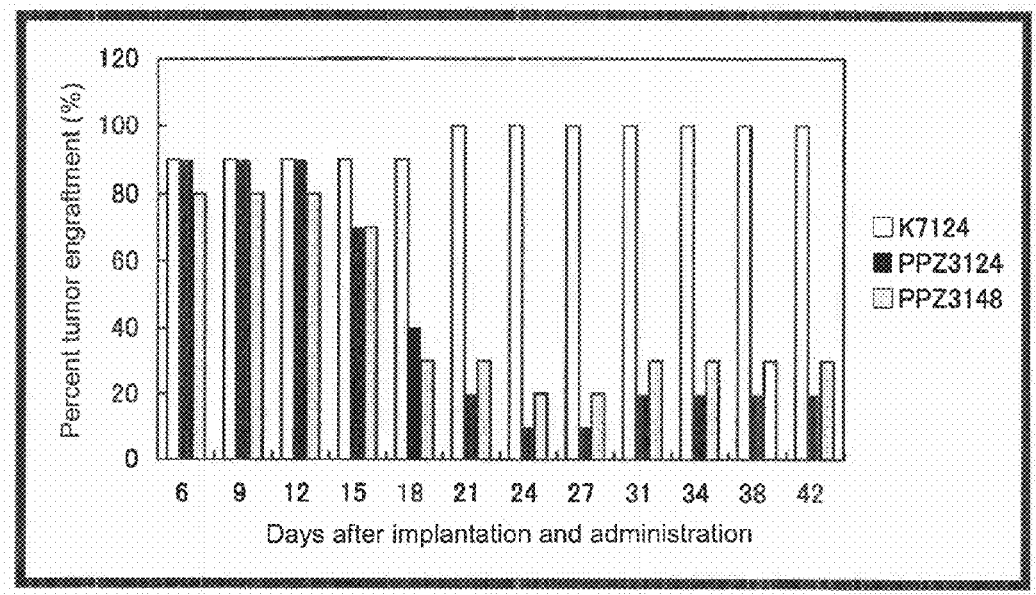
FIG. 14 shows the results of evaluation of the tumor engraftment inhibitory effect of anti-AMIGO2 monoclonal antibodies in scid mice implanted with the AMIGO2-forcedly-expressing pancreatic cancer cell lines.

FIG. 14 shows data of percent tumor engraftment in the antibody administration groups. In each of the antibody administration groups, the percent engraftment of the full-length-AMIGO2-expressing MIA PaCa2 clone (EXZ3901) was 80 to 90% until 12 days after implantation. However, in the PPZ3124- or PPZ3148-derived antibody administration group, the percent engraftment of EXZ3901 was gradually reduced thereafter, and the percent engraftment remained at 20 to 30% even after administration of the antibody (i.e., day 31 or later). In contrast, in the K7124 (negative control) administration group, the percent engraftment of EXZ3901 reached 100% on day 21 (i.e., during the antibody administration period).

Figure 15:
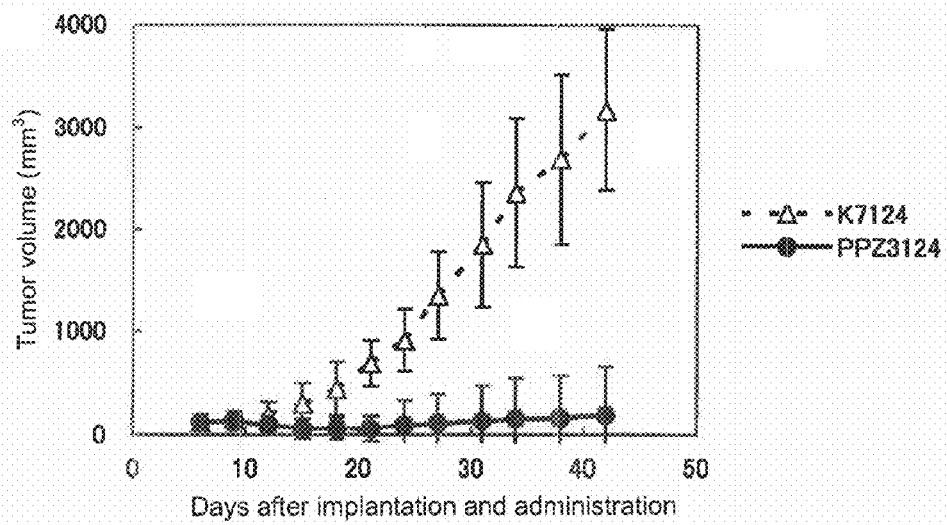
FIG. 15 shows the results of evaluation of the tumor growth inhibitory effect of an anti-AMIGO2 monoclonal antibody (PPZ3124-derived antibody) in scid mice implanted with the AMIGO2-forcedly-expressing pancreatic cancer cell lines.

FIG. 15 shows change in average tumor volume±SD after engraftment in the case of administration of PPZ3124, and FIG. 16 shows change in average tumor volume±SD after engraftment in the case of administration of PPZ3148. A difference in average tumor volume between the test antibody (PPZ3124- or PPZ3148-derived antibody) administration group and the negative control antibody (K7124) administration group was determined by the Wilcoxon rank sum test on days of tumor volume measurement. As a result, a significant difference ($p<0.01$) was observed in average tumor volume between the K7124 administration group and the PPZ3124-derived antibody administration group on day 12 or later, or between the K7124 administration group and the PPZ3148-derived antibody administration group on day 15 or later.

Example 18

Determination of Accumulation of Antibody in Tumor of Cancer-Bearing Mouse Through In Vivo Near-Infrared Fluorescence Imaging (1) Labeling of Antibody with Fluorescent Substance A solution (2.5 µL) of 25 mM DY-676-NHS-Ester (product of Dyomics) in N,N-dimethylformamide was added under stirring to a solution (1 mL) of an anti-AMIGO2 monoclonal antibody (PPZ3124-derived antibody) (concentration: 5 mg/mL) which had been prepared by use of 50 mM sodium hydrogencarbonate buffer (pH 8.5) containing 0.5 M NaCl, followed by reaction in the dark at room temperature for one hour (ratio by mole of PPZ3124 to DY-676=1:2). The entire reaction mixture was applied to PD-10 column (product of GE Healthcare Bioscience) which had been equilibrated in advance with 20 mM sodium phosphate buffer (pH 7.2) containing 150 mM NaCl, and a fraction containing eluted antibody was pooled. The fraction was concentrated so as to attain an antibody concentration of 5 mg/mL through ultrafiltration. The number of DY-676 (fluorescent substance) molecules bound to one PPZ3124-derived antibody molecule was calculated to be 0.8 by use of the molar extinction coefficient of the antibody at a wavelength of 280 nm (220,000 $M^{-1}cm^{-1}$) and the molar extinction coefficient of DY-676 at a wavelength of 674 nm (145,000 $M^{-1}cm^{-1}$).

In a manner similar to that described above, the negative control antibody K7124 was also labeled with DY-676. The number of DY-676 molecules bound to one K7124 antibody molecule was found to be 0.9.

(2) In Vivo Imaging

Cells of the pancreatic cancer cell line PK-45P were subcutaneously implanted into the right abdomen of female scid mice (seven weeks old) ($2 \times 10^6$ cells/mouse), to thereby prepare cancer-bearing mice. The above-prepared DY-676-labeled PPZ3124-derived antibody or DY-676-labeled K7124 (concentration: 5 mg/mL) (0.1 mL) was administered to each mouse via the tail vein. Forty-eight hours after administration of the fluorescent-substance-labeled antibody, pentobarbital was injected into the peritoneal cavity of each mouse, and, under anesthesia, fluorescence imaging data were collected by means of LAS-3000 (Fuji Film) equipped with a near-infrared-excited fluorescence detection unit.

FIG. 17(a) shows fluorescence imaging data from a mouse which received the DY-676-labeled PPZ3124-derived antibody, and FIG. 17(b) shows fluorescence imaging data from a mouse which received the DY-676-labeled K7124. In FIG. 17, each white dashed circle corresponds to a site where tumor is present. In a cancer-bearing mouse which received the DY-676-labeled PPZ3124-derived antibody, accumulation of the antibody in tumor was observed. In contrast, in a mouse which received the DY-676-labeled K7124 (negative control), fluorescence was not detected at a tumor site. These data indicate that accumulation of the DY-676-labeled PPZ3124-derived antibody is attributed to specific binding of the PPZ3124-derived antibody to AMIGO2 protein expressed on tumor cells. Thus, these data indicate that intravenous administration of a fluorescent-substance-labeled anti-AMIGO2 antibody (PPZ3124-derived antibody) to a cancer-bearing mouse realizes specific imaging of AMIGO2-expressing tumor.

Example 19

Intracellular Transfer of AMIGO2 Protein Through Antibody Binding (1) Labeling of Antibody with Fluorescent Substance A solution (1.7 µL) of 5 mg/mL Alexa Fluor 488 Succinimidyl Ester (Molecular Probes) in dimethylformamide was added under stirring to a solution (365 µL) of an anti-AMIGO2 monoclonal antibody (PPZ3124-derived antibody) (concentration: 5 mg/mL) which had been prepared by use of 50 mM sodium hydrogencarbonate buffer (pH 8.5) containing 0.5 M NaCl, followed by reaction in the dark at room temperature for one hour (ratio by mole of PPZ3124 to Alexa Fluor 488=1:2). The entire reaction mixture was applied to PD-10 column (product of GE Healthcare Bioscience) which had been equilibrated in advance with 20 mM sodium phosphate buffer (pH 7.2) containing 150 mM NaCl, and a fraction containing eluted antibody was pooled. The fraction was concentrated so as to attain an antibody concentration of 1 mg/mL through ultrafiltration. The number of Alexa Fluor 488 (fluorescent substance) molecules bound to one PPZ3124-derived antibody molecule was calculated to be 0.8 by use of the molar extinction coefficient of the antibody at a wavelength of 280 nm (220,000 $M^{-1}$ $cm^{-1}$) and the molar extinction coefficient of Alexa Fluor 488 at a wavelength of 495 nm (71,000 $M^{-1}$ $cm^{-1}$).

Figure 18:
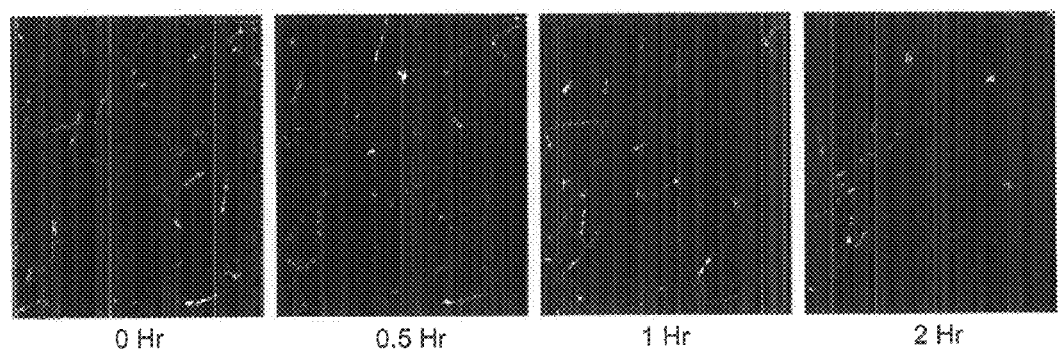
FIG. 18 shows the results of determination of endocytosis of an anti-AMIGO2 monoclonal antibody through binding of the antibody to AMIGO2 present on the surfaces of cell membranes.

(2) Determination of Intracellular Transfer of Antibody-Bound AMIGO2 Protein Through Confocal Laser Microscopy Cells of the full-length-AMIGO2-expressing CHO clone (EXZ1005) prepared in Example 3 (3) were inoculated ($5 \times 10^5$ cells) into Glass Base Dish (diameter: 35 mm, product of IWAKI), followed by culturing for two days. Thereafter, the medium was discarded, and 10% FBS-containing F-12 HAM medium (200 µL) containing the above-prepared Alexa-Fluor-488-labeled PPZ3124-derived antibody (concentration: 20 µg/mL) was added to the cells, followed by incubation at room temperature for five minutes. Subsequently, the cells were washed with 10% FBS-containing F-12 HAM medium, and the same medium was added in an amount of 200 µL, followed by collection of data over time (0, 0.5, 1, and 2 hours) by means of a confocal laser microscope (inverted IX81, product of Olympus Corporation) (excitation wavelength: 488 nm/fluorescence wavelength: 519 nm). Fluorescence signals localized to cell membrane surfaces immediately after reaction were observed to transfer into cells as time elapsed (FIG. 18). This indicates that when the antibody (PPZ3124-derived antibody) binds to AMIGO2 present on the surface of a cell membrane, the resultant AMIGO2-antibody complex is incorporated into the cell through endocytosis.

Example 20

Figure 19:
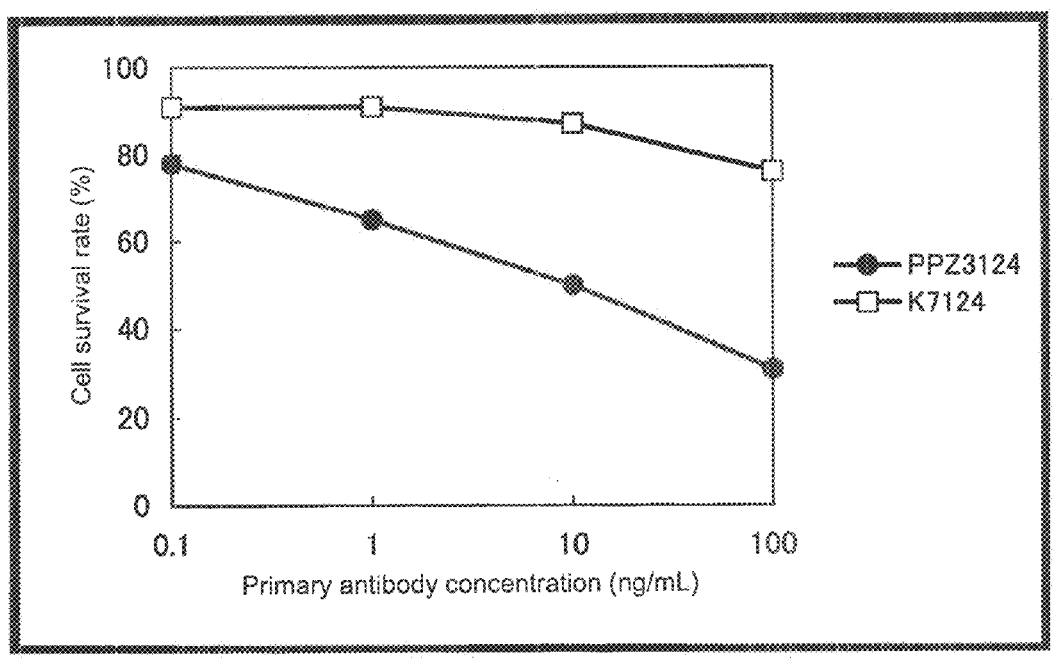
FIG. 19 shows the results of examination of the AMIGO2-expressing cell growth inhibitory effect of an antibody conjugated with a substance having cytotoxic activity.

Inhibition of Growth of AMIGO2-Expressing Cell by Antibody Conjugated with Substance Having Cytotoxic Activity Cells of the full-length-AMIGO2-expressing CHO prepared in Example 3 (3) were suspended in 10% FBS-containing F-12 HAM medium, and the suspension was inoculated into a flat-bottomed 96-well plate ($5 \times 10^3$ cells/well), followed by culturing overnight (70 µL/well). Subsequently, to the plate was added 10% FBS-containing F-12 HAM medium (product of Sigma corporation) containing an anti-AMIGO2 antibody (PPZ3124-described antibody) or a negative control antibody (K7124) (which serves as a primary antibody) (30 µL/well) (final concentration of PPZ3124-derived antibody or K7124 in each well: 0.1, 1, 10, or 100 ng/mL, each concentration was determined through triple measurement), and the plate was allowed to stand still in a 5% $CO_2$ incubator (37° C.) for one hour. The cells were washed twice with F-12 HAM medium (not containing FBS). To the plate was added saporin (plant toxin)-bound anti-mouse IgG goat IgG (trade name: Mab-ZAP, Funakoshi Corporation) (secondary antibody) which had been diluted with CHO-S-SFM-II medium (Invitrogen) to 0.21 µg/mL (150 µL/well), and the plate was allowed to stand still in a 5% $CO_2$ incubator (37° C.) for 48 hours. Subsequently, XTT reagent (cell growth kit II, product of Roche Diagnostics) was added to the wells (75 µL/well), and the plate was allowed to stand still in a 5% CO2 incubator (37° C.) for six hours. Absorbance at a wavelength of 450 nm (proportional to the number of living cells in each well) was measured by means of a microplate reader. The average of absorbances measured at wells in which the AMIGO2-expressing cells were reacted with only the secondary antibody was taken as 100%, and the relative absorbance (%) measured at a well in which the AMIGO2-expressing cells were reacted with both the secondary antibody and the primary antibody (any of the aforementioned concentrations) was determined. FIG. 19 is a graph showing relative absorbance (%) (i.e., cell survival rate (%)) plotted against primary antibody concentration.

When the PPZ3124-derived antibody was reacted, as a primary antibody, with the AMIGO2-expressing cells, cell survival rate (%) was considerably reduced in an antibody-concentration-dependent manner. This phenomenon indicates that the PPZ3124-derived antibody binds to AMIGO2 protein present on the cell membranes in an antibody-concentration-dependent manner; accordingly, the saporin (plant toxin)-bound anti-mouse IgG goat IgG binds to the AMIGO2 protein; and subsequently, the plant toxin saporin is incorporated into the cells through endocytosis as described in Example 19 and exhibits cytotoxicity. Thus, when the anti-AMIGO2 monoclonal antibody (PPZ3124-derived antibody) is labeled directly or indirectly with the plant toxin saporin, and the saporin-labeled antibody is caused to act on AMIGO2-expressing cells, growth of the cells can be inhibited.

The invention claimed is:

1. A diagnostic drug for pancreatic cancer comprising an anti-AMIGO2 monoclonal antibody, wherein the anti-AMIGO2 monoclonal antibody is produced by at least one hybridoma cell line selected from the group consisting of a hybridoma cell line identified as PPMX0502 and deposited as FERM BP-10809, a hybridoma cell line identified as PPMX0504 and deposited as FERM BP-10810, a hybridoma cell line identified as PPMX0507 and deposited as FERM BP-10811, a hybridoma cell line identified as PPMX0508 and deposited as FERM BP-10812, and a hybridoma cell line identified as PPMX0519 and deposited as FERM BP-10813.

2. The diagnostic drug for pancreatic cancer according to claim 1, wherein the anti-AMIGO2 monoclonal antibody is an antibody which binds to an extracellular region of AMIGO2 protein.

3. The diagnostic drug for pancreatic cancer according to claim 1, wherein the anti-AMIGO2 monoclonal antibody is exposed to blood, serum, plasma or organ tissue for reaction to thereby detect AMIGO2 protein.

4. The diagnostic drug for pancreatic cancer according to claim 1, wherein the anti-AMIGO2 monoclonal antibody is labeled and administered to a subject in need thereof, and AMIGO2 protein is detected through diagnostic imaging.

5. The diagnostic drug for pancreatic cancer according to claim 1, which is employed for selecting a patient to be treated from among pancreatic cancer patients.

6. The diagnostic drug for pancreatic cancer according to claim 1, wherein the anti-AMIGO2 monoclonal antibody is produced by the hybridoma cell line identified as PPMX0502 and deposited as FERM BP-10809.

7. The diagnostic drug for pancreatic cancer according to claim 1, wherein the anti-AMIGO2 monoclonal antibody is produced by the hybridoma cell line identified as PPMX0504 and deposited as FERM BP-10810.

8. The diagnostic drug for pancreatic cancer according to claim 1, wherein the anti-AMIGO2 monoclonal antibody is produced by the hybridoma cell line identified as PPMX0507 and deposited as FERM BP-10811.

9. The diagnostic drug for pancreatic cancer according to claim 1, wherein the anti-AMIGO2 monoclonal antibody is produced by the hybridoma cell line identified as PPMX0508 and deposited as FERM BP-10812.

10. The diagnostic drug for pancreatic cancer according to claim 1, wherein the anti-AMIGO2 monoclonal antibody is produced by the hybridoma cell line identified as PPMX0519 and deposited as FERM BP-10813.

11. A therapeutic drug for pancreatic cancer comprising an anti-AMIGO2 monoclonal antibody and a pharmaceutically acceptable carrier, wherein the anti-AMIGO2 monoclonal antibody is produced by at least one hybridoma cell line selected from the group consisting of a hybridoma cell line identified as PPMX0502 and deposited as FERM BP-10809, a hybridoma cell line identified as PPMX0504 and deposited as FERM BP-10810, a hybridoma cell line identified as PPMX0507 and deposited as FERM BP-10811, a hybridoma cell line identified as PPMX0508 and deposited as FERM BP-10812, and a hybridoma cell line identified as PPMX0519 and deposited as FERM BP-10813.

12. The therapeutic drug for pancreatic cancer according to claim 11, wherein the anti-AMIGO2 monoclonal antibody is an antibody which binds to an extracellular region of AMIGO2 protein.

13. The therapeutic drug for pancreatic cancer according to claim 11, wherein the anti-AMIGO2 monoclonal antibody is an antibody having cytotoxic activity.

14. The therapeutic drug for pancreatic cancer according to claim 11, wherein the anti-AMIGO2 monoclonal antibody is an antibody which is labeled with an isotope or which is bound to a compound having cytotoxic activity.

15. The therapeutic drug for pancreatic cancer according to claim 11, wherein the anti-AMIGO2 monoclonal antibody is produced by the hybridoma cell line identified as PPMX0502 and deposited as FERM BP-10809.

16. The therapeutic drug for pancreatic cancer according to claim 11, wherein the anti-AMIGO2 monoclonal antibody is produced by the hybridoma cell line identified as PPMX0504 and deposited as FERM BP-10810.

17. The therapeutic drug for pancreatic cancer according to claim 11, wherein the anti-AMIGO2 monoclonal antibody is produced by the hybridoma cell line identified as PPMX0507 and deposited as FERM BP-10811.

18. The therapeutic drug for pancreatic cancer according to claim 11, wherein the anti-AMIGO2 monoclonal antibody is produced by the hybridoma cell line identified as PPMX0508 and deposited as FERM BP-10812.

19. The therapeutic drug for pancreatic cancer according to claim 11, wherein the anti-AMIGO2 monoclonal antibody is produced by the hybridoma cell line identified as PPMX0519 and deposited as FERM BP-10813.

20. A diagnostic kit comprising a diagnostic drug for pancreatic cancer, the diagnostic drug for pancreatic cancer comprising an anti-AMIGO2 monoclonal antibody, wherein the anti-AMIGO2 monoclonal antibody is produced by at least one hybridoma cell line selected from the group consisting of a hybridoma cell line identified as PPMX0502 and deposited as FERM BP-10809, a hybridoma cell line identified as PPMX0504 and deposited as FERM BP-10810, a hybridoma cell line identified as PPMX0507 and deposited as FERM BP-10811, a hybridoma cell line identified as PPMX0508 and deposited as FERM BP-10812, and a hybridoma cell line identified as PPMX0519 and deposited as FERM BP-10813.

21. The diagnostic kit according to claim 20, wherein the anti-AMIGO2 monoclonal antibody is an antibody which binds to an extracellular region of AMIGO2 protein.

22. The diagnostic kit according to claim 20, wherein the anti-AMIGO2 monoclonal antibody is exposed to blood, serum, plasma or organ tissue for reaction to thereby detect AMIGO2 protein.

23. The diagnostic kit according to claim 20, wherein the anti-AMIGO2 monoclonal antibody is labeled and administered to a subject in need thereof, and AMIGO2 protein is detected through diagnostic aging.

24. The diagnostic kit according to claim 20, which is employed for selecting a patient to be treated from among pancreatic cancer patients.

25. The diagnostic kit according to claim 20, wherein the anti-AMIGO2 monoclonal antibody is produced by the hybridoma cell line identified as PPMX0502 and deposited as FERM BP-10809.

26. The diagnostic kit according to claim 20, wherein the anti-AMIGO2 monoclonal antibody is produced by the hybridoma cell line identified as PPMX0504 and deposited as FERM BP-10810.

27. The diagnostic kit according to claim 20, wherein the anti-AMIGO2 monoclonal antibody is produced by the hybridoma cell line identified as PPMX0507 and deposited as FERM BP-10811.

28. The diagnostic kit according to claim 20, wherein the anti-AMIGO2 monoclonal antibody is produced by the hybridoma cell line identified as PPMX0508 and deposited as FERM BP-10812.

29. The diagnostic kit according to claim 20, wherein the anti-AMIGO2 monoclonal antibody is produced by the hybridoma cell line identified as PPMX0519 and deposited as FERM BP-10813.

* * * * *

SEQUENCE LISTING

<160> NUMBER OF SEQ ID NOS: 7

<210> SEQ ID NO 1
<211> LENGTH: 3769
<212> TYPE: DNA
<213> ORGANISM: Homo sapiens
<220> FEATURE:
<221> NAME/KEY: CDS
<222> LOCATION: (469)..(2034)

<400> SEQUENCE: 1

```
ggggtcctgc agcctcccga gtgcggagag gcggggccgc ccgctgccgc ccggctgcct      60 gcgcccctc ccgcggcccc ggctctggga gcggggcgcc ccgcgcgcgg gcacacggcg      120
gccagagcgc cgaggcggta ccttcagcct gcaatgagag gaacccggga gagccccgg     180 gagccagcga agagcttggc tgctgcgtcc agggctgctg ctgccgccgc ggctgcttga     240
aactcctcaa agttgagagc cggctagagg gtgccgcccg ccgggagccg agggaaagg     300 aagtcgggag gtgcaagagt gacagacacg gacagacgga cgcgcagacc ttcggaaggc     360
actgcgtagg cagcctcccc ggagcccacg aggctcccca gcaccgttca ctggtgggag     420
gctgagccgg tggaaaagac accgggaaga gactcagagg cgaccata atg tcg tta     477
                                                    Met Ser Leu
                                                     1 cgt gta cac act ctg ccc acc ctg ctt gga gcc gtc gtc aga ccg ggc     525
Arg Val His Thr Leu Pro Thr Leu Leu Gly Ala Val Val Arg Pro Gly
  5                  10                  15 tgc agg gag ctg ctg tgt ttg ctg atg atc aca gtg act gtg ggc cct     573
Cys Arg Glu Leu Leu Cys Leu Leu Met Ile Thr Val Thr Val Gly Pro
 20                  25                  30                  35 ggt gcc tct ggg gtg tgc ccc acc gct tgc atc tgt gcc act gac atc     621
Gly Ala Ser Gly Val Cys Pro Thr Ala Cys Ile Cys Ala Thr Asp Ile
             40                  45                  50 gtc agc tgc acc aac aaa aac ctg tcc aag gtg cct ggg aac ctt ttc     669
Val Ser Cys Thr Asn Lys Asn Leu Ser Lys Val Pro Gly Asn Leu Phe
         55                  60                  65 aga ctg att aag aga ctg gac ctg agt tat aac aga att ggg ctt ctg     717
Arg Leu Ile Lys Arg Leu Asp Leu Ser Tyr Asn Arg Ile Gly Leu Leu
     70                  75                  80 gat tct gag tgg att cca gta tcg ttt gca aag ctg aac acc cta att     765
Asp Ser Glu Trp Ile Pro Val Ser Phe Ala Lys Leu Asn Thr Leu Ile
 85                  90                  95 ctt cgt cat aac aac atc acc agc att tcc acg ggc agt ttt tcc aca     813
Leu Arg His Asn Asn Ile Thr Ser Ile Ser Thr Gly Ser Phe Ser Thr
100                 105                 110                 115 act cca aat ttg aag tgt ctt gac tta tcg tcc aat aag ctg aag acg     861
Thr Pro Asn Leu Lys Cys Leu Asp Leu Ser Ser Asn Lys Leu Lys Thr
            120                 125                 130 gtg aaa aat gct gta ttc caa gag ttg aag gtt ctg gaa gtg ctt ctg     909
Val Lys Asn Ala Val Phe Gln Glu Leu Lys Val Leu Glu Val Leu Leu
        135                 140                 145 ctt tac aac aat cac ata tcc tat ctc gat cct tca gcg ttt gga ggg     957
Leu Tyr Asn Asn His Ile Ser Tyr Leu Asp Pro Ser Ala Phe Gly Gly
    150                 155                 160 ctc tcc cag ttg cag aaa ctc tac tta agt gga aat ttt ctc aca cag    1005
Leu Ser Gln Leu Gln Lys Leu Tyr Leu Ser Gly Asn Phe Leu Thr Gln
165                 170                 175 ttt ccg atg gat ttg tat gtt gga agg ttc aag ctg gca gaa ctg atg    1053
Phe Pro Met Asp Leu Tyr Val Gly Arg Phe Lys Leu Ala Glu Leu Met
180                 185                 190                 195
```

| | | |
|---|---|---|
| ttt tta gat gtt tct tat aac cga att cct tcc atg cca atg cac cac<br>Phe Leu Asp Val Ser Tyr Asn Arg Ile Pro Ser Met Pro Met His His<br>200                 205                 210 | | 1101 |
| ata aat tta gtg cca gga aaa cag ctg aga ggc atc tac ctt cat gga<br>Ile Asn Leu Val Pro Gly Lys Gln Leu Arg Gly Ile Tyr Leu His Gly<br>         215                 220                 225 | | 1149 |
| aac cca ttt gtc tgt gac tgt tcc ctg tac tcc ttg ctg gtc ttt tgg<br>Asn Pro Phe Val Cys Asp Cys Ser Leu Tyr Ser Leu Leu Val Phe Trp<br>               230                 235                 240 | | 1197 |
| tat cgt agg cac ttt agc tca gtg atg gat ttt aag aac gat tac acc<br>Tyr Arg Arg His Phe Ser Ser Val Met Asp Phe Lys Asn Asp Tyr Thr<br>245                 250                 255 | | 1245 |
| tgt cgc ctg tgg tct gac tcc agg cac tcg cgt cag gta ctt ctg ctc<br>Cys Arg Leu Trp Ser Asp Ser Arg His Ser Arg Gln Val Leu Leu Leu<br>260                 265                 270                 275 | | 1293 |
| cag gat agc ttt atg aat tgc tct gac agc atc atc aat ggt tcc ttt<br>Gln Asp Ser Phe Met Asn Cys Ser Asp Ser Ile Ile Asn Gly Ser Phe<br>               280                 285                 290 | | 1341 |
| cgt gcg ctt ggc ttt att cat gag gct cag gtc ggg gaa aga ctg atg<br>Arg Ala Leu Gly Phe Ile His Glu Ala Gln Val Gly Glu Arg Leu Met<br>         295                 300                 305 | | 1389 |
| gtc cac tgt gac agc aag aca ggt aat gca aat acg gat ttc atc tgg<br>Val His Cys Asp Ser Lys Thr Gly Asn Ala Asn Thr Asp Phe Ile Trp<br>               310                 315                 320 | | 1437 |
| gtg ggt cca gat aac aga ctg cta gag ccg gat aaa gag atg gaa aac<br>Val Gly Pro Asp Asn Arg Leu Leu Glu Pro Asp Lys Glu Met Glu Asn<br>325                 330                 335 | | 1485 |
| ttt tac gtg ttt cac aat gga agt ctg gtt ata gaa agc cct cgt ttt<br>Phe Tyr Val Phe His Asn Gly Ser Leu Val Ile Glu Ser Pro Arg Phe<br>340                 345                 350                 355 | | 1533 |
| gag gat gct gga gtg tat tct tgt atc gca atg aat aag caa cgc ctg<br>Glu Asp Ala Gly Val Tyr Ser Cys Ile Ala Met Asn Lys Gln Arg Leu<br>               360                 365                 370 | | 1581 |
| tta aat gaa act gtg gac gtc aca ata aat gtg agc aat ttc act gta<br>Leu Asn Glu Thr Val Asp Val Thr Ile Asn Val Ser Asn Phe Thr Val<br>         375                 380                 385 | | 1629 |
| agc aga tcc cat gct cat gag gca ttt aac aca gct ttt acc act ctt<br>Ser Arg Ser His Ala His Glu Ala Phe Asn Thr Ala Phe Thr Thr Leu<br>         390                 395                 400 | | 1677 |
| gct gct tgc gtg gcc agt atc gtt ttg gta ctt tac ctc tat ctg<br>Ala Ala Cys Val Ala Ser Ile Val Leu Val Leu Leu Tyr Leu Tyr Leu<br>405                 410                 415 | | 1725 |
| act cca tgc ccc tgc aag tgt aaa acc aag aga cag aaa aat atg cta<br>Thr Pro Cys Pro Cys Lys Cys Lys Thr Lys Arg Gln Lys Asn Met Leu<br>420                 425                 430                 435 | | 1773 |
| cac caa agc aat gcc cat tca tcg att ctc agt cct ggc ccc gct agt<br>His Gln Ser Asn Ala His Ser Ser Ile Leu Ser Pro Gly Pro Ala Ser<br>               440                 445                 450 | | 1821 |
| gat gcc tcc gct gat gaa cgg aag gca ggt gca ggt aaa aga gtg gtg<br>Asp Ala Ser Ala Asp Glu Arg Lys Ala Gly Ala Gly Lys Arg Val Val<br>               455                 460                 465 | | 1869 |
| ttt ttg gaa ccc ctg aag gat act gca gca ggg cag aac ggg aaa gtc<br>Phe Leu Glu Pro Leu Lys Asp Thr Ala Ala Gly Gln Asn Gly Lys Val<br>         470                 475                 480 | | 1917 |
| agg ctc ttt ccc agc gag gca gtg ata gct gag ggc atc cta aag tcc<br>Arg Leu Phe Pro Ser Glu Ala Val Ile Ala Glu Gly Ile Leu Lys Ser<br>         485                 490                 495 | | 1965 |
| acg agg ggg aaa tct gac tca gat tca gtc aat tca gtg ttt tct gac<br>Thr Arg Gly Lys Ser Asp Ser Asp Ser Val Asn Ser Val Phe Ser Asp<br>500                 505                 510                 515 | | 2013 |

-continued

```
aca cct ttt gtg gcg tcc act taatttgtgc ctatatttgt atgatgtcat    2064
Thr Pro Phe Val Ala Ser Thr
            520 aatttaatct gttcatattt aactttgtgt gtggtctgca aaataaacag caggacagaa   2124 attgtgttgt tttgttcttt gaaatacaac caaattctct taaaatgatt ggtaggaaat   2184 gaggtaaagt acttcagttc ctcaatgtgc cagagaaaga tggggttgtt ttccaaagtt   2244 taagttctag atcacaatat cttagctttt agcactattg gtaatttcag agtaggccca   2304 aaggtgatat gactcccatt gtcccttat ttaggatatt gaaagaaaaa ataaacttta    2364 tgtattagtg tcctttaaaa atagactttg ctaacttact agtaccagag ttattttaaa   2424 gaaaaacact agtgtccaat ttcattttta aaagatgtag aaagaagaat caagcatcaa   2484 ttaattataa agcctaaagc aaagttagat ttggggggtta ttcagccaaa attaccgttt  2544 tagaccagaa tgaatagact acactgataa aatgtactgg ataatgccac atcctatatg   2604 gtgttataga aatagtgcaa ggaaagtaca tttgtttgcc tgtcttttca ttttgtacat   2664 tcttcccatt ctgtattctt gtacaaaaga tctcattgaa aatttaaagt catcataatt   2724 tgttgccata aatatgtaag tgtcaatacc aaaatgtctg agtaacttct taaatccctg   2784 ttctagcaaa ctaatattgg ttcatgtgct tgtgtatatg taaatcttaa attatgtgaa   2844 ctattaaata gaccctactg tactgtgctt tggacatttg aattaatgta aatatatgta   2904 atctgtgact tgatattttg tttatttgg ctatttaaaa acataaatct aaaatgtctt    2964 atgttatcag attatgctat tttgtataaa gcaccactga tagcaaatct ctctccaaaa   3024 ttcttatagt aaagttgatt tttttaaagg gggaggggaa ggctttaatg tgttctagat   3084 caatttatac cttccgtatg acgttttact ctgatatcat tgtgcacttt agccagatcc   3144 agaaaacact caaatttatt ttgcaacaag tgagagccca ggagacctcc ttattatcct   3204 gtctctgctt tgaggcaatc aagtaccctc tctgaaccta ggttccctca tctgtaaaac   3264 aaaggtttca gaccagatgg tgtttaaggt ttctccccat actggaatga atgatttctt   3324 ggtggtatta gcatcatcac agacctatac ttgcttttctg aaactctacc acatactgaa  3384 ggaatacagg aatgggatta agatgactag catagcagtg tacagcttga agagatgttc   3444 cacatcatca ctccagctcc ttctctttttc tcagggacaa atgaggccca gagagaatac   3504 gacctgtgta aggtcaaaca gtggcaggga aagaaggaga gctggggttt agcattctcc   3564 ctggtgaaga ttggaggtcc aaagaaatga ctccttttta agggatgggc ataaaaaagt    3624 gatcaaaaca ttgcaaagga gaatcaaaga ttgattgtcc tggggctaag aaagaagata   3684 atttttaaag aatgggagtg ggcaacagtg aaaatattg cagataagta gataaggata    3744 gaagatcaac cactgactgg tagta                                         3769
```

<210> SEQ ID NO 2
<211> LENGTH: 522
<212> TYPE: PRT
<213> ORGANISM: Homo sapiens

<400> SEQUENCE: 2

```
Met Ser Leu Arg Val His Thr Leu Pro Thr Leu Leu Gly Ala Val Val
1               5                   10                  15

Arg Pro Gly Cys Arg Glu Leu Leu Cys Leu Leu Met Ile Thr Val Thr
            20                  25                  30

Val Gly Pro Gly Ala Ser Gly Val Cys Pro Thr Ala Cys Ile Cys Ala
        35                  40                  45
```

-continued

```
Thr Asp Ile Val Ser Cys Thr Asn Lys Asn Leu Ser Lys Val Pro Gly
     50                  55                  60

Asn Leu Phe Arg Leu Ile Lys Arg Leu Asp Leu Ser Tyr Asn Arg Ile
 65                  70                  75                  80

Gly Leu Leu Asp Ser Glu Trp Ile Pro Val Ser Phe Ala Lys Leu Asn
                     85                  90                  95

Thr Leu Ile Leu Arg His Asn Asn Ile Thr Ser Ile Ser Thr Gly Ser
                100                 105                 110

Phe Ser Thr Thr Pro Asn Leu Lys Cys Leu Asp Leu Ser Ser Asn Lys
            115                 120                 125

Leu Lys Thr Val Lys Asn Ala Val Phe Gln Glu Leu Lys Val Leu Glu
    130                 135                 140

Val Leu Leu Leu Tyr Asn Asn His Ile Ser Tyr Leu Asp Pro Ser Ala
145                 150                 155                 160

Phe Gly Gly Leu Ser Gln Leu Gln Lys Leu Tyr Leu Ser Gly Asn Phe
                165                 170                 175

Leu Thr Gln Phe Pro Met Asp Leu Tyr Val Gly Arg Phe Lys Leu Ala
                180                 185                 190

Glu Leu Met Phe Leu Asp Val Ser Tyr Asn Arg Ile Pro Ser Met Pro
            195                 200                 205

Met His His Ile Asn Leu Val Pro Gly Lys Gln Leu Arg Gly Ile Tyr
    210                 215                 220

Leu His Gly Asn Pro Phe Val Cys Asp Cys Ser Leu Tyr Ser Leu Leu
225                 230                 235                 240

Val Phe Trp Tyr Arg Arg His Phe Ser Ser Val Met Asp Phe Lys Asn
                245                 250                 255

Asp Tyr Thr Cys Arg Leu Trp Ser Asp Ser Arg His Ser Arg Gln Val
                260                 265                 270

Leu Leu Leu Gln Asp Ser Phe Met Asn Cys Ser Asp Ser Ile Ile Asn
            275                 280                 285

Gly Ser Phe Arg Ala Leu Gly Phe Ile His Glu Ala Gln Val Gly Glu
    290                 295                 300

Arg Leu Met Val His Cys Asp Ser Lys Thr Gly Asn Ala Asn Thr Asp
305                 310                 315                 320

Phe Ile Trp Val Gly Pro Asp Asn Arg Leu Leu Glu Pro Asp Lys Glu
                325                 330                 335

Met Glu Asn Phe Tyr Val Phe His Asn Gly Ser Leu Val Ile Glu Ser
                340                 345                 350

Pro Arg Phe Glu Asp Ala Gly Val Tyr Ser Cys Ile Ala Met Asn Lys
            355                 360                 365

Gln Arg Leu Leu Asn Glu Thr Val Asp Val Thr Ile Asn Val Ser Asn
    370                 375                 380

Phe Thr Val Ser Arg Ser His Ala His Glu Ala Phe Asn Thr Ala Phe
385                 390                 395                 400

Thr Thr Leu Ala Ala Cys Val Ala Ser Ile Val Leu Val Leu Leu Tyr
                405                 410                 415

Leu Tyr Leu Thr Pro Cys Pro Cys Lys Cys Lys Thr Lys Arg Gln Lys
                420                 425                 430

Asn Met Leu His Gln Ser Asn Ala His Ser Ser Ile Leu Ser Pro Gly
            435                 440                 445

Pro Ala Ser Asp Ala Ser Ala Asp Glu Arg Lys Ala Gly Ala Gly Lys
    450                 455                 460

Arg Val Val Phe Leu Glu Pro Leu Lys Asp Thr Ala Ala Gly Gln Asn
465                 470                 475                 480
```

Gly Lys Val Arg Leu Phe Pro Ser Glu Ala Val Ile Ala Glu Gly Ile
            485                 490                 495

Leu Lys Ser Thr Arg Gly Lys Ser Asp Ser Asp Ser Val Asn Ser Val
        500                 505                 510

Phe Ser Asp Thr Pro Phe Val Ala Ser Thr
        515                 520

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      designed DNA primer based on AMIGO2 gene

<400> SEQUENCE: 3
atggtaccat gtcgttacgt gtacac                                        26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      designed DNA primer based on AMIGO2 gene

<400> SEQUENCE: 4
aagatatcag tggacgccac aaaagg                                        26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      designed DNA primer based on AMIGO2 gene

<400> SEQUENCE: 5
cgctctagag cgttaaatgc ctcatg                                        26

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      designed DNA primer based on AMIGO2 gene

<400> SEQUENCE: 6
taggtacccc aggtcgggga aagactg                                       27

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      designed DNA primer based on AMIGO2 gene

<400> SEQUENCE: 7
atggtacctg atgagcatgg gatctgct                                      28